(12) United States Patent  (10) Patent No.: US 8,344,001 B2
Hohlweg et al.  (45) Date of Patent: Jan. 1, 2013

(54) HETEROCYCLIC H3 ANTAGONISTS

(75) Inventors: Rolf Hohlweg, Humlebaek (DK); Jane Marie Lundbeck, Glostrup (DK); Johannes Cornelis de Jong, Groningen (NL)

(73) Assignee: High Point Pharmaceuticals, LLC, High Point, NC (US)

( * ) Notice: Subject to any disclaimer, the term of this patent is extended or adjusted under 35 U.S.C. 154(b) by 0 days.

(21) Appl. No.: 12/663,103

(22) PCT Filed: May 19, 2008

(86) PCT No.: PCT/US2008/064106
§ 371 (c)(1),
(2), (4) Date: Jun. 25, 2010

(87) PCT Pub. No.: WO2008/154126
PCT Pub. Date: Dec. 18, 2008

(65) Prior Publication Data
US 2010/0267721 A1   Oct. 21, 2010

Related U.S. Application Data

(60) Provisional application No. 60/934,514, filed on Jun. 13, 2007.

(30) Foreign Application Priority Data

Jun. 11, 2007 (EP) .................................... 07109949

(51) Int. Cl.
*A61K 31/44* (2006.01)
(52) U.S. Cl. ........ 514/334; 514/332; 514/277; 514/183; 546/268.1
(58) Field of Classification Search .................. None
See application file for complete search history.

(56) References Cited

U.S. PATENT DOCUMENTS

| | | | |
|---|---|---|---|
| 2,993,899 A | 7/1961 | Dawson |
| 3,309,370 A | 3/1967 | Schut |
| 3,753,988 A | 8/1973 | Rodway et al. |
| 3,886,161 A | 5/1975 | Hardtmann |
| 4,026,891 A | 5/1977 | Austel et al. |
| 4,163,849 A | 8/1979 | Lumma, Jr. et al. |
| 4,223,036 A | 9/1980 | Heeres et al. |
| 4,251,658 A | 2/1981 | Szilagyi et al. |
| 4,265,894 A | 5/1981 | Gootjes |
| 4,339,579 A | 7/1982 | Freed |
| 4,518,712 A | 5/1985 | Fujimura et al. |
| 4,616,014 A | 10/1986 | Teraji et al. |
| 4,673,675 A | 6/1987 | Robba et al. |
| 4,758,566 A | 7/1988 | Uno et al. |
| 4,824,846 A | 4/1989 | Kampe et al. |
| 4,935,426 A | 6/1990 | Zipplies et al. |
| 5,001,125 A | 3/1991 | Stokbroekx et al. |
| 5,670,505 A | 9/1997 | Matsuo et al. |
| 5,929,089 A | 7/1999 | Jegham et al. |
| 6,130,217 A | 10/2000 | Arnold et al. |
| 6,316,475 B1 * | 11/2001 | Bennani et al. ................ 514/343 |
| 6,864,261 B2 | 3/2005 | Gharagozloo et al. |
| 6,906,060 B2 | 6/2005 | Peschke et al. |
| 7,115,634 B2 | 10/2006 | Thurieau et al. |
| 7,186,721 B2 | 3/2007 | Peschke et al. |
| 7,229,997 B2 | 6/2007 | Nilsson et al. |

(Continued)

FOREIGN PATENT DOCUMENTS

AU          639529          7/1993

(Continued)

OTHER PUBLICATIONS

Abdel-Magid et al., "Reductive Amination of Aldehydes and Ketones with Sodium Triacetoxyborohydride. Studies on Direct and Indirect Reductive Amination Procedures," J. Org. Chem., 61(11):3849-3862 (1996).
Adam et al., "Concise Synthesis of 1H-Pyrazin-2-ones and 2-Aminopyrazines," Synlett, No. 11:2031-2033 (2004).
Ballaben et al., "Reactivity of cyclopentanone enamines towards non-symmetric electrophilic diazenes," Gazzetta Chimica Italiana, 123(7):387-391 (1993) (abstract only).

(Continued)

Primary Examiner — Anish Gupta
Assistant Examiner — Theodore R West
(74) Attorney, Agent, or Firm — Samuel B. Rollins

(57) ABSTRACT

Compound of formula (I) wherein W, X, Y, Z is —C($R^1$)= or N; $R^1$ is hydrogen or alkyl, V is N or C (i.e. carbon), A is a bond or an alkylene linker with 1 to 3 carbon atoms, with the proviso that when A is a bond, V must be CH, R is ethyl, propyl, a branched $C_{3-6}$ alkyl or a cyclic $C_{3-8}$ alkyl, m and n is 1-3, D is heteroaryl optionally substituted with halogen, hydroxy, cyano, alkyl, cycloalkyl, alkoxy, —$(CH_2)_o$—$(C=O)_p$—$NR^2R^3$, or D is aryl optionally substituted with one or more of the groups independently selected from hydrogen, halogen, hydroxy, cyano, alkyl, cycloalkyl, haloalkyl, alkoxy, haloalkoxy, alkylsulfonyl, alkylsulfinyl, heterocyclyl, heterocyclylalkyl, heterocyclyl-alkoxy, heterocyclylcarbonyl, alkylcarbonyl, alkoxycarbonyl, alkylcarboxy, cyanoalkyl, hydroxyalkyl, alkoxyalkyl, alkylcarbonylamino, alkylcarbonylaminoalkyl, arylcarbonylamino, aryl-carbonylaminoalkyl, heteroarylcarbonylamino or heteroarylcarbonylaminoalkyl, —$(CH_2)_o$—$(C=O)_p$—$NR^2R^3$, wherein o is 0-3, p is 0 or 1, and $R^2$ and $R^3$ independently are hydrogen, alkyl or cycloalkyl; or $R^2$ and $R^3$, can together with the attached nitrogen form a heterocyclyl group, and salts and solvates thereof have binding affinity for the histamine H3 receptor.

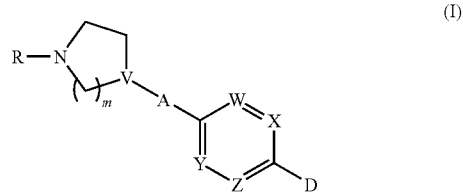

(I)

36 Claims, No Drawings

U.S. PATENT DOCUMENTS

| | | | |
|---|---|---|---|
| 7,294,626 B2 * | 11/2007 | Hohlweg | 514/252.02 |
| 7,494,994 B2 | 2/2009 | Desos et al. | |
| 7,494,995 B2 | 2/2009 | Desos et al. | |
| 7,547,693 B2 | 6/2009 | Ohtake et al. | |
| 7,632,950 B2 * | 12/2009 | Kuwabara et al. | 546/255 |
| 2003/0073672 A1 | 4/2003 | Breitenbucher et al. | |
| 2003/0236259 A1 | 12/2003 | Hohlweg et al. | |
| 2004/0023946 A1 | 2/2004 | Peschke et al. | |
| 2006/0293310 A1 | 12/2006 | Abouabdellah et al. | |
| 2009/0176793 A1 | 7/2009 | Hohlweg | |
| 2009/0264435 A1 | 10/2009 | Hohlweg et al. | |
| 2009/0312309 A1 | 12/2009 | Hohlweg et al. | |
| 2010/0298316 A1 | 11/2010 | Dorwald et al. | |
| 2011/0071159 A1 | 3/2011 | Lundbeck et al. | |

FOREIGN PATENT DOCUMENTS

| | | |
|---|---|---|
| DE | 2609746 A1 | 10/1976 |
| DE | 2804096 A1 | 8/1978 |
| DE | 2824764 A1 | 12/1979 |
| DE | 3803860 A1 | 8/1989 |
| EP | 0034752 B1 | 6/1983 |
| EP | 0050072 B1 | 12/1984 |
| EP | 0156433 A2 | 10/1985 |
| EP | 0236140 A2 | 9/1987 |
| EP | 0459819 A2 | 12/1991 |
| EP | 0327912 B1 | 4/1992 |
| EP | 0385237 B1 | 6/1994 |
| EP | 0320032 B1 | 1/1995 |
| EP | 0978512 A1 | 2/2000 |
| EP | 1721896 A1 | 11/2006 |
| EP | 1721897 A1 | 11/2006 |
| EP | 1020445 B1 | 8/2008 |
| GB | 753166 | 7/1956 |
| GB | 1345880 | 2/1974 |
| WO | WO 94/14780 A1 | 7/1994 |
| WO | WO 94/22846 A1 | 10/1994 |
| WO | WO 97/02245 A1 | 1/1997 |
| WO | WO 97/17345 A1 | 5/1997 |
| WO | WO 98/27081 A1 | 6/1998 |
| WO | WO 99/21845 A2 | 5/1999 |
| WO | WO 99/42458 A1 | 8/1999 |
| WO | WO 00/66578 A1 | 11/2000 |
| WO | WO 01/32646 A2 | 5/2001 |
| WO | WO 01/32659 A1 | 5/2001 |
| WO | WO 01/42241 A1 | 6/2001 |
| WO | WO 01/44201 A1 | 6/2001 |
| WO | WO 01/64645 A2 | 9/2001 |
| WO | WO 01/66534 A2 | 9/2001 |
| WO | WO 01/74773 A2 | 10/2001 |
| WO | WO 01/74810 A2 | 10/2001 |
| WO | WO 01/74813 A2 | 10/2001 |
| WO | WO 01/74814 A1 | 10/2001 |
| WO | WO 01/74815 A2 | 10/2001 |
| WO | WO 02/12190 A2 | 2/2002 |
| WO | WO 02/060392 A2 | 8/2002 |
| WO | WO 03/066604 A2 | 8/2003 |
| WO | WO 03/104235 A1 | 12/2003 |
| WO | WO 2004/054973 A2 | 7/2004 |
| WO | WO 2005/009976 A1 | 2/2005 |
| WO | WO 2005/100344 A1 | 10/2005 |
| WO | WO 2006/004589 A2 | 1/2006 |
| WO | WO 2006/050389 A2 | 5/2006 |
| WO | WO 2006/058649 A1 | 6/2006 |
| WO | WO 2006/075160 A1 | 7/2006 |
| WO | WO 2006/077387 A2 | 7/2006 |
| WO | WO 2006/113704 A2 | 10/2006 |
| WO | WO 2007/003604 A2 | 1/2007 |
| WO | WO 2007/011820 A2 | 1/2007 |
| WO | WO 2007/016496 A2 | 2/2007 |

OTHER PUBLICATIONS

Brown et al., "Unfused Heterobicycles as Amplifiers of Phleomycin. III. Thiazolypyridines and Bipyrimidines with Strongly Basic Side Chains," Australian Journal of Chemistry, 34:2423-2429 (1981).
Byrn et al., "Hydrates and Solvates," Solid-State Chemistry of Drugs, 2d, Chapter 11, 233-247 (1999).
Celanire et al., "Keynote review: Histamine H3 receptor antagonists reach out for the clinic," Drug Discovery Today, 10(23/24):1613-1627 (2005).
Contreras et al., "Aminopyridazines as Acetylcholinesterase Inhibitors," J. Med. Chem., 42:730-741 (1999).
Contreras et al., "Design, Synthesis, and Structure-Activity Relationships of a Series of 3-[2-(1-Benzylpiperidin-4-yl)ethylamino]pyridazine Derivatives as Acetylcholinesterase Inhibitors," J. Med. Chem., 44:2707-2718 (2001).
Coppola et al., "Pyrimidones. 2. Synthesis and Reactions of 2-Chloropyrimidines," J. Heterocyclic Chemistry, 17:1479-1482 (1980).
Database Beilstein, Beilstein Institut zur Foerderung der Chemischen Wissenschaften, DE; 5688187 BRN 4807006 1989, XP002355796 abstract.
Database Beilstein, Beilstein Institut zur Foerderung der Chemischen Wissenschaften, DE; BRN 4182175 1991, XP002355795 abstract.
Database Beilstein, Beilstein Institut zur Foerderung der Chemischen Wissenschaften, DE; BRN 4870130 1991, XP002355793 abstract.
Database Beilstein, Beilstein Institut zur Foerderung der Chemischen Wissenschaften, DE; BRN 6398075 1988, XP002355794 abstract.
Eguchi et al., "Studies on Antiatherosclerotic Agents. Synthesis and Inhibitory Activities on Platelet Aggregation of 4-Aryl Derivatives of 7-Ethoxycarbonyl-6,8-dimethyl-1(2H)-phthalazinone," Chemical & Pharmaceutical Bulletin, 39(8):2009-2015 (1991).
European Search Report for European Patent Application No. 07109949.3 mailed Jul. 17, 2008.
European Search Report for European Patent Application No. 07109949.3 mailed May 16, 2008.
European Search Report for European Patent Application No. 08755859.9 mailed May 7, 2010.
Falorni et al., "Chiral Ligands Containing Heteroatoms. 7. An Investigation on the Stereochemistry of the Ketone Reductions by Chiral Diamines/Tin Hydride Systems.," Tetrahedron: Asymmetry 2(4):287-298 (1991).
Ganellin et al., "Synthesis of Potent Non-imidazole Histamine H3-Receptor Antagonists," Arch. Pharm. Pharm. Med. Chem., 331:395-404 (1998).
Giannangeli et al., "Effect of Modifications of the Alkylpiperazine Moiety of Trazodone on 5HT2A and alpha1 Receptor Binding Affinity," J. Med. Chem., 42:336-345 (1999).
Grant et al., eds., Grant & Hackh's Chemical Dictionary, 5th Ed., McGraw Hill, New York, pp. 147 and 289 (1987).
Guery et al., "Synthesis of 4-Aryl-1-(4-methylpiperazin-1-yl)phthalazines by Suzuki-type Cross-coupling Reaction," Synthesis, No. 5:699-701 (2001).
Guillory, "Generation of Polymorphs, Hydrates, Solvates, and Amorphous Solids," in: Polymorphism in Pharmaceutical Solids, Harry G. Brittain, Ed., Chapter 5, pp. 183-226 (1999).
Haider et al., "Product Class 10: Phthalazines," in: Science of Synthesis: Houben-Weyl Methods of Molecular Transformations, Y. Yamamoto, Ed., Georg Thieme Verlag, Stuttgart, pp. 315-372 (2004).
Hancock, "The challenge of drug discovery of a GPCR target: Analysis of preclinical pharmacology of histamine H3 antagonists/inverse agonists," Biochemical Pharmacology, 71:1103-1113 (2006).
Hanson et al., "Phenylpiperazine-Based Radiopharmaceuticals for Brain Imaging. 3. Synthesis and Evaluation of Radioiodinated 1-Alkyl-4-phenylpiperazines," Journal of Medicinal Chemistry, 30(1):29-34 (1987).
Haugwitz et al., "Antiparasitic Agents. 5. Synthesis and Anthelmintic Activities of Novel 2-Heteroaromatic-Substituted Isothiocyanatobenzoxazoles and Benzothiazoles," J. Med. Chem., 25:969-974 (1982).
Hori et al., "Novel 4-substituted 2-piperazinylquinazolines as potent anticonvulsive and antihypoxic agents," Chemical & Pharmaceutical Bulletin, 38(5):1286-1291 (1990) (abstract only).
Hori et al., "Potential nootropic agents, 4-alkoxy-2-(1-piperazinyl)quinazoline derivatives," Chemical & Pharmaceutical Bulletin, 39(2):367-371 (1991) (abstract only).
Hu et al., "Development of a novel therapeutic suppressor of brain proinflammatory cytokine up-regulation that attenuates synaptic dysfunction and behavioral deficits," Bioorganic & Medicinal Chemistry Letters 17, pp. 414-418 (2007).

Irwin et al., "Alkyl Derivatives of Tetrahydroisoquinoline, 1-Phenylpiperazine, and 4-Diphenylmethylpiperidine," Journal of Medicinal Chemistry, 15(6):690-692 (1972).

Kawaguchi et al., "Parallel dose-response studies of the voltage-dependent Na+ channel antagonist BW619C89, and the voltage-dependent Ca2+ channel antagonist nimodipine, in rat transient focal cerebral ischaemia," Eur. J. Pharm., 364:99-105 (1999).

Klauschenz et al., "Synthesis and cardiotonic activity of 6-substituted 5-cyano-(3,4'-bipyridine)-1'-oxides and related compounds: molecular structure of 5-cyano-6-morpholino-(3,4'-bipyridine)-1'-oxide (AWD 122-239)," Eur. J. Med. Chem., 29:175-184 (1994).

Leurs et al., "The Histamine H3 Receptor: from Gene Cloning to H3 Receptor Drugs," Nature Reviews/Drug Discovery, 4:107-120 (2005).

Leurs et al., "The medicinal chemistry and therapeutic potentials of ligands of the histamine H3 receptor," in Progress in Drug Research, Ernst Jucker, Ed., 45:107-165 (1995).

Leurs et al., "Therapeutic potential of histamine H3 receptor agonists and antagonists," Trends in Pharmacological Sciences, 19(5):177-183 (1998).

Levay et al., "Correlation of the Chemical Reactivity of Some Tetrazine Derivatives with Their Reactivity toward Ortho-positronium Atoms and Their LUMO Energies," J. Phys. Chem. A, 108:1753-1756 (2004).

Linney et al., "Design, Synthesis, and Structure-Activity Relationships of Novel Non-Imidazole Histamine H3 Receptor Antagonists," J. Med. Chem., 43:2362-2370 (2000).

Lumma, Jr. et al., "Piperazinylpyrazines with Central Serotoninmimetic Activity," J. Med. Chem., 21(6):536-542 (1978).

Mackins et al., "Therapeutic potential of H3-receptor agonists in myocardial infarction," Expert Opinion on Investigational Drugs, 9(11):2537-2542 (2000).

Malmlof et al., "Targeting of the Central Histaminergic System for Treatment of Obesity and Associated Metabolic Disorders," Drug Development Research, 67:651-665 (2006).

Mazarguil et al., "Enamines of N-methyl- and N-phenylpiperazine. I. Synthesis and physicochemical study," Bulletin de La Societe Chimique de France, 1:319-324 (1969) (abstract only).

Mazarguil et al., "Enamines of N-methyl and N-phenylpiperazines. Synthesis of unsymmetrical N,N'-disubstituted and N-monosubstituted piperazines," Sciences Chimique, 267(12):724-727 (1968) (abstract only).

McIntyre et al., "Pyridazine Based Inhibitors of p38 MAPK," Bioorganic & Medicinal Chemistry Letters, 12:689-692 (2002).

McLeod et al., "Sch 50971, an Orally Active Histamine H3 Receptor Agonist, Inhibits Central Neurogenic Vascular Inflammation and Produces Sedation in the Guinea Pig," J. Pharmacol. Exp. Ther., 287(1):43-50 (1998).

Mir et al., "Nucleophilic Substitution Reactions of Heterocyclic Amines and Acyclic Diamines with Chlorofluoroolefins and Hexafluoropropylene Oxide," J. Org. Chem. 59:173-177 (1994).

Mokrosz et al., "Structure-Activity Relationship Studies of Central Nervous System Agents. 5. Effect of the Hydrocarbon Chain on the Affinity of 4-Substituted 1-(3-Chlorophenyl)piperazines for 5-HT1A Receptor Site," J. Med. Chem., 35:2369-2374 (1992).

Morisset et al., "High constitutive activity of native H3 receptors regulates histamine neurons in brain," Nature, 408:860-864 (2000).

Parrot et al., "Synthesis of Substituted 3-Amino-6-arylpyridazines via Suzuki Reaction," Synthesis, No. 7, pp. 1163-1168 (1999).

PCT International Search Report for Application No. PCT/US2008/064106 mailed Aug. 15, 2008.

PCT Written Opinion for Application No. PCT/US2008/064106 mailed Aug. 15, 2008.

Pending claims for U.S. Appl. No. 11/917,823, filed Jun. 8, 2009.

Pending claims for U.S. Appl. No. 12/294,756, filed Sep. 26, 2008.

Pending claims for U.S. Appl. No. 12/301,919, filed Nov. 21, 2008.

Pending claims for U.S. Appl. No. 12/367,952, filed Feb. 9, 2009.

Prasad et al., "Potential Antihypertensive Agents. II. Unsymmetrically 1,4-Disubstituted Piperazines," J. Med. Chem., 11:1144-1150 (1968).

Refaat et al., "Synthesis and Antidepressant Activity of Novel Pyridazine Derivatives," Bulletin of the Faculty of Pharmacy, Cairo University, 42(2):415-423 (2004).

Rival et al., "5-HT3 Antagonists Derived from Aminopyridazine-type Muscarinic M1 Agonists," J. Med. Chem., 41(3):311-317 (1998).

Rodriguez-Spong et al., "General principles of pharmaceutical solid polymorphism: a supramolecular perspective," Advanced Drug Delivery Reviews, 56:241-274 (2004).

Rohet et al., "Synthesis and Analgesic Effects of 3-Substituted 4,6-Diarylpyridazine Derivatives of the Arylpiperazine Class," Bioorganic & Medicinal Chemistry, 5(4):655-659 (1997).

Stark et al., "Developments of histamine H3-receptor antagonists," Drugs of the Future, 21(5):507-520 (1996).

Steck et al., "Pyridazines VIII. Some 6-Aryl-3-(basically-substituted) Pyridazines," J. of Heterocyclic Chemistry, 12:1009-1013 (1975).

Steen et al., "Structure-Affinity Relationship Studies on 5-HT1A Receptor Ligands. I. Heterobicyclic Phenylpiperazines with N4-Alkyl Substituents," Journal of Medicinal Chemistry, 36(19):2751-2760 (1993).

Tafesse et al., "Synthesis and evaluation of pyridazinylpiperazines as vanilloid receptor 1 antagonists," Bioorganic & Medicinal Chemistry Letters, 14:5513-5519 (2004).

Tamayo et al., "Design and synthesis of potent pyridazine inhibitors of p38 MAP kinase," Bioorganic & Medicinal Chemistry Letters, 15:2409-2413 (2005).

Tozer et al., "Histamine H3 receptor antagonists," Expert Opinion on Therapeutic Patents, 10(7):1045-1055 (2000).

Vippagunta et al., "Crystalline solids," Advanced Drug Delivery Reviews, vol. 48, pp. 3-26 (2001).

Walczynski et al., "Non-Imidazole Histamine H3 Ligands, Part 2: New 2-Substituted Benzothiazoles as Histamine H3 Antagonists," Arch. Pharm. Pharm. Med. Chem., 332:389-398 (1999).

Walczynski et al., "Non-imidazole histamine H3 ligands. Part I. Synthesis of 2-(1-piperazinyl)- and 2-(hexahydro-1H-1,4-diazepin-1-yl)benzothiazole derivatives as H3-antagonists with H1 blocking activities," II Farmaco 54:684-694 (1999).

Walczynski et al., "Non-imidazole histamine H3 ligands. Part III. New 4-n-propylpiperazines as non-imidazole histamine H3-antagonists," European Journal of Medicinal Chemistry, 40:15-23 (2005).

Werbel et al., "Synthesis and Antimalarial Effects of N,N-Dialkyl-6-(substituted phenyl)-1,2,4,5-tetrazin-3-amines," J. of Heterocyclic Chemistry, 16:881-894 (1979).

Wu et al., "Synthesis and platelet aggregation activity of 6-[4-substituted-piperazinyl]phenyl]-4,5-dihydro-3(2H)-pyridazinones," Zhongguo Yaowu Huaxue Zazhi, 9(3):172-175, 185 (1999) (abstract only).

Xu et al., "Studies on synthesis and anticonvulsant activity of 3-substituted piperazino-6-(substituted-phenyl) pyridazines," Journal of Beijing Medical University, 23(6):477-480 (1991).

Xu et al., "Synthesis and anticonvulsant activity of 6-aryl-3-(4-methylpiperazine) pyridazine compounds," Chinese Journal of Medicinal Chemistry 1(1):42-48 (1990).

Zaragoza et al., "2-(4-Alkylpiperazin-1-yl)quinolines as a New Class of Imidazole-Free Histamine H3 Receptor Antagonists," Journal of Medicinal Chemistry, 48(1):306-311 (2005).

* cited by examiner

HETEROCYCLIC H3 ANTAGONISTS

CROSS-REFERENCE TO RELATED APPLICATIONS

This application is the U.S. national stage application, pursuant to 35 U.S.C. § 371, of PCT Application No. PCT/US2008/64106, filed May 19, 2008, which claims the benefit of priority to European Patent Application No. 07109949.3, filed Jun. 11, 2007, and U.S. Provisional Patent Application No. 60/934,514, filed Jun. 13, 2007.

FIELD OF THIS INVENTION

The present invention relates to novel compounds, to the use of these compounds in pharmaceutical compositions, to pharmaceutical compositions comprising the compounds, and to methods of treatment employing these compounds or compositions. The present compounds show a high and selective binding affinity for the histamine H3 receptor, indicating histamine H3 receptor antagonistic, inverse agonistic or agonistic activity. As a result, the compounds are useful for the treatment of diseases or disorders related to the histamine H3 receptor.

BACKGROUND OF THIS INVENTION

The existence of the histamine H3 receptor has been known for several years and the receptor is of current interest for the development of new medicaments. Recently, the human histamine H3 receptor has been cloned. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor shows intrinsic, constitutive activity, in vitro as well as in vivo (i.e., it is active in the absence of an agonist). Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

In view of the art's interest in histamine H3 receptor agonists, inverse agonists and antagonists, novel compounds which interact with the histamine H3 receptor would be a highly desirable contribution to the art. Several publications disclose the preparation and use of histamine H3 agonists and antagonists. While earlier H3 ligands were more or less close analogues of histamine, newer imidazole-free ligands of the histamine H3 receptor have been described (see, e.g., Linney et al. in *J. Med. Chem.* 2000, 43, 2362-2370; U.S. Pat. No. 6,316,475, WO 01/66534, WO 01/74810, see also review by Celanire et al. in *Drug Discov. Today* 10:1613-1627).

WO 00/66578 claims certain 3- or 4-(imidazol-2-yl)pyridines being substituted in the 4 position of the imidazole ring. It is mentioned that mammals having a disease or condition mediated by NPY can be treated with such a compound.

Our earlier application, WO 2003/066604 (our internal ref.: 6447), claims certain piperazines being substituted in the 1 and 4 positions.

Our earlier application, WO 2005/009976 A1 (our internal ref.: 6739), claims certain 3-(4-isopropylpiperazin-1-yl)-6-phenylpyridazines being substituted in the para position of the phenyl ring. In the specification, no pharmacological data are given for the compounds prepared.

WO 2005/028438 claims certain piperidines being substituted in the 1 and 4 position.

OBJECTS OF THIS INVENTION

The object of this invention is to overcome or ameliorate at least some of the disadvantages of the prior art. Hence, not all the objects mentioned below may be fully overcome or ameliorated. Further objects of this invention are mentioned below.

DEFINITIONS

In the structural formulae given herein and throughout the present specification, the following terms have the indicated meaning:

The term "hydroxy" shall mean the radical —OH, the term "oxy" shall mean the radical —O—, the term "oxo" shall mean the radical =O, the term "carbonyl" shall mean the radical —C(=O)—, the term "sulfinyl" shall mean the radical —(S=O)—, the term "sulfonyl" shall mean the radical —S(=O)$_2$—, the term "carboxy" shall mean the radical —(C=)O— and —C(=O)OH, the term "amino" shall mean the radical —NH$_2$, the term "nitro" shall mean the radical —NO$_2$ and the term "cyano" shall mean the radical —CN.

The term "C$_{2-6}$-alkenyl" as used herein represents a branched or straight hydrocarbon group having from 2 to 6 carbon atoms and at least one double bond, e.g. C$_{2-6}$-alkenyl, C$_{3-6}$-alkenyl, and the like. Representative examples are ethenyl (or vinyl), propenyl (e.g., prop-1-enyl and prop-2-enyl), butadienyl (e.g., buta-1,3-dienyl), butenyl (e.g., but-1-en-1-yl and but-2-en-1-yl), pentenyl (e.g., pent-1-en-1-yl and pent-2-en-2-yl), hexenyl (e.g., hex-1-en-2-yl and hex-2-en-1-yl), 1-ethylprop-2-enyl, 1,1-(dimethyl)prop-2-enyl, 1-ethylbut-3-enyl, 1,1-(dimethyl)but-2-enyl, and the like.

Analogously, the term "C$_{3-8}$-alkenyl" as used herein represents a branched or straight hydrocarbon group having from 3 to 8 carbon atoms and at least one double bond, e.g. C$_{3-6}$-alkenyl, and the like. Representative examples are propenyl (e.g., prop-1-enyl and prop-2-enyl), butadienyl (e.g., buta-1,3-dienyl), butenyl (e.g., but-1-en-1-yl and but-2-en-1-yl), pentenyl (e.g., pent-1-en-1-yl and pent-2-en-2-yl), hexenyl (e.g., hex-1-en-2-yl and hex-2-en-1-yl), 1-ethylprop-2-enyl, 1,1-(dimethyl)prop-2-enyl, 1-ethylbut-3-enyl, 1,1-(dimethyl)but-2-enyl, and the like.

The term "C$_{1-6}$-alkoxy" as used herein refers to the radical C$_{1-6}$-alkyl-O—. Representative examples are methoxy, ethoxy, propoxy (e.g., 1-propoxy and 2-propoxy), butoxy (e.g., 1-butoxy, 2-butoxy and 2-methyl-2-propoxy), pentoxy (1-pentoxy and 2-pentoxy), hexoxy (1-hexoxy and 3-hexoxy), and the like.

The term "C$_{1-6}$-alkoxy-C$_{1-6}$-alkyl" as used herein refers to C$_{1-6}$-alkyl substituted with C$_{1-6}$-alkoxy at any carbon atom. Representative examples are methoxymethyl, ethoxymethyl, 2-methoxyethyl, 2-ethoxyethyl, 3-methoxyprop-1-yl, and the like.

The term "C$_{1-6}$-alkoxycarbonyl" as used herein refers to the radical C$_{1-6}$-alkoxy-C(=O)—. Representative examples are methoxycarbonyl, ethoxycarbonyl, 1-propoxycarbonyl, 2-propoxycarbonyl, 1-butoxycarbonyl, 2-butoxycarbonyl, 2-methyl-2-propoxycarbonyl, 3-methylbutoxycarbonyl, 1-hexoxycarbonyl, and the like.

The term "$C_{1-6}$-alkyl" as used herein represents a saturated, branched or straight hydrocarbon group having from 1 to 6 carbon atoms, e.g. $C_{1-3}$-alkyl, $C_{1-4}$-alkyl, $C_{2-6}$-alkyl, $C_{3-6}$-alkyl, and the like. Representative examples are methyl, ethyl, propyl (e.g., prop-1-yl and prop-2-yl (or isopropyl)), butyl (e.g., 2-methylprop-2-yl (or tert-butyl), but-1-yl and but-2-yl), pentyl (e.g., pent-1-yl, pent-2-yl and pent-3-yl), 2-methylbut-1-yl, 3-methylbut-1-yl, hexyl (e.g., hex-1-yl), heptyl (e.g., hept-1-yl) and the like.

Analogously, the term "$C_{1-8}$-alkyl" as used herein represents a saturated, branched or straight hydrocarbon group having from 1 to 8 carbon atoms, e.g. $C_{1-3}$-alkyl, $C_{1-4}$-alkyl, $C_{1-6}$-alkyl, $C_{2-6}$-alkyl, $C_{3-6}$-alkyl, $C_{1-8}$-alkyl, and the like. Representative examples are methyl, ethyl, propyl (e.g., prop-1-yl and prop-2-yl (or isopropyl)), butyl (e.g., 2-methylprop-2-yl (or tert-butyl), but-1-yl and but-2-yl), pentyl (e.g., pent-1-yl, pent-2-yl and pent-3-yl), 2-methylbut-1-yl, 3-methylbut-1-yl, hexyl (e.g., hex-1-yl), heptyl (e.g., hept-1-yl), octyl (e.g., oct-1-yl), and the like.

The term "$C_{1-6}$-alkylcarbonyl" as used herein refers to the radical $C_{1-6}$-alkyl-C(=O)—. Representative examples are acetyl (e.g., methylcarbonyl), propionyl (e.g, ethylcarbonyl), butanoyl (e.g., prop-1-ylcarbonyl and prop-2-ylcarbonyl), and the like.

The term "$C_{1-6}$-alkylcarbonylamino" as used herein, refers to the radical $C_{1-6}$-alkyl-C(=O)—NH—. Representative examples are acetylamino, propionylamino, pivaloylamino, valeroylamino, and the like.

The term "$C_{1-6}$-alkylcarbonylamino-$C_{1-6}$-alkyl" as used herein, refers to $C_{1-6}$-alkyl substituted at any carbon atom with $C_{1-6}$-alkylcarbonylamino. Representative examples are acetylaminomethyl, 1-(acetylamino)ethyl, propionylaminomethyl, and the like.

The term "$C_{1-6}$-alkylcarboxy" as used herein refers to the radical $C_{1-6}$-alkyl-C(=O)O—. Representative examples are methylcarboxy, ethylcarboxy, propylcarboxy (e.g., prop-1-ylcarboxy, prop-2-ylcarboxy), and the like.

The term "$C_{1-6}$-alkylsulfanyl" as used herein refers to the radical $C_{1-6}$-alkyl-S—. Representative examples are methylthio, ethylthio, propylthio (e.g., 1-propylthio, 2-propylthio and 3-propylthio), butylthio, pentylthio, hexylthio, and the like.

The term "$C_{1-6}$-alkylsulfinyl" as used herein refers to the radical $C_{1-6}$-alkyl-S(=O)—. Representative examples are methylsulfinyl, ethylsulfinyl, propylsulfinyl, butylsulfinyl, pentylsulfinyl, hexylsulfinyl, and the like.

The term "$C_{1-6}$-alkylsulfonyl" as used herein refers to the radical $C_{1-6}$-alkyl-S(=O)$_2$—. Representative examples are methylsulfonyl, ethylsulfonyl, propylsulfonyl, butylsulfonyl, pentylsulfonyl, hexylsulfonyl, and the like.

The term "$C_{3-8}$-alkynyl" as used herein represents a branched or straight hydrocarbon group having from 3 to 8 carbon atoms and at least one triple bond. Representative examples are propynyl (e.g., prop-1-ynyl and prop-2-ynyl), butynyl (e.g., but-1-ynyl and but-2-ynyl), pentynyl (e.g., pent-1-ynyl and pent-2-ynyl), hexynyl (e.g., hex-1-ynyl and hex-2-ynyl), 1-ethylprop-2-ynyl, 1,1-(dimethyl)prop-2-ynyl, 1-ethylbut-3-ynyl, 1,1-(dimethyl)but-2-ynyl, and the like.

The term "aryl" as used herein is intended to include monocyclic, bicyclic or polycyclic carbocyclic aromatic rings. Representative examples are phenyl, naphthyl (e.g., naphth-1-yl and naphth-2-yl), anthryl (e.g., anthr-1-yl and anthr-9-yl), phenanthryl (e.g., phenanthr-1-yl and phenanthr-9-yl), and the like. Aryl is also intended to include monocyclic, bicyclic or polycyclic carbocyclic aromatic rings substituted with carbocyclic aromatic rings. Representative examples are biphenyl (e.g., biphenyl-2-yl, biphenyl-3-yl and biphenyl-4-yl), phenylnaphthyl (e.g.1-phenylnaphth-2-yl and 2-phenylnaphth-1-yl), and the like. Aryl is also intended to include partially saturated bicyclic or polycyclic carbocyclic rings with at least one unsaturated moiety (e.g., a benzo moiety). Representative examples are, indanyl (e.g., indan-1-yl, indan-5-yl), indenyl (e.g., inden-1-yl and inden-5-yl), 1,2,3,4-tetrahydronaphthyl (e.g., 1,2,3,4-tetrahydronaphth-1-yl, 1,2,3,4-tetrahydronaphth-2-yl and 1,2,3,4-tetrahydronaphth-6-yl), 1,2-dihydronaphthyl (e.g., 1,2-dihydronaphth-1-yl, 1,2-dihydronaphth-4-yl and 1,2-dihydronaphth-6-yl), fluorenyl (e.g., fluoren-1-yl, fluoren-4-yl and fluoren-9-yl), and the like. Aryl is also intended to include partially saturated bicyclic or polycyclic carbocyclic aromatic rings containing one or two bridges. Representative examples are, benzonorbornyl (e.g., benzonorborn-3-yl and benzonorborn-6-yl), 1,4-ethano-1,2,3,4-tetrahydronapthyl (e.g., 1,4-ethano-1,2,3,4-tetrahydronapth-2-yl and 1,4-ethano-1,2,3,4-tetrahydronapth-10-yl), and the like. Aryl is also intended to include partially saturated bicyclic or polycyclic carbocyclic aromatic rings containing one or more spiro atoms. Representative examples are spiro[cyclopentane-1,1'-indane]-4-yl, spiro[cyclopentane-1,1'-indene]-4-yl, spiro[piperidine-4,1'-indane]-1-yl, spiro[piperidine-3,2'-indane]-1-yl, spiro[piperidine-4,2'-indane]-1-yl, spiro[piperidine-4,1'-indane]-3'-yl, spiro[pyrrolidine-3,2'-indane]-1-yl, spiro[pyrrolidine-3,1'-(3',4'-dihydronaphthalene)]-1-yl, spiro[piperidine-3,1'-(3',4'-dihydronaphthalene)]-1-yl, spiro[piperidine-4,1'-(3',4'-dihydronaphthalene)]-1-yl, spiro[imidazolidine-4,2'-indane]-1-yl, spiro[piperidine-4,1'-indene]-1-yl, and the like.

The term "aryl-$C_{1-6}$-alkoxycarbonyl" as used herein refers to the radical aryl-$C_{1-6}$-alkoxy-C(=O)—. Representative examples are benzyloxycarbonyl, phenylethoxycarbonyl (e.g., (2-phenylethoxy)carbonyl and (1-phenylethoxy)carbonyl), and the like.

The term "arylcarbonyl" as used herein, refers to the radical aryl-C(=O)—. Representative examples are benzoyl, naphthylcarbonyl, 4-phenylbenzoyl, anthrylcarbonyl, phenanthrylcarbonyl, and the like.

The term "arylcarbonylamino" as used herein, refers to the radical aryl-C(=O)—NH—. Representative examples are benzoylamino, naphthylcarbonylamino, 4-phenylbenzoylamino, and the like.

The term "arylcarbonylamino-$C_{1-6}$-alkyl" as used herein, refers to $C_{1-6}$-alkyl substituted at any carbon atom with arylcarbonylamino. Representative examples are benzoylaminomethyl, naphthylcarbonylaminomethyl, 2-(4-phenylbenzoylamino)ethyl, and the like.

The term "arylsulfonyl" as used herein refers to the radical aryl-S(=O)$_2$—. Representative examples are phenylsulfonyl, (4-methylphenyl)sulfonyl, (4-chlorophenyl)sulfonyl, naphthyl-sulfonyl, and the like.

The term "cyano-$C_{1-6}$-alkyl" as used herein refers to $C_{1-6}$-alkyl, substituted at any carbon atom(s) with cyano. Representative examples are cyanomethyl, 2-cyanoethyl, and the like.

The term "$C_{3-8}$-cycloalkenyl" as used herein represents a partially saturated monocyclic carbocyclic ring having from 3 to 8 carbon atoms and at least one double bond. Representative examples are cyclopropenyl, cyclobutenyl, cyclopentenyl, cyclohexenyl, cycloheptenyl, cyclooctenyl, cyclohex-1,3-dienyl, and the like.

Obviously, the term "$C_{3-8}$-cycloalkenyl-$C_{1-3}$-alkyl" is a combination of $C_{3-8}$-cycloalkenyl and $C_{1-3}$-alkyl. Representative examples are cyclopenten-1-ylmethyl, 3-(cyclohexen-1-yl)propyl, and the like.

The term "$C_{3-8}$-cycloalkyl" as used herein represents a saturated monocyclic carbocyclic ring having from 3 to 8 carbon atoms, e.g. $C_{3-6}$-alkyl, and the like. Representative examples are cyclopropyl, cyclobutyl, cyclopentyl, cyclohexyl, cycloheptyl, cyclooctyl, and the like. $C_{3-8}$-cycloalkyl is also intended to represent a saturated bicyclic carbocyclic ring having from 4 to 8 carbon atoms. Representative examples are decahydronaphthalenyl, bicycle-[3.3.0]octanyl, and the like. $C_{3-8}$-cycloalkyl is also intended to represent a saturated carbocyclic ring having from 3 to 8 carbon atoms and containing one or two carbon bridges. Representative examples are adamantyl, norbornanyl, nortricyclyl, bicyclo[3.2.1]octanyl, bicyclo-[2.2.2]octanyl, tricyclo[5.2.1.0/2,6]decanyl, bicyclo[2.2.1]heptyl, and the like. $C_{3-8}$-cycloalkyl is also intended to represent a saturated carbocyclic ring having from 3 to 8 carbon atoms and containing one or more spiro atoms. Representative examples are spiro[2.5]octanyl, spiro-[4.5]decanyl, and the like.

Obviously, the term "$C_{3-8}$-cycloalkyl-$C_{1-3}$-alkyl" is a combination of $C_{3-8}$-cycloalkyl and $C_{1-3}$-alkyl. Representative examples are cyclopropylmethyl, 2-cyclohexylethyl, 3-cyclopentyl-prop-1-yl, 1-cyclohexylethyl, adamantylmethyl, and the like.

Representative examples of "$C_{3-8}$-cycloalkylcarbonylamino-$C_{1-6}$-alkyl" as used herein is cyclopentylcarbonylaminomethyl, 3-(cyclohexylcarbonylamino)propyl, and the like.

The term "halo-$C_{1-6}$-alkyl" as used herein refers to $C_{1-6}$-alkyl, substituted one or more times at any carbon atom(s) with any halogen. Representative examples are trifluoromethyl, 2,2,2-trifluoroethyl, and the like.

The term "halo-$C_{1-6}$-alkoxy" as used herein refers to $C_{1-6}$-alkoxy, substituted one or more times at any carbon atom(s) with any halogen. Representative examples are trifluoromethoxy and 2,2,2-trifluoroethoxy, and the like.

The term "halogen" or "halo" means fluorine, chlorine, bromine or iodine. The term "heteroaryl" as used herein is intended to include monocyclic heterocyclic aromatic rings containing one or more heteroatoms selected from nitrogen, oxygen, sulfur, SO and $S(=O)_2$. Representative examples are pyrrolyl (e.g., pyrrol-1-yl, pyrrol-2-yl and pyrrol-3-yl), furanyl (e.g., furan-2-yl and furan-3-yl), thienyl (e.g., thien-2-yl and thien-3-yl), oxazolyl (e.g., oxazol-2-yl, oxazol-4-yl and oxazol-5-yl), thiazolyl (e.g., thiazol-2-yl, thiazol-4-yl and thiazol-5-yl), imidazolyl (e.g., imidazol-2-yl, imidazol-4-yl and imidazol-5-yl), pyrazolyl (e.g., pyrazol-1-yl, pyrazol-3-yl and pyrazol-5-yl), isoxazolyl (e.g., isoxazol-3-yl, isoxazol-4-yl and isoxazol-5-yl), isothiazolyl (e.g., isothiazol-3-yl, isothiazol-4-yl and isothiazol-5-yl), 1,2,3-triazolyl (e.g., 1,2,3-triazol-1-yl, 1,2,3-triazol-4-yl and 1,2,3-triazol-5-yl), 1,2,4-triazolyl (e.g., 1,2,4-triazol-1-yl, 1,2,4-triazol-3-yl and 1,2,4-triazol-5-yl), 1,2,3-oxadiazolyl (e.g., 1,2,3-oxadiazol-4-yl and 1,2,3-oxadiazol-5-yl), 1,2,4-oxadiazolyl (e.g., 1,2,4-oxadiazol-3-yl and 1,2,4-oxadiazol-5-yl), 1,2,5-oxadiazolyl (e.g., 1,2,5-oxadiazol-3-yl and 1,2,5-oxadiazol-4-yl), 1,3,4-oxadiazolyl (e.g., 1,3,4-oxadiazol-2-yl and 1,3,4-oxadiazol-5-yl), 1,2,3-thiadiazolyl (e.g., 1,2,3-thiadiazol-4-yl and 1,2,3-thiadiazol-5-yl), 1,2,4-thiadiazolyl (e.g., 1,2,4-thiadiazol-3-yl and 1,2,4-thiadiazol-5-yl), 1,2,5-thiadiazolyl (e.g., 1,2,5-thiadiazol-3-yl and 1,2,5-thiadiazol-4-yl), 1,3,4-thiadiazolyl (e.g., 1,3,4-thiadiazol-2-yl and 1,3,4-thiadiazol-5-yl), tetrazolyl (e.g., tetrazol-1-yl and tetrazol-5-yl), pyranyl (e.g., pyran-2-yl), pyridinyl (e.g., pyridine-2-yl, pyridine-3-yl and pyridine-4-yl), pyridazinyl (e.g., pyridazin-2-yl and pyridazin-3-yl), pyrimidinyl (e.g., pyrimidin-2-yl, pyrimidin-4-yl and pyrimidin-5-yl), pyrazinyl, 1,2,3-triazinyl, 1,2,4-triazinyl, 1,3,5-triazinyl, thiadiazinyl, azepinyl, azecinyl, and the like. Heteroaryl is also intended to include bicyclic heterocyclic aromatic rings containing one or more heteroatoms selected from nitrogen, oxygen, sulfur, $S(=O)$ and $S(=O)_2$. Representative examples are indolyl (e.g., indol-1-yl, indol-2-yl, indol-3-yl and indol-5-yl), isoindolyl, benzofuranyl (e.g., benzo[b]furan-2-yl, benzo[b]furan-3-yl, benzo[b]furan-5-yl, benzo[c]furan-2-yl, benzo[c]furan-3-yl and benzo[c]furan-5-yl), benzothienyl (e.g., benzo[b]thien-2-yl, benzo[b]thien-3-yl, benzo[b]thien-5-yl, benzo[c]thien-2-yl, benzo[c]-thien-3-yl and benzo[c]thien-5-yl), indazolyl (e.g., indazol-1-yl, indazol-3-yl and indazol-5-yl), indolizinyl (e.g., indolizin-1-yl and indolizin-3-yl), benzopyranyl (e.g., benzo[b]pyran-3-yl, benzo[b]pyran-6-yl, benzo[c]pyran-1-yl and benzo[c]pyran-7-yl), benzimidazolyl (e.g., benzimidazol-1-yl, benzimidazol-2-yl and benzimidazol-5-yl), benzothiazolyl (e.g., benzothiazol-2-yl and benzothiazol-5-yl), benzisothiazolyl, benzoxazolyl, benzisoxazolyl, benzoxazinyl, benzotriazolyl, naphthyridinyl (e.g., 1,8-naphthyridin-2-yl, 1,7-naphthyridin-2-yl and 1,6-naphthyridin-2-yl), phthalazinyl (e.g., phthalazin-1-yl and phthalazin-5-yl), pteridinyl, purinyl (e.g., purin-2-yl, purin-6-yl, purin-7-yl, purin-8-yl and purin-9-yl), quinazolinyl (e.g., quinazolin-2-yl, quinazolin-4-yl and quinazolin-6-yl), cinnolinyl, quinoliny (e.g., quinolin-2-yl, quinolin-3-yl, quinolin-4-yl and quinolin-6-yl), isoquinolinyl (e.g., isoquinolin-1-yl, isoquinolin-3-yl and isoquinolin-4-yl), quinoxalinyl (e.g., quinoxalin-2-yl and quinoxalin-5-yl), pyrrolopyridinyl (e.g., pyrrolo[2,3-b]pyridinyl, pyrrolo[2,3-c]pyridinyl and pyrrolo[3,2-c]pyridinyl), furopyridinyl (e.g., furo[2,3-b]pyridinyl, furo[2,3-c]pyridinyl and furo[3,2-c]pyridinyl), thienopyridinyl (e.g., thieno-[2,3-b]pyridinyl, thieno[2,3-c]pyridinyl and thieno[3,2-c]pyridinyl), imidazopyridinyl (e.g., imidazo[4,5-b]pyridinyl, imidazo[4,5-c]pyridinyl, imidazo[1,5-a]pyridinyl and imidazo[1,2-a]-pyridinyl), imidazopyrimidinyl (e.g., imidazo[1,2-a]pyrimidinyl and imidazo[3,4-a]pyrimidinyl), pyrazolopyridinyl (e.g., pyrazolo[3,4-b]pyridinyl, pyrazolo[3,4-c]pyridinyl and pyrazolo[1,5-a]-pyridinyl), pyrazolopyrimidinyl (e.g., pyrazolo[1,5-a]pyrimidinyl and pyrazolo[3,4-d]pyrimidinyl), thiazolopyridinyl (e.g., thiazolo[3,2-d]pyridinyl), thiazolopyrimidinyl (e.g., thiazolo[5,4-d]pyrimidinyl), imidazothiazolyl (e.g., imidazo[2,1-b]thiazolyl), triazolopyridinyl (e.g., triazolo-[4,5-b]pyridinyl), triazolopyrimidinyl (e.g., 8-azapurinyl), and the like. Heteroaryl is also intended to include polycyclic heterocyclic aromatic rings containing one or more heteroatoms selected from nitrogen, oxygen, sulfur, $S(=O)$ and $S(=O)_2$. Representative examples are carbazolyl (e.g., carbazol-2-yl, carbazol-3-yl, carbazol-9-yl), phenoxazinyl (e.g., phenoxazin-10-yl), phenazinyl (e.g., phenazin-5-yl), acridinyl (e.g., acridin-9-yl and acridin-10-yl), phenol-thiazinyl (e.g., phenothiazin-10-yl), carbolinyl (e.g., pyrido[3,4-b]indol-1-yl, pyrido[3,4-b]indol-3-yl), phenanthrolinyl (e.g., phenanthrolin-5-yl), and the like. Heteroaryl is also intended to include partially saturated monocyclic, bicyclic or polycyclic heterocyclic rings containing one or more heteroatoms selected from nitrogen, oxygen, sulfur, $S(=O)$ and $S(=O)_2$. Representative examples are pyrrolinyl, pyrazolinyl, imidazolinyl (e.g., 4,5-dihydroimidazol-2-yl and 4,5-dihydroimidazol-1-yl), indolinyl (e.g., 2,3-dihydroindol-1-yl and 2,3-dihydroindol-5-yl), dihydrobenzofuranyl (e.g., 2,3-dihydrobenzo[b]furan-2-yl and 2,3-dihydrobenzo[b]furan-4-yl), dihydrobenzothienyl (e.g., 2,3-dihydrobenzo[b]thien-2-yl and 2,3-dihydrobenzo[b]thien-5-yl), 4,5,6,7-tetrahydrobenzo[b]furan-5-yl), dihydrobenzopyranyl (e.g., 3,4-dihydrobenzo[b]pyran-3-yl, 3,4-dihydrobenzo[b]pyran-6-yl, 3,4-dihydrobenzo[c]pyran-1-yl and dihydrobenzo[c]pyran-7-yl), oxazolinyl (e.g., 4,5-dihydrooxazol-2-yl, 4,5-dihydrooxazol-4-yl and 4,5-dihydrooxazol-5-yl), isoxazolinyl, oxazepinyl, 2,4-dioxodihydropyrimidin-3-yl, tetrahydroindazolyl (e.g., 4,5,6,7-tetrahydroindazol-1-yl, 4,5,6,7-tetrahydroindazol-3-yl, 4,5,6,7-tetrahydroindazol-4-yl and 4,5,6,7-tetrahydroindazol-6-yl), tetrahydrobenzimidazolyl (e.g., 4,5,6,7-tetrahydrobenzimidazol-1-yl and 4,5,6,7-tetrahydrobenzimidazol-5-yl), tetrahydroimidazo[4,5-c]pyridyl (e.g., 4,5,6,7-tetrahydroimidazo[4,5-c]pyrid-1-yl, 4,5,6,7-tetrahydroimidazo[4,5-c]pyrid-5-yl and 4,5,6,7-tetrahydroimidazo[4,5-c]pyrid-6-yl), tetrahydroquinolinyl (e.g., 1,2,3,4-tetrahydroquinolinyl and 5,6,7,8-tetrahydroquinolinyl), tetrahydroisoquinolinyl (e.g., 1,2,3,4-tetrahydroisoquinolinyl and 5,6,7,8-tetrahydroisoquinolinyl), tetrahydroquinoxalinyl (e.g., 1,2,3,4-tetrahydroquinoxalinyl and 5,6,7,8-tetrahydroquinoxalinyl), 2,3-dihydrobenzo[1,4]dioxin-6-yl, 2,3-dihydrobenzo[1,4]dioxin-5-yl, 2,3-dihydrobenzo[1,4]dioxin-2-yl, benzo[1,3]dioxol-4-yl, benzo-[1,3]dioxol-5-yl, benzo[1,3]dioxol-2-yl, 3,4-dihydro-2H-benzo[1,4]oxazin-7-yl, 4-methyl-3,4-dihydro-2H-benzo[1,4]oxazin-7-yl and the like. Heteroaryl is also intended to include partially saturated bicyclic or polycyclic heterocyclic rings containing one or more spiro atoms. Representative examples are spiro[isoquinoline-3,1'-cyclohexan]-1-yl, spiro[piperidine-4,1'-benzo-[c]thiophen]-1-yl, spiro[piperidine-4,1'-benzo[c]furan]-1-yl, spiro[piperidine-4,3'-benzo[b]-furan]-1-yl, spiro[piperidine-4,3'-coumarin]-1-yl, and the like.

The term "heteroarylcarbonyl" as used herein refers to the radical heteroaryl-C(=O)—. Representative examples are pyridinylcarbonyl (e.g., pyridin-2-ylcarbonyl and pyridin-4-ylcarbonyl), quinolinylcarbonyl (e.g., 2-(quinolin-2-yl)carbonyl and 1-(quinolin-2-yl)carbonyl), imidazolylcarbonyl (e.g., imidazol-2-ylcarbonyl and imidazol-5-ylcarbonyl), and the like.

The term "heteroarylcarbonylamino" as used herein, refers to the radical heteroaryl-C(=O)—NH—. Representative examples are pyridinylcarbonylamino (e.g., pyridin-2-ylcarbonylamino and pyridin-4-ylcarbonylamino), quinolinylcarbonylamino (e.g., 2-(quinolin-2-yl)-carbonylamino and 1-(quinolin-2-yl)carbonylamino), and the like.

The term "heteroarylcarbonyl-$C_{1-6}$-alkyl" as used herein, refers to $C_{1-6}$-alkyl substituted at any carbon atom with heteroarylcarbonylamino. Representative examples are pyridinylcarbonylaminomethyl (e.g., pyridin-2-ylcarbonylaminomethyl and pyridin-4-yl-carbonylaminomethyl), 2-(quinolinylcarbonylamino)ethyl (e.g., 2-(2-(quinolin-2-yl)carbonylamino)ethyl and 2-(1-(quinolin-2-yl)carbonylamino)ethyl), and the like.

The term "heterocyclyl" as used herein represents a saturated 3 to 8 membered monocyclic ring, containing one or more heteroatoms selected from nitrogen, oxygen, sulfur, S(=O) and S(=O)$_2$. Representative examples are aziridinyl (e.g., aziridin-1-yl), azetidinyl (e.g., azetidin-1-yl and azetidin-3-yl), oxetanyl, pyrrolidinyl (e.g., pyrrolidin-1-yl, pyrrolidin-2-yl and pyrrolidin-3-yl), 2-oxopyrrolidin-1-yl, 2,5-dioxopyrrolidin-1-yl, imidazolidinyl (e.g., imidazolidin-1-yl, imidazolidin-2-yl and imidazolidin-4-yl), 2,4-dioxo-imidazolidin-3-yl, 2,4-dioxo-1-methylimidazolidin-3-yl, 2,4-dioxo-1,5,5-trimethylimidazolidin-3-yl, 2,4-dioxo-5,5-dimethylimidazolidin-3-yl, oxazolidinyl (e.g., oxazolidin-2-yl, oxazolidin-3-yl and oxazolidin-4-yl), 2-oxo-oxazolidin-3-yl, thiazolidinyl (e.g., thiazolidin-2-yl, thiazolidin-3-yl and thiazolidin-4-yl), 2,4-dioxo-thiazolidin-3-yl, isothiazolidinyl, 1,1-dioxo-isothiazolidin-2-yl, 1,1-dioxo-[1,2,5]thiadiazolidin-2-yl, piperidinyl (e.g., piperidin-1-yl, piperidin-2-yl, piperidin-3-yl and piperidin-4-yl), 2-oxopiperidin-1-yl, 2,6-dioxopiperidin-1-yl, homopiperidinyl (e.g., homopiperidin-1-yl, homopiperidin-2-yl, homopiperidin-3-yl and homopiperidin-4-yl), piperazinyl (e.g., piperazin-1-yl and piperazin-2-yl), morpholinyl (e.g., morpholin-2-yl, morpholin-3-yl and morpholin-4-yl), 2-oxo-[1,3]oxazinan-3-yl, thiomorpholinyl (e.g., thiomorpholin-2-yl, thiomorpholin-3-yl and thiomorpholin-4-yl), 1-oxo-thiomorpholinyl, 1,1-dioxo-thiomorpholinyl, tetrahydrofuranyl (e.g., tetrahydrofuran-2-yl and tetrahydrofuran-3-yl), tetrahydrothienyl, tetrahydro-1,1-dioxothienyl, tetrahydropyranyl (e.g., 2-tetrahydropyranyl), tetrahydrothiopyranyl (e.g., 2-tetrahydrothiopyranyl), 1,4-dioxanyl, 1,3-dioxanyl, and the like. Heterocyclyl is also intended to represent a saturated 6 to 12 membered bicyclic ring containing one or more heteroatoms selected from nitrogen, oxygen, sulfur, S(=O) and S(=O)$_2$. Representative examples are octahydroindolyl (e.g., octahydroindol-1-yl, octahydroindol-2-yl, octahydroindol-3-yl and octahydroindol-5-yl), decahydroquinolinyl (e.g., decahydroquinolin-1-yl, decahydroquinolin-2-yl, decahydroquinolin-3-yl, decahydroquinolin-4-yl and decahydroquinolin-6-yl), decahydroquinoxalinyl (e.g., decahydroquinoxalin-1-yl, decahydroquinoxalin-2-yl and decahydroquinoxalin-6-yl) and the like. Heterocyclyl is also intended to represent a saturated 6 to 12 membered ring containing one or more heteroatoms selected from nitrogen, oxygen, sulfur, S(=O) and S(=O)$_2$ and having one or two bridges. Representative examples are 3-azabicyclo[3.2.2]nonyl, 2-azabicyclo-[2.2.1]heptyl, 3-azabicyclo[3.1.0]hexyl, 2,5-diazabicyclo[2.2.1]heptyl, atropinyl, tropinyl, quinuclidinyl, 1,4-diazabicyclo[2.2.2]octanyl, and the like. Heterocyclyl is also intended to represent a 6 to 12 membered saturated ring containing one or more heteroatoms selected from nitrogen, oxygen, sulfur, S(=O) and S(=O)$_2$ and containing one or more spiro atoms. Representative examples are 1,4-dioxaspiro[4.5]decanyl (e.g., 1,4-dioxaspiro[4.5]decan-2-yl and 1,4-dioxaspiro[4.5]decan-7-yl), 1,4-dioxa-8-azaspiro[4.5]decanyl (e.g., 1,4-dioxa-8-azaspiro-[4.5]decan-2-yl and 1,4-dioxa-8-azaspiro[4.5]decan-8-yl), 8-azaspiro[4.5]decanyl (e.g., 8-azaspiro[4.5]decan-1-yl and 8-azaspiro[4.5]decan-8-yl), 2-azaspiro[5.5]undecanyl (e.g., 2-azaspiro[5.5]undecan-2-yl), 2,8-diazaspiro[4.5]decanyl (e.g., 2,8-diazaspiro[4.5]decan-2-yl and 2,8-diazaspiro[4.5]decan-8-yl), 2,8-diazaspiro[5.5]undecanyl (e.g., 2,8-diazaspiro[5.5]undecan-2-yl), 1,3,8-triazaspiro[4.5]decanyl (e.g., 1,3,8-triazaspiro[4.5]decan-1-yl and 1,3,8-triazaspiro[4.5]decan-3-yl, 1,3,8-triazaspiro[4.5]decan-8-yl), and the like.

The term "heterocyclyl-$C_{1-6}$-alkoxy" as used herein refers to the radical heterocyclyl-$C_{1-6}$-alkoxy. Representative examples are piperidin-1-ylmethoxy, 2-(piperidin-1-yl)ethoxy, 3-(piperidin-1-yl)prop-3-oxy, piperazin-1-ylmethoxy, 2-(piperazin-1-yl)ethoxy, 3-(piperazin-1-yl)-prop-3-oxy, morpholin-4-ylmethoxy, 2-(morpholin-4-yl)ethoxy, 3-(morpholin-4-yl)prop-3-oxy, and the like.

The term "heterocyclyl-$C_{1-6}$-alkyl" as used herein refers to the radical heterocyclyl-$C_{1-6}$-alkyl. Representative examples are piperidin-1-ylmethyl, 2-(piperidin-1-yl)ethyl, 3-hydroxy-3-(piperidin-1-yl)propyl, piperazin-1-ylmethyl, 2-(piperazin-1-yl)ethyl, 3-hydroxy-3-(piperazin-1-yl)propyl, morpholin-4-ylmethyl, 2-(morpholin-4-yl)ethyl, 3-hydroxy-3-(morpholin-4-yl)propyl, and the like.

The term "heterocyclylcarbonyl" as used herein refers to the radical heterocyclyl-C(=O)—. Representative examples are piperidinylcarbonyl (e.g., piperidin-2-ylcarbonyl, piperidin-3-ylcarbonyl and piperidin-4-ylcarbonyl), piperazinylcarbonyl (e.g., piperazin-1-ylcarbonyl and piperazin-2-ylcarbonyl), and the like.

The term "hydroxy-$C_{1-6}$-alkyl" as used herein refers to $C_{1-6}$-alkyl substituted one or more times at any carbon atom(s) with hydroxyl. Representative examples are hydroxymethyl, hydoxyethyl (e.g., 1-hydroxyethyl and 2-hydroxyethyl), and the like.

The term "N—($C_{1-6}$-alkylcarbonyl)-N—($C_{1-6}$-alkyl)amino" as used herein is an amino group with two substituents, i.e., a $C_{1-6}$-alkylcarbonyl group and an $C_{1-6}$-alkyl group. Analogously, the following terms cover groups wherein an amino group has two substituents: N—($C_{3-8}$-cycloalkylcarbonyl)-N—($C_{1-6}$-alkyl)amino and N—($C_{3-8}$-cycloalkyl-$C_{1-6}$-alkylcarbonyl)-N—($C_{1-6}$-alkyl)amino. Analogously, the following terms cover groups wherein there are two substituents on the nitrogen atom in the amino-$C_{1-6}$-alkyl moiety: N—($C_{1-6}$-alkylcarbonyl)-N—($C_{1-6}$-alkyl)-amino-$C_{1-6}$-alkyl, N—($C_{3-8}$-cycloalkylcarbonyl)-N—($C_{1-6}$-alkyl)amino-$C_{1-6}$-alkyl and N—($C_{3-8}$-cycloalkyl-$C_{1-6}$-alkylcarbonyl)-N—($C_{1-6}$-alkyl)amino-$C_{1-6}$-alkyl. Representative examples are N-cyclohexylcarbonyl-N-methylamino, 2-(N-cyclopentylcarbonyl-N-methylamino)ethyl and the like.

The term "bridge" as used herein represents a connection in a saturated or partly saturated ring between two atoms of such ring that are not neighbours through a chain of 1 to 4 atoms selected from carbon, nitrogen, oxygen and sulphur. Representative examples of such connecting chains are —$CH_2$—, —$CH_2CH_2$—, —$CH_2NHCH_2$—, —$CH_2CH_2CH_2$—, —$CH_2OCH_2$—, and the like.

The term "spiro atom" as used herein represents a carbon atom in a saturated or partly saturated ring that connects both ends of a chain of 3 to 8 atoms selected from carbon, nitrogen, oxygen and sulfur. Representative examples are —$(CH_2)_5$—, —$(CH_2)_3$—, —$(CH_2)_4$—, —$CH_2NHCH_2CH_2$—, —$CH_2CH_2NHCH_2CH_2$—, —$CH_2NHCH_2CH_2CH_2$—, —$CH_2CH_2OCH_2$—, —$OCH_2CH_2O$—, and the like.

The term "optionally substituted" as used herein means that the groups in question are either unsubstituted or substituted with one or more of the substituents specified. When the group(s) in question are substituted with more than one substituent, the substituents may be the same or different.

Certain of the defined terms may occur more than once in the structural formulae, and upon such occurrence each term shall be defined independently of the other.

Certain of the defined terms may occur in combinations, and it is to be understood that the first mentioned radical is a substituent on the subsequently mentioned radical, where the point of substitution, i.e., the point of attachment to another part of the molecule, is on the last mentioned of the radicals.

The term "solvate" as used herein is a complex of defined stoichiometry formed by a solute (in casu, a compound according to the present invention) and a solvent. Solvents are those commonly used in the pharmaceutical art, by way of example, water, ethanol, acetic acid, and the like. The term "hydrate" refers to the complex where the solvent molecule is water.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "prodrug" as used herein includes biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

The term "biohydrolyzable ester" as used herein is an ester of a drug substance (in this invention, a compound of formula I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_{1-4}$), lower acyloxyalkyl esters, lower alkoxyacyloxyalkyl esters, alkoxyacyloxy esters, alkyl acylamino alkyl esters, and choline esters.

The term "biohydrolyzable amide" as used herein is an amide of a drug substance (in this invention, a compound of general formula I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, a-amino acid amides, alkoxyacyl amides, and alkylaminoalkylcarbonyl amides.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "metabolite" as used herein is any intermediate or product resulting from metabolism.

The term "metabolism" as used herein refer to the biotransformation of a drug substance (in this invention, a compound of general formula I) administered to a patient.

The representative examples mentioned above are specific embodiments of this invention.

In the examples below, the following terms are intended to have the following, general meanings: d is day(s), g is gram(s), h is hour(s), Hz is hertz, kD is kiloDalton(s), L is liter(s), M is molar, mbar is millibar, mg is milligram(s), min is minute(s), mL is milliliter(s), mM is millimolar, mmol is millimole(s), mol is mole(s), N is normal, ppm is parts per million, psi is pounds per square inch, APCI is atmospheric pressure chemical ionization, ESI is electrospray ionization, I.v. is intravenous, m/z is mass to charge ratio, mp/Mp is melting point, MS is mass spectrometry, HPLC is high pressure liquid chromatography, RP is reverse phase, HPLC-MS is high pressure liquid chromatography-mass spectrometry, NMR is nuclear magnetic resonance spectroscopy, p.o. is per oral, $R_f$ is relative TLC mobility, rt is room temperature s.c. is subcutaneous, TLC is thin layer chromatography, $t_r$ is retention time, BOP is (1-benzotriazolyloxy)tris(dimethylamino) phosphoniumhexafluorophosphate, CDI is carbonyl-diimidazole, DCM is dichloromethane, $CH_2Cl_2$ is methylene chloride, DIBAL-H is diisobutyl-aluminiumhydride, DBU is 1,8-diazabicyclo[5.4.0]undec-7-ene, DEAD is diethyl azodicarboxylate, DIC is 1,3-diisopropylcarbodiimide, DIPEA is N,N-diisopropylethylamine, DMA is N,N-dimethylacetamide, DMF is N,N-dimethylformamide, DMPU is N,N'-dimethylpropylene-urea, 1,3-dimethyl-2-oxohexahydropyrimidine, DMSO is dimethylsulfoxide, EDAC is 1-ethyl-3-(3-dimethylaminopropyl)carbodiimide hydrochloride, $Et_2O$ is diethyl ether, EtOAc is ethyl acetate, HMPA is hexamethylphosphoric acid triamide, HOAt is 1-hydroxy-7-azabenzotriazole, HOBt is 1-hydroxybenzotriazole, LAH is lithium aluminium hydride ($LiAlH_4$), LDA is lithium diisopropylamide, MeCN is acetonitrile, MeOH is methanol, NMM is N-methylmorpholine (4-methylmorpholine), NMP is N-methylpyrrolidin-2-one, TEA is triethylamine, TFA is trifluoroacetic acid, THF is tetrahydrofuran, THP is tetrahydropyranyl, TTFH is fluoro-N,N,N',N'-tetramethylformamidinium hexafluorophosphate, 9-BBN is 9-borabicyclo[3.3.1]nonane, $CDCl_3$ is deuterio chloroform, $CD_3OD$ is tetradeuterio methanol and DMSO-$d_6$ is hexadeuterio dimethylsulfoxide.

SUMMARY OF THIS INVENTION

The invention relates to compounds of the general formula I specified in the claims below. The compounds of this invention differ structurally from the known compounds.

The invention also relates to the use of said compounds in therapy, and in particular to pharmaceutical compositions comprising said compounds.

In another embodiment, the invention relates to methods of treatment, the method comprising administering to a subject in need thereof an effective amount of one or more compounds according to formula I.

In a still further embodiment, the invention relates to the use of compounds according to formula I in the manufacture of medicaments.

DETAILED DESCRIPTION OF THIS INVENTION

Due to their interaction with the histamine H3 receptor, the compounds of this invention as defined in the claims below and elsewhere in this specification are useful in the treatment of a wide range of conditions and disorders in which an interaction with the histamine H3 receptor is beneficial. Thus, the compounds may find use, e.g., in the treatment of diseases of the central nervous system, the peripheral nervous system, the cardiovascular system, the pulmonary system, the gastrointestinal system and the endocrinological system.

In an embodiment, this invention relates to a compound of the general formula I.

PREFERRED FEATURES OF THIS INVENTION

Preferred features of this invention are the following:
1) A compound of the general formula I

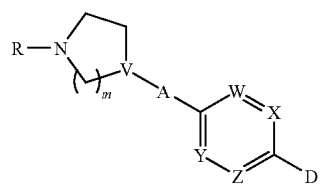

wherein W, X, Y, Z independent of each other is a moiety of the formula —C($R^1$)= or —N= (i.e. nitrogen), with the proviso that one to two (but not more) of the symbols W, X, Y or Z must be the moiety —N=; $R^1$ is hydrogen or $C_{1-3}$ alkyl, V is –N< or —CH<, A is a bond or an alkylene linker —$(CH_2)_n$—, where n is 1 to 3, with the proviso that when A is a bond, V must be —CH<, R is ethyl, propyl, a branched $C_{3-6}$ alkyl or a cyclic $C_{3-8}$ alkyl, m is 1, 2 or 3, n is 1, 2 or 3, D is heteroaryl optionally substituted with halogen, hydroxy, cyano, $C_{1-6}$-alkyl, $C_{3-8}$-cycloalkyl, $C_{1-6}$-alkoxy, —$(CH_2)_o$—(C=O)$_p$—$NR^2R^3$, or D is aryl optionally substituted with one or more of the groups independently selected from hydrogen, halogen, hydroxy, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy, $C_{1-6}$-alkylsulfonyl, $C_{1-6}$-alkylsulfinyl, heterocyclyl, heterocyclyl-$C_{1-6}$-alkyl, heterocyclyl-$C_{1-6}$-alkoxy, heterocyclylcarbonyl, $C_{1-6}$-alkylcarbonyl, $C_{1-6}$-alkoxycarbonyl, $C_{1-6}$-alkylcarboxy, cyano-$C_{1-6}$-alkyl, hydroxy-$C_{1-6}$-alkyl, $C_{1-6}$-alkoxy-$C_{1-6}$-alkyl, $C_{1-6}$-alkylcarbonylamino, $C_{1-6}$-alkylcarbonylamino-$C_{1-6}$-alkyl, arylcarbonylamino, arylcarbonylamino-$C_{1-6}$-alkyl, heteroarylcarbonylamino or heteroarylcarbonylamino-$C_{1-6}$-alkyl, —$(CH_2)_o$—(C=O)$_p$—$NR^2R^3$, o is 0 (zero), 1, 2 or 3, p is 0 (zero) or 1, and $R^2$ and $R^3$ independently are hydrogen, $C_{1-6}$-alkyl or $C_{3-8}$-cycloalkyl; or $R^2$ and $R^3$ can together with the attached nitrogen form a heterocyclyl group, or salts or solvates thereof.
2) Compounds according to clause 1, wherein R is isopropyl, cyclobutyl, cyclopentyl or 3-pentyl.
3) The compound of clause 1 or 2, wherein R is isopropyl or cyclobutyl.
4) The compound of any of the preceding clauses to the extend possible, wherein m is 1.
5) The compound of any of the preceding clauses to the extend possible, wherein m is 2.
6) The compound of any of the preceding clauses to the extend possible, wherein V is >CH—.
7) The compound of any of the preceding clauses to the extend possible, wherein V is >N—.
8) The compound of any of the preceding clauses to the extend possible, wherein A is a bond or methylene (—$CH_2$—).
9) The compound of any of the preceding clauses to the extend possible, wherein A is methylene.
10) The compound of any of the preceding clauses to the extend possible, wherein only one of W, X, Y and Z is nitrogen and the other three are each —CH=.

11) The compound of any of the preceding clauses to the extend possible, wherein two of W, X, Y and Z are each nitrogen and the other two are each —CH=.
12) The compound of any of the preceding clauses to the extend possible, wherein W, X, Y and Z are —CH=, =CH—, =N— and —CH=, respectively.
13) The compound of any of the preceding clauses to the extend possible, wherein W, X, Y and Z are —CH=, =CH—, =CH— and —N=, respectively.
14) The compound of any of the preceding clauses to the extend possible, wherein W, X, Y and Z are —CH=, =CH—, =N— and —N=, respectively.
15) The compound of any of the preceding clauses to the extend possible, wherein D is phenyl substituted by one or two substituents selected from the group consisting of formyl, acetyl, anilino, amino, cyano, diisopropylcarbonyl, ethylsulfonyl, flouro, methylcarbonylamino, 4-methylpiperazinylcarbonyl, morpholin-4-yl, morpholin-4-ylcarbonyl, morpholin-4-ylsulfonyl, N,N-diethylaminocarbonyl, N,N-diethylaminomethyl, N,N-dimethylaminocarbonyl, N,N-dimethylaminomethyl, N,N-dimethylaminosulfonyl, piperidinylsulfonyl, pyrrolidinylcarbonyl, pyrrolidinylethyl, pyrrolidinylmethyl or, if substituted on two different carbon atoms in the phenyl ring, methylenedioxy.
16) The compound of any of the preceding clauses to the extend possible, wherein D is phenyl substituted by one or two substituents selected from the group consisting of formyl, amino, cyano, ethylsulfonyl, flouro, methylcarbonylamino, 4-methylpiperazinylcarbonyl, morpholin-4-yl, morpholin-4-ylcarbonyl, morpholin-4-ylmethyl, morpholin-4-ylsulfonyl, N,N-diethylaminocarbonyl, N,N-diethylaminomethyl, N,N-dimethylaminocarbonyl, N,N-dimethylaminomethyl, N,N-dimethylaminosulfonyl, piperidinylsulfonyl, pyrrolidinylcarbonyl, pyrrolidinylethyl, pyrrolidinylmethyl or, if substituted on two different carbon atoms in the phenyl ring, methylenedioxy.
17) The compound of any of the preceding clauses to the extend possible, wherein D is pyridyl substituted by a methyl or a oxo-group.
18) The compound of any of the preceding clauses to the extend possible, wherein D is 4-N-acetylphenyl, 4-formylphenyl, 4-anilinophenyl, 4-aminophenyl, 1,3-benzodioxol-5-yl, 4-carboxyphenyl, 4-cyanophenyl, 4-(diisopropylcarbonyl)phenyl, 4-(N,N-diethylaminocarbonyl)phenyl, 4-(N,N-diethylaminomethyl)phenyl, 3-(N,N-dimethylaminocarbonyl)-phenyl, 4-(N,N-dimethylaminocarbonyl)phenyl, 4-(N,N-dimethylaminomethyl)phenyl, 4-(N,N-dimethylaminosulfonyl)phenyl, 4-ethylsulfonylphenyl, 4-(methylcarbonylamino)-phenyl, 1-methyl-2-oxopyridin-5-yl, 4-(4-methylpiperzin-1-ylcarbonyl)phenyl, 2-methylpyridin-4-yl, 4-morpholin-4-ylphenyl, 4-(morpholin-4-ylcarbonyl)phenyl, 4-(morpholin-4-ylmethyl)phenyl, 4-(morpholin-4-ylsulfonyl)phenyl, 1-methyl-2-oxo-1,2-dihydropyrid-5-yl, 4-(piperidin-1-ylsulfonyl)phenyl, 4-(piperidin-1-ylcarbonyl)phenyl, 4-(pyrrolidin-1-ylcarbonyl)-3-fluorophenyl, 4-(pyrrolidin-1-ylcarbonyl)phenyl, 4-(pyrrolidin-1-ylethyl)phenyl or 4-(pyrrolidin-1-ylmethyl)phenyl.
19) The compound of any of the preceding clauses to the extend possible, wherein D is 4-formylphenyl, 4-aminophenyl, 1,3-benzodioxol-5-yl, 4-carboxyphenyl, 4-cyanophenyl, 4-(N,N-diethylaminocarbonyl)phenyl, 4-(N,N-diethylaminomethyl)phenyl, 3-(N,N-dimethylaminocarbonyl)phenyl, 4-(N,N-dimethylaminocarbonyl)phenyl, 4-(N,N-dimethylaminomethyl)phenyl, 4-(N,N-dimethylaminosulfonyl)phenyl, 4-ethylsulfonylphenyl, 4-(methylcarbonylamino)phenyl, 1-methyl-2-oxopyridin-5-yl, 4-(4-methylpiperzin-1-ylcarbonyl)-phenyl, 2-methylpyridin-4-yl, 4-morpholin-4-ylphenyl, 4-(morpholin-4-ylcarbonyl)phenyl, 4-(morpholin-4-ylsulfonyl)phenyl, 1-methyl-2-oxo-1,2-dihydropyrid-5-yl, 4-(piperid-1-ylsulfonyl)phenyl, 4-(piperid-1-ycarbonyl)phenyl, 4-(pyrrolidin-1-ylcarbonyl)-3-fluorophenyl, 4-(pyrrolidin-1-ylcarbonyl)phenyl, 4-(pyrrolidin-1-ylethyl)phenyl or 4-(pyrrolidin-1-ylmethyl)phenyl.
20) The compound of any of the preceding clauses to the extend possible, wherein D is 2-methyl-4-pyridyl, N-methyl-2-oxo-5-pyridyl-, 5-methoxy-3-pyridyl, or 3,4-methylenedioxy-phenyl.
21) A use of a compound of any of the above clauses as medicament.
22) A use of a compound of any of the above clauses as medicament for curing or preventing any one of the diseases mentioned herein.

Examples of specific compounds of formula I are:
1) 5-1,3-benzodioxol-5-yl-1'-isopropyl-1',2',3',4',5',6'-hexahydro-2,4'-bipyridinyl;
2) 1'-isopropyl-5-(4-morpholin-4-ylphenyl)-1',2',3',4',5',6'-hexahydro-[2,4']bipyridinyl;
3) 1-isopropyl-2"-methyl-1,2,3,4,5,6-hexahydro-[4,2';5',4"]terpyridine;
4) 5-(4-ethanesulfonylphenyl)-1'-isopropyl-1',2',3',4',5',6'-hexahydro-[2,4']bipyridinyl;
5) 4-(1'-isopropyl-1',2',3',4',5',6'-hexahydro-[2,4']bipyridinyl-5-yl)-N,N-dimethylbenzamide;
6) [2-fluoro-4-(1'-isopropyl-1',2',3',4',5',6'-hexahydro-[2,4']bipyridinyl-5-yl)phenyl]pyrrolidin-1-ylmethanone;
7) 3-(1'-isopropyl-1',2',3',4',5',6'-hexahydro-[2,4']bipyridinyl-5-yl)-N,N-dimethylbenzamide;
8) N,N-diethyl-4-(1'-isopropyl-1',2',3',4',5',6'-hexahydro-[2,4']bipyridinyl-5-yl)benzamide;
9) [4-(1'-isopropyl-1',2',3',4',5',6'-hexahydro-[2,4']bipyridinyl-5-yl)phenyl]-(4-methylpiperazin-1-yl)methanone;
10) 1"-isopropyl-1-methyl-1",2",3",4",5",6"-hexahydro-1H-[3,3';6',4"]terpyridin-6-one;
11) [4-(1'-isopropyl-1',2',3',4',5',6'-hexahydro-[2,4']bipyridinyl-5-yl)phenyl]pyrrolidin-1-ylmethanone;
12) 1'-isopropyl-5-[4-(piperidine-1-sulfonyl)phenyl]-1',2',3',4',5',6'-hexahydro-[2,4']bipyridinyl;
13) 3-(4-ethanesulfonylphenyl)-6-(1-isopropylpiperidin-4-yl)pyridazine;
14) [4-(1'-cyclobutyl-1',2',3',4',5',6'-hexahydro-[2,4']bipyridinyl-5-yl)phenyl]-(4-methylpiperazin-1-yl)methanone;
15) 4-(1'-cyclobutyl-1',2',3',4',5',6'-hexahydro-[2,4']bipyridinyl-5-yl)-N,N-dimethylbenzamide;
16) 4-(1'-cyclobutyl-1',2',3',4',5',6'-hexahydro-[2,4']bipyridinyl-5-yl)-N,N-diethylbenzamide;
17) [4-(1'-cyclobutyl-1',2',3',4',5',6'-hexahydro-[2,4']bipyridinyl-5-yl)phenyl]pyrrolidin-1-ylmethanone;
18) 4-[6-(1-isopropylpiperidin-4-yl)pyridazin-3-yl]-N,N-dimethylbenzenesulfonamide;
19) 3-(1-isopropylpiperidin-4-yl)-6-(2-methylpyridin-4-yl)pyridazine;
20) 5-[6-(1-isopropylpiperidin-4-yl)pyridazin-3-yl]-1-methyl-1H-pyridin-2-one;
21) 1'-cyclobutyl-5-(4-ethanesulfonylphenyl)-1',2',3',4',5',6'-hexahydro-[2,4']bipyridinyl;
22) 4-(1'-cyclobutyl-1',2',3',4',5',6'-hexahydro-[2,4']bipyridinyl-5-yl)-N,N-dimethylbenzene-sulfonamide;
23) 1-cyclobutyl-2"-methyl-1,2,3,4,5,6-hexahydro-[4,2';5',4"]terpyridine;

24) [4-(1'-cyclobutyl-1',2',3',4',5',6'-hexahydro-[2,4']bipyridinyl-5-yl)benzyl]pipethylamine;
25) 1'-cyclobutyl-5-(4-pyrrolidin-1-ylmethylphenyl)-1',2',3',4',5',6'-hexahydro-[2,4']bipyridinyl;
26) [4-(1'-cyclobutyl-1',2',3',4',5',6'-hexahydro-[2,4']bipyridinyl-5-yl)benzyl]dimethylamine;
27) {4-[6-(1-cyclobutylpiperidin-4-ylmethyl)pyridin-3-yl]phenyl}-(4-methylpiperazin-1-yl)-methanone;
28) 4-[6-(1-cyclobutylpiperidin-4-ylmethyl)pyridin-3-yl]-N,N-dimethylbenzenesulfonamide;
29) 6-(1-cyclobutylpiperidin-4-ylmethyl)-2'-methyl-[3,4']bipyridinyl;
30) 4-[6-(1-cyclobutylpiperidin-4-ylmethyl)pyridin-3-yl]-N,N-dimethylbenzamide;
31) {4-[6-(1-cyclobutylpiperidin-4-ylmethyl)pyridin-3-yl]phenyl}morpholin-4-ylmethanone;
32) {4-[6-(1-cyclobutylpiperidin-4-ylmethyl)pyridin-3-yl]benzyl}dimethylamine;
33) 2-(1-cyclobutylpiperidin-4-ylmethyl)-5-(4-ethanesulfonylphenyl)pyridine;
34) N-{4-[5-(4-isopropylpiperazin-1-ylmethyl)pyridin-2-yl]phenyl}acetamide;
35) 4-[5-(4-isopropylpiperazin-1-ylmethyl)pyridin-2-yl]phenylamine;
36) 1-[6-(4-ethanesulfonylphenyl)pyridin-3-ylmethyl]-4-isopropylpiperazine;
37) 1-isopropyl-4-{6-[4-(piperidine-1-sulfonyl)phenyl]pyridin-3-ylmethyl}piperazine;
38) 5-(4-isopropylpiperazin-1-ylmethyl)-2'-methyl-[2,4']bipyridinyl;
39) 1-(6-1,3-benzodioxol-5-ylpyridin-3-ylmethyl)-4-isopropylpiperazine;
40) 4-{4-[5-(4-isopropylpiperazin-1-ylmethyl)pyridin-2-yl]phenyl}morpholine;
41) 4-[6-(4-cyclobutylpiperazin-1-ylmethyl)pyridin-3-yl]-N,N-dimethylbenzamide;
42) 4-[6-(4-isopropylpiperazin-1-ylmethyl)pyridin-3-yl]-N,N-dimethylbenzamide;
43) 1-cyclobutyl-4-[5-(4-ethanesulfonylphenyl)pyridin-2-ylmethyl]piperazine;
44) 1-[5-(4-ethanesulfonylphenyl)pyridin-2-ylmethyl]-4-isopropylpiperazine;
45) {4-[6-(4-cyclobutylpiperazin-1-ylmethyl)pyridin-3-yl]phenyl}-(4-methylpiperazin-1-yl)-methanone;
46) {4-[6-(4-isopropylpiperazin-1-ylmethyl)pyridin-3-yl]phenyl}-(4-methylpiperazin-1-yl)-methanone;
47) {4-[5-(4-isopropylpiperazin-1-ylmethyl)pyridin-2-yl]phenyl}-(4-methylpiperazin-1-yl)-methanone;
48) 4-[5-(4-isopropylpiperazin-1-ylmethyl)pyridin-2-yl]-N,N-dimethylbenzenesulfonamide;
49) 4-{4-[5-(4-isopropylpiperazin-1-ylmethyl)pyridin-2-yl]benzenesulfonyl}morpholine;
50) 1-cyclobutyl-4-{5-[4-(2-pyrrolidin-1-ylethyl)phenyl]pyridin-2-ylmethyl}piperazine;
51) 1-isopropyl-4-{5-[4-(2-pyrrolidin-1-ylethyl)phenyl]pyridin-2-ylmethyl}piperazine;
52) 1-cyclobutyl-4-[5-(4-pyrrolidin-1-ylmethylphenyl)pyridin-2-ylmethyl]piperazine;
53) 4-[6-(4-cyclobutylpiperazin-1-ylmethyl)pyridin-3-yl]benzonitrile;
54) 4-[6-(4-isopropylpiperazin-1-ylmethyl)pyridin-3-yl]benzonitrile;
55) 4-[6-(4-cyclobutylpiperazin-1-ylmethyl)pyridin-3-yl]benzaldehyde;
56) 4-[5-(4-isopropylpiperazin-1-ylmethyl)pyridin-2-yl]-N,N-dimethylbenzamide;
57) 4-[6-(4-isopropylpiperazin-1-ylmethyl)pyridazin-3-yl]-N,N-dimethylbenzenesulfonamide;
58) 4-[6-(4-isopropylpiperazin-1-ylmethyl)pyridazin-3-yl]-N,N-dimethylbenzamide;
59) {4-[6-(4-isopropylpiperazin-1-ylmethyl)pyridazin-3-yl]phenyl}morpholin-4-ylmethanone;
60) 3-(4-ethanesulfonylphenyl)-6-(4-isopropylpiperazin-1-ylmethyl)pyridazine;
61) {4-[6-(4-isopropylpiperazin-1-ylmethyl)pyridazin-3-yl]phenyl}piperidin-1-ylmethanone;
62) {4-[6-(4-isopropylpiperazin-1-ylmethyl)pyridazin-3-yl]phenyl}-(4-methylpiperazin-1-yl)-methanone and
63) 1-isopropyl-4-[5-(4-pyrrolidin-1-ylmethylphenyl)pyridin-2-ylmethyl]piperazine and, in one aspect, this invention relates specifically to each of these compounds individually. In another aspect, this invention relates specifically to a pharmaceutically acceptable salt of each of these compounds individually, more specifically to the specific salts mentioned in the specific examples below.

Combining one or more of the embodiments described herein, optionally also with one or more of the claims below, results in further embodiments and the present invention relates to all possible combinations of said embodiments and claims.

In one aspect, the invention provides the use of a compound according to formula I in a pharmaceutical composition. The pharmaceutical composition may in another aspect of the invention comprise, as an active ingredient, at least one compound according to formula I together with one or more pharmaceutically acceptable carriers or excipients. In another aspect, the invention provides such a pharmaceutical composition in unit dosage form, comprising from about 0.05 mg to about 1000 mg, e.g., from about 0.1 mg to about 500 mg, such as from about 0.5 mg to about 200 mg of the compound according to formula I.

In another aspect, the invention provides the use of a compound of formula I as defined above for the preparation of a pharmaceutical composition for the treatment of diseases and disorders in which an inhibition of the H3 histamine receptor has a beneficial effect.

In another aspect, the invention provides the use of a compound of formula I for the preparation of a pharmaceutical composition having histamine H3 antagonistic activity or histamine H3 inverse agonistic activity.

In another aspect the invention provides the use of a compound of formula I for the preparation of a pharmaceutical composition for the reduction of weight.

In another aspect, the invention provides the use of a compound of formula I for the preparation of a pharmaceutical composition for the treatment of overweight or obesity.

In another aspect, the invention provides the use of a compound of formula I for the preparation of a pharmaceutical composition for the suppression of appetite or for satiety induction.

In another aspect, the invention provides the use of a compound of formula I for the preparation of a pharmaceutical composition for the prevention and/or treatment of disorders and diseases related to overweight or obesity, such as dyslipidaemia, coronary heart disease, gallbladder disease, osteoarthritis and various types of cancer such as endometrial, breast, prostate and colon cancers.

In another aspect, the invention provides the use of a compound of formula I for the preparation of a pharmaceutical composition for the prevention and/or treatment of eating disorders, such as bulimia or binge eating.

In another aspect, the invention provides the use of a compound of formula I for the preparation of a pharmaceutical composition for the treatment of IGT (Impaired glucose tolerance).

In another aspect, the invention provides the use of a compound of formula I for the preparation of a pharmaceutical composition for the treatment of type 2 diabetes.

In another aspect, the invention provides the use of a compound of formula I for the preparation of a pharmaceutical composition for the delaying or prevention of the progression from IGT to type 2 diabetes.

In another aspect, the invention provides the use of a compound of formula I for the preparation of a pharmaceutical composition for the delaying or prevention of the progression from non-insulin requiring type 2 diabetes to insulin requiring type 2 diabetes.

In another aspect, the invention provides the use of a compound of formula I for the preparation of a pharmaceutical composition for the treatment of diseases and disorders in which a stimulation of the H3 histamine receptor has a beneficial effect.

In another aspect, the invention provides the use of a compound of formula I for the preparation of a pharmaceutical composition having histamine H3 agonistic activity.

In another aspect, the invention provides the use of a compound of formula I for the preparation of a pharmaceutical composition for the treatment of allergic rhinitis, ulcer or anorexia.

In another aspect, the invention provides the use of a compound of formula I for the preparation of a pharmaceutical composition for the treatment of Alzheimer's disease, narcolepsy, attention deficit disorders or reduced wakefulness, or for the regulation of sleep.

In another aspect, the invention relates to the use of a compound of formula I for the preparation of a pharmaceutical preparation for the treatment of airway disorders, such as asthma, for regulation of gastric acid secretion, or for treatment of diarrhoea.

In another aspect, the invention provides a method for the treatment of disorders or diseases related to the H3 histamine receptor, the method comprising administering to a subject in need thereof an effective amount of a compound of the general formula I as defined above, or of a pharmaceutical composition comprising such a compound.

In another aspect, the invention provides a method as described above, wherein the effective amount of the compound of the general formula I as defined above is in the range of from about 0.05 mg to about 2000 mg, preferably from about 0.1 mg to about 1000 mg, and more preferably from about 0.5 mg to about 500 mg per day.

In one aspect, the invention relates to compounds which exhibit histamine H3 receptor antagonistic activity or inverse agonistic activity and which may accordingly be useful in the treatment of a wide range of conditions and disorders in which histamine H3 receptor blockade is beneficial.

In another aspect, the invention provides a method for reduction of weight, the method comprising administering to a subject in need thereof an effective amount of a compound of formula I as defined above.

In another aspect, the invention provides a method for treatment of overweight or obesity, the method comprising administering to a subject in need thereof an effective amount of a compound of formula I.

In another aspect, the invention provides a method for suppression of appetite or for satiety induction, the method comprising administering to a subject in need thereof an effective amount of a compound of formula I.

In another aspect, the invention provides a method for prevention and/or treatment of disorders or diseases related to overweight or obesity, such as dyslipidaemia, coronary heart disease, gallbladder disease, osteoarthritis and various types of cancer, e.g., endometrial, breast, prostate or colon cancer, the method comprising administering to a subject in need thereof an effective amount of a compound of formula I.

In another aspect, the invention provides a method for prevention and/or treatment of eating disorders, such as bulimia and binge eating, the method comprising administering to a subject in need thereof an effective amount of a compound of formula I.

In another aspect, the invention provides a method for the treatment of IGT (Im-paired glucose tolerance), the method comprising administering to a subject in need thereof an effective amount of a compound of formula I.

In another aspect, the invention provides a method for the treatment of type 2 diabetes, the method comprising administering to a subject in need thereof an effective amount of a compound of formula I.

In another aspect, the invention provides a method for the delaying or prevention of the progression from IGT to type 2 diabetes, the method comprising administering to a subject in need thereof an effective amount of a compound of formula I.

In another aspect, the invention provides a method for the delaying or prevention of the progression from non-insulin requiring type 2 diabetes to insulin requiring type 2 diabetes, the method comprising administering to a subject in need thereof an effective amount of a compound of formula I.

In another aspect, the invention relates to compounds which exhibit histamine H3 receptor agonistic activity and which may accordingly be useful in the treatment of a wide range of conditions and disorders in which histamine H3 receptor activation is beneficial.

Compounds of the present invention may also be used for the treatment of airway disorders (such as asthma), as antidiarrhoeals, and for the modulation of gastric acid secretion.

Furthermore, compounds of the present invention may be used for the treatment of diseases associated with the regulation of sleep and wakefulness, and for the treatment of narcolepsy and attention deficit disorders.

Moreover, compounds of the invention may be used as CNS stimulants or as sedatives.

The present compounds may also be used for the treatment of conditions associated with epilepsy. Additionally, compounds of the invention may be used for the treatment of motion sickness and vertigo. Furthermore, they may be useful as regulators of hypothalamo-hypophyseal secretion, as antidepressants, as modulators of cerebral circulation, and in the treatment of irritable bowel syndrome.

Further, compounds of the present invention may be used for the treatment of dementia and Alzheimer's disease.

Compounds of the present invention may also be useful for the treatment of allergic rhinitis, ulcer or anorexia.

Compounds of the present invention may furthermore be useful for the treatment of migraine [see, e.g., *The Journal of Pharmacology and Experimental Therapeutics* 1998; 287: 43-50] and for the treatment of myocardial infarction [see *Expert Opinion on Investigational Drugs* 2000; 9: 2537-42].

In a further aspect of the invention, treatment of a patient with a compound of the present invention is combined with diet and/or exercise.

In a further aspect of the invention, one or more compounds of the present invention is/are administered in combination with one or more further active substances in any suitable ratio(s). Such further active agents may, for example, be selected from antiobesity agents, antidiabetics, antidyslipidemic agents, antihypertensive agents, agents for the treatment of complications resulting from or associated with diabetes, and agents for the treatment of complications and disorders resulting from or associated with obesity.

Thus, in a further aspect of the invention one or more compounds of the present invention may be administered in combination with one or more antiobesity agents or appetite regulating agents. Such agents may, for example, be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention, an antiobesity agent administered in combination with one or more compounds of the invention is leptin.

In another embodiment, such an antiobesity agent is dexamphetamine or amphetamine.

In another embodiment, such an antiobesity agent is fenfluramine or dexfenfluramine.

In still another embodiment, such an antiobesity agent is sibutramine.

In a further embodiment, such an antiobesity agent is orlistat.

In another embodiment, such an antiobesity agent is mazindol or phentermine.

In still another embodiment, such an antiobesity agent is phendimetrazine, diethyl-propion, fluoxetine, bupropion, topiramate or ecopipam.

In yet a further aspect of the invention, one or more compounds of the present invention may be administered in combination with one or more antidiabetic agents. Relevant antidiabetic agents include insulin, insulin analogues and derivatives such as those disclosed in EP 0 792 290 (Novo Nordisk A/S), e.g., $N^{\epsilon B29}$-tetradecanoyl des(B30) human insulin, EP 0 214 826 and EP 0 705 275 (Novo Nordisk A/S), e.g., $Asp^{B28}$ human insulin, U.S. Pat. No. 5,504,188 (Eli Lilly), e.g., $Lys^{B28}$ $Pro^{B29}$ human insulin, EP 0 368 187 (Aventis), e.g., Lantus®, all of which are incorporated herein by reference, GLP-1 derivatives, such as those disclosed in WO 98/08871 (Novo Nordisk A/S), incorporated herein by reference, as well as orally active hypoglycaemic agents.

The orally active hypoglycaemic agents preferably comprise imidazolines, sulfonylureas, biguanides, meglitinides, oxadiazolidinediones, thiazolidinediones, insulin sensitizers, α-glucosidase inhibitors, agents acting on the ATP-dependent potassium channel of the β-cells, e.g., potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists, such as one of those disclosed in WO 99/01423 and WO 00/39088 (Novo Nordisk A/S and Agouron Pharmaceuticals, Inc.), both of which are incorporated herein by reference, GLP-1 agonists, such as those disclosed in WO 00/42026 (Novo Nordisk A/S and Agouron Pharmaceuticals, Inc.), incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention, one or more compounds of the present invention may be administered in combination with insulin or an insulin analogue or derivative, such as $N^{\epsilon B29}$-tetradecanoyl des(B30) human insulin, $Asp^{B28}$ human insulin, $Lys^{B28}$ $Pro^{B29}$ human insulin, Lantus®, or a mix-preparation comprising one or more of these.

In a further embodiment of the invention, one or more compounds of the present invention may be administered in combination with a sulfonylurea, e.g., tolbutamide, chlorpropamide, tolazamide, glibenclamide, glipizide, glimepiride, glicazide or glyburide.

In another embodiment, one or more compounds of the present invention may be administered in combination with a biguanide, e.g., metformin.

In yet another embodiment of the invention, one or more compounds of the present invention may be administered in combination with a meglitinide, e.g., repaglinide or nateglinide.

In still another embodiment of the invention, one or more compounds of the present invention may be administered in combination with a thiazolidinedione insulin sensitizer, e.g., troglitazone, ciglitazone, pioglitazone, rosiglitazone, isaglitazone, darglitazone, englitazone, CS-011/CI-1037 or T 174, or a compound disclosed in WO 97/41097, WO 97/41119, WO 97/41120, WO 00/41121 and WO 98/45292, all of which are incorporated herein by reference.

In still another embodiment of the invention, one or more compounds of the present invention may be administered in combination with an insulin sensitizer, e.g., such as GI 262570, YM-440, MCC-555, JTT-501, AR-H039242, KRP-297, GW-409544, CRE-16336, AR-H049020, LY510929, MBX-102, CLX-0940, GW-501516, or a compound disclosed in WO 99/19313, WO 00/50414, WO 00/63191, WO 00/63192 or WO 00/63193 or in WO 00/23425, WO 00/23415, WO 00/23451, WO 00/23445, WO 00/23417, WO 00/23416, WO 00/63153, WO 00/63196, WO 00/63209, WO 00/63190 or WO 00/63189 (Novo Nordisk A/S), all of which are incorporated herein by reference.

In a further embodiment of the invention, one or more compounds of the present invention may be administered in combination with an α-glucosidase inhibitor, e.g., voglibose, emiglitate, miglitol or acarbose.

In another embodiment of the invention, one or more compounds of the present invention may be administered in combination with an agent acting on the ATP-dependent potassium channel of the β-cells, e.g., tolbutamide, glibenclamide, glipizide, glicazide, BTS-67582 or repaglinide.

In yet another embodiment of the invention, one or more compounds of the present invention may be administered in combination with nateglinide.

In still another embodiment, one or more compounds of the present invention may be administered in combination with an antihyperlipidemic agent or antilipidemic agent, e.g., cholestyramine, colestipol, clofibrate, gemfibrozil, lovastatin, pravastatin, simvastatin, probucol or dextrothyroxine.

In still another embodiment of the invention, one or more compounds of the present invention may be administered in combination with an antilipidemic agent, e.g., cholestyramine, colestipol, clofibrate, gemfibrozil, lovastatin, pravastatin, simvastatin, probucol or dextrothyroxine.

In another aspect of the invention, one or more compounds of the present invention may be administered in combination with more than one of the above-mentioned compounds, e.g., in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, one or more compounds of the present invention may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: *The Science and Practice of Pharmacy*, 19$^{th}$ Edition, Gennaro, Ed., Mack Publishing Co., Easton, Pa., 1995.

It should be understood that any suitable combination of compounds according to the invention with diet and/or exercise, one or more of the above-mentioned compounds and optionally one or more other active substances are considered to be within the scope of the present invention.

The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedi-sulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in *J Pharm Sci* 1977; 66: 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates which the present compounds are able to form.

The acid addition salts may be obtained as the direct products of compound synthesis. Alternatively, the free base may be dissolved in a suitable solvent containing the appropriate acid, and the salt isolated by evaporating the solvent or otherwise separating the salt and solvent.

Compounds of the present invention may form solvates with standard low molecular weight solvents using methods well known to the person skilled in the art. Such solvates are also to be understood as being within the scope of the present invention.

The invention also encompasses prodrugs of the present compounds which following administration undergo chemical conversion by metabolic processes before becoming active pharmacological substances. In general, such prodrugs will be functional derivatives of the present compounds which are readily convertible in vivo into the required compound of the formula I. Conventional procedures for the selection and preparation of suitable prodrug derivatives are described, for example, in *Design of Prodrugs*, ed. H. Bundgaard, Elsevier, 1985.

This invention also encompasses active metabolites of the present compounds.

Combining one or more of the individual embodiments described herein, optionally also with one or more of the individual claims below, results in further embodiments and the present invention relates to all possible combinations of said embodiments and claims.

In one embodiment, this invention relates to compounds of formula I with the definitions given herein, with the proviso that when $R^1$ is hydrogen, $C_{1-6}$-alkyl, $C_{2-6}$-alkenyl, $C_{3-8}$-cycloalkyl or $C_{3-8}$-cycloalkyl-$C_{1-6}$-alkyl, $R^2$ is hydrogen or $C_{1-6}$-alkyl; or $R^1$ and $R^2$ together with the atoms they are connected to form a nitrogen containing ring, optionally another heterocyclyl group; m is 0 (zero), 1 or 2; one of the four substituents $R^3$, $R^4$, $R^5$ and $R^6$ is any of the groups halogen, hydroxy, cyano or $C_{1-6}$-alkyl and three of the four substituents $R^3$, $R^4$, $R^5$ and $R^6$ are hydrogen, then X is different from —S—, and, in another embodiment, this invention relates to the use of such compounds as medicament and, in a still further embodiment, this invention relates to the use of such compounds for the treatment of any specific disease mentioned herein or any specific condition mentioned herein.

PHARMACEUTICAL COMPOSITIONS

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques, such as those disclosed in Remington: *The Science and Practice of Pharmacy*, 19th Edition, Gennaro, Ed., Mack Publishing Co., Easton, Pa., 1995. The pharmaceutical compositions may be specifically formulated for administration by any suitable route, such as the oral, rectal, nasal, pulmonary, topical (including buccal and sub-lingual), transdermal, intracisternal, intraperitoneal, vaginal or parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings, such as enteric coatings, or they can be formulated so as to provide controlled release of the active ingredient, such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also to be understood as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferably from about 0.05 to about 10 mg/kg body weight per day, administered in one or more doses, such as from 1 to 3 doses. The exact dosage will depend upon the frequency and mode of administration, the sex, age, weight and general condition of the subject treated, the nature and severity of the condition treated and any concomitant diseases to be treated, and other factors evident to those skilled in the art.

The formulations may conveniently be presented in unit dosage form by methods known to those skilled in the art. A typical unit dosage form for oral administration one or more times per day, such as from 1 to 3 times per day, may contain from 0.05 to about 1000 mg, preferably from about 0.1 to about 500 mg, and more preferably from about 0.5 mg to about 200 mg of a compound (or a salt or other derivative thereof as set forth above), according to the invention.

For parenteral routes, such as intravenous, intrathecal, intramuscular and similar administration, typical doses are of the order of about half the dose employed for oral administration.

The compounds of this invention are generally utilized as the free substance or as a pharmaceutically acceptable salt thereof. One example is an acid addition salt of a compound having a free base functionality. When a compound of the formula I contains a free base functionality, such salts are prepared in a conventional manner by treating a solution or suspension of the free base form of the compound of formula I with a chemical equivalent (acid-base equivalent) of a pharmaceutically acceptable acid. Representative examples of relevant inorganic and organic acids.are mentioned above. Physiologically acceptable salts of a compound of the invention having a hydroxy group include the anion of said compound in combination with a suitable cation, such as sodium or ammonium ion.

For parenteral administration, solutions of the novel compounds of the formula I in sterile aqueous solution, aqueous propylene glycol or sesame or peanut oil may be employed. Such aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylenes or water. Similarly, the carrier or diluent may include any sustained release material known in the art, such as glyceryl monostearate or glyceryl distearate, alone or mixed with a wax. The pharmaceutical compositions formed by combining the novel compounds of the formula I and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier may vary widely, but will usually be from about 25 mg to about 1 g. If a liquid carrier is used, the preparation may be in the form of a syrup, emulsion, soft gelatine capsule or sterile injectable liquid, such as an aqueous or non-aqueous liquid suspension or solution.

A typical tablet, which may be prepared by conventional tabletting techniques, may in the core contain 5.0 mg of a compound of the invention, 67.8 mg of lactosum Ph. Eur., 31.4 mg of cellulose, microcrystalline (Avicel), 1.0 mg of Amberlite®IRP88 (i.e., Polacrillin potassium NF, tablet disintegrant, Rohm and Haas) and magnesii stearas Ph. Eur. q.s. with a coating of approximately 9 mg of hydroxypropyl methylcellulose and approximately 0.9 mg of Mywacett 9-40 T (being acylated monoglyceride used as plasticizer for film coating).

If desired, the pharmaceutical composition of this invention may comprise the compound of the formula I in combination with one or more further pharmacologically active substances, e.g., substances chosen among those described in the foregoing.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (EPO guidelines C 4.13).

This invention includes all modifications and equivalents of the subject matter recited in the claims appended hereto as permitted by applicable law.

The following examples are offered by way of illustration, not by limitation. The representative examples mentioned below are specific embodiments of this invention.

Briefly, the compounds of this invention can be prepared in a manner known per se or analogous with known processes.

GENERAL EXPERIMENTAL PROCEDURES

NMR spectra were recorded at 300 and 400 MHz on a Bruker DRX300, Avance 300, DRX400 or AV400 instrument equipped with 5 mm selective-inverse (SEI, $^1$H and $^{13}$C), 5 mm broad-band inverse (BBI, $^1$H, broad-band) and 5 mm quadro nuclear (QNP, $^1$H, $^{13}$C) probe-heads, respectively. Shifts (δ) are given in parts per million (ppm) down field from tetramethylsilane as internal reference standard.

HPLC Method A. The RP-analyses was performed on a Merck-Hitachi series 7000 system (Merck-Hitachi pump L-7100 and Merck-Hitachi autosampler L-7200 or Rheodyne sample injector) using a Hibar™ RT 250-4, Lichrosorb™ RP-18, 5.0 μm, 4.0×250 mm column; gradient elution, 20% to 80% solvent B (0.1% TFA in acetonitrile) in solvent A (0.1% TFA in water) within 30 min, 1.0 ml/min, detection at 210 nm, temperature 30° C.

HPLC Method B. The RP-purification was performed on a Gilson system (3 Gilson 306 pumps, Gilson 170 DAD detector and a Gilson 215 liquid handler) using a Waters XTerra® Prep RP$_{18}$, 10 μm, 30 mm×150 mm column; gradient elution, 5% to 95% solvent B (acetonitrile) in solvent A (0.05% TFA in water) within 15 min, 40 mL/min, detection at 210 nm, temperature rt. The pooled fractions are either evaporated to dryness in vacuo, or evaporated in vacuo until the acetonitrile is removed, and then frozen and freeze dried.

HPLC Method C. The RP-analyses was performed on a Shimadzu LC-20 using a YMC-ODS, 5.0 μm, 4.6×50 mm column; gradient elution, 0% to 30% solvent B (0.1% TFA in acetonitrile) in solvent A (0.1% TFA in water) within 6 min, and then kept for 2 min, 2.5 mL/min, detection at 220 nm, temperature 30° C.

HPLC Method D. The RP-analyses was performed on a Shimadzu LC-20 using a YMC-ODS, 5.0 μm, 4.6×50 mm column; gradient elution, 0% to 60% solvent B (0.1% TFA in acetonitrile) in solvent A (0.1% TFA in water) within 8 min, and then kept for 2 min, 2.5 mL/min, detection at 220 nm, temperature 30° C.

HPLC Method E. The RP-analyses was performed on a Shimadzu using a YMC-ODS, 5.0 μm, 4.6×50 mm column; gradient elution, 10% to 80% solvent B (0.1% TFA in acetonitrile) in solvent A (0.1% TFA in water) within 6 min, and then kept for 2 min, 2.5 mL/min, detection at 220 nm, temperature 30° C.

HPLC Method F. The RP-purification was performed on a Gilson Nebula Series system using a Luna, 5 μm, 21.2 mm×250 mm column; gradient elution, 5% to 30% solvent B (0.1% TFA in acetonitrile) in solvent A (0.1% TFA in water) within 15 min, 80 mL/min, detection at 220 nm, temperature 25° C., injection volume 30 mL. The pooled fractions were evaporated in vacuo until acetonitrile was removed, and then frozen and dried.

HPLC-MS Method G. Column: Waters Xterra MS C-18×3 mm id. Buffer: Linear gradient 5%-95% in 4 min, acetonitrile, 0.01% TFA, flow rate 1.0 ml/min. Detection 210 nm (analog output from diode array detector), MS-detection ionisation mode API-ES, scan 100-1000 amu step 0.1 amu.

Microwave Synthesis. When microwave oven synthesis was applied, the reaction was heated by microwave irradiation in sealed microwave vessels in a single mode Emrys Optimizer EXP from PersonalChemistry®.

The examples below and the general procedures described herein refer to intermediate compounds and final products for general formula I identified in the specification and in the synthesis schemes. The preparation of the compounds of general formula I of the present invention is described in detail using the following examples. Occasionally, the reaction may not be applicable as described to each compound included within the disclosed scope of the invention. The compounds for which this occurs will be readily recognised by those skilled in the art. In these cases, the reactions can be successfully performed by conventional modifications known to those skilled in the art which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may be prepared by a person skilled in the art in analogy with the preparation of similar known compounds or by the General Procedures A through N described herein. The following examples are offered by way of illustration, not by limitation.

General Procedure A

Compounds of the formula I, wherein Y and/or W is —N═, and R, D, X each is as defined as for formula I, which compounds here are designated formula Ia, can be prepared as outlined below:

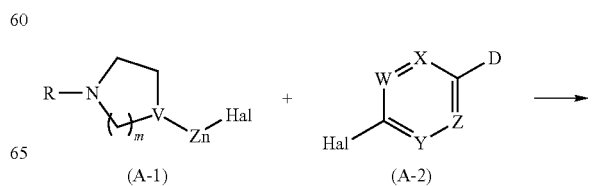

-continued

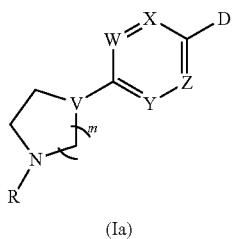

(Ia)

An amine of formula A-1, as defined herein, may be reacted in a coupling reaction catalyzed by a metal complex like [1,1'-bis(diphenylphosphino)ferrocene]dichloropalladium (II)-dichloromethane complex with a halogen substituted heteroaryl of the formula A-2 wherein D, X, Y, Z, and W each is as defined herein, and Hal represents chlorine or bromine, to give a compound of formula Ia. This reaction may be carried out in a suitable solvent like, for example, DMSO, THF, DMA, DMF, at a temperature of up to reflux, with a base like t-BuONa, NaOH, TEA, K₂CO₃ or Na₂CO₃. Compounds of formula A-1 is a Zn derivative of an amine as defined herein may be synthesized by methods known per se.

Compounds of formula A-2 may be prepared according to known procedures described in, for example, WO 03/066604A2, *Tetrahedron* 2000, 56, 9655-9662, and *Tetrahedron Lett.* 2001, 42, 2779-2781.

General Procedure B

Compounds of the formula Ib, wherein Y and/or W is —N═, and A is methylene, B, D, X, and each is as defined for formula I, which compounds here are designated formula Ib, can be prepared as outlined below:

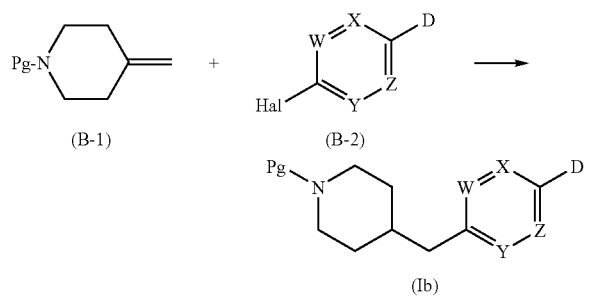

An amine of formula B-1, as defined herein, may be reacted with 9-BBN in THF at a temperature up to reflux further reaction in a coupling reaction catalyzed by a metal complex like [1,1'-bis(diphenylphosphino)ferrocene]dichloropalladium(II)-dichloromethane or Pd(dppf)Cl2•dichloromethane complex with a halogen substituted heteroaryl of the formula B-2 wherein D, X, Y, Z, and W each is as defined herein, and Hal represents chlorine or bromine, to give a compound of formula Ia. This reaction may be carried out in a suitable solvent like, for example, dimethylsulfoxide, tetrahydrofurane, dimethylacetamide, dimethylformamide, at a temperature of up to reflux, with a base like t-BuONa, NaOH, TEA, K₂CO₃ or Na₂CO₃. In compounds of formula B-1, Pg means a Boc or Cbz protected derivative of an amine as defined herein, which may be synthesized according to literature: S. Vice et. al. *JOC,* 2001, 66, 2487-2492 and *Bioorg. Med. Chem. Lett.* 2003, 13, 2167-2172.

General Procedure C

Compounds of the formula Ic, wherein Y and/or W is —N═, and A is methylene, B, D, X, and each is as defined for formula I, which compounds here are designated formula Ic, can be prepared as outlined below:

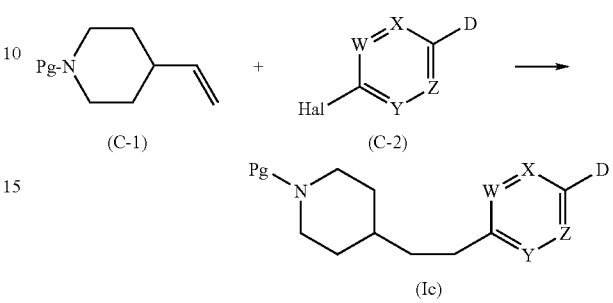

An amine of formula C-1, as defined herein, may be reacted with 9-BBN in THF at a temperature up to reflux further reaction in a coupling reaction catalyzed by a metal complex like [1,1'-bis(diphenylphosphino)ferrocene]dichloropalladium(II)-dichloromethane or Pd(dppf)Cl2•dichloromethane complex with a halogen substituted heteroaryl of the formula C-2 wherein D, X, Y, Z, and W each is as defined herein, and Hal represents chlorine or bromine, to give a compound of formula Ic. This reaction may be carried out in a suitable solvent like, for example, dimethylsulfoxide, tetrahydrofurane, dimethylacetamide, dimethylformaide, at a temperature of up to reflux, with a base like t-BuONa, NaOH, TEA, K₂CO₃ or Na₂CO₃. Compounds of formula C-1 may be a Boc or Cbz protected derivative of an amine as defined herein and may be synthesized according to literature: S. Vice et. al. in *JOC,* 2001, 66, 2487-2492, and *Bioorg. Med. Chem. Lett.* 2003, 13, 2167-2172.

General Procedure D

Compounds of the formula Id, wherein Y and/or W is —N═, D, X, and each is as defined for formula I, which compounds here are designated formula Ib, can be prepared as outlined below:

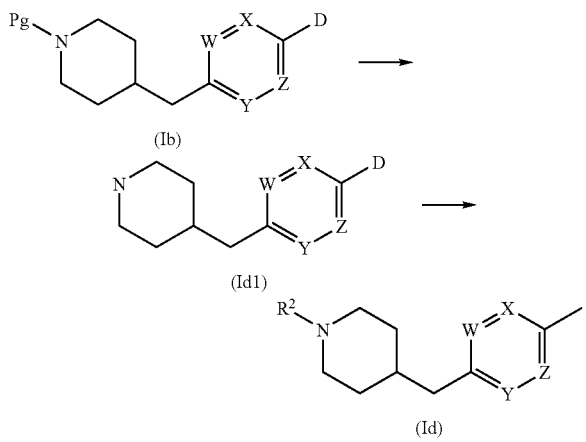

A protected amine of formula Ib, as defined herein, may be reacted with an acid like HCl, HBr or TFA in a solvent like THF, dichloromethane or diethyl ether at a temperature up to reflux to deprotect to compound of formula Id1. An amine of formula Ic1, wherein Y and/or W is —N═, D, X, and each is as defined for formula I may be reacted with a ketone or aldehyde in the presence of a reducing agent, to give a compound of formula Id. This reaction may be carried out in a suitable solvent like, for example water, methanol, tetrahydrofuran or 1,2-dichloroethane, at a temperature of up to reflux. The reducing agent may be, for example, NaCNBH$_3$ or NaBH(OAc)$_3$, eventually in the presence of a acidic catalyst like, for example, acetic acid. Compounds of formula Ib may be prepared according to other General Procedure(s) described in *Bioorg. Med. Chem. Lett.* 2003, 13, 2167-2172, and *J. Med Chem. Chim. Ther.* 1991, 26, 6, 625-637.

General Procedure E

Compounds of the formula Id, wherein Y and/or W is —N═, D, X, and each is as defined for formula I, which compounds here are designated formula Ie, can be prepared as outlined below:

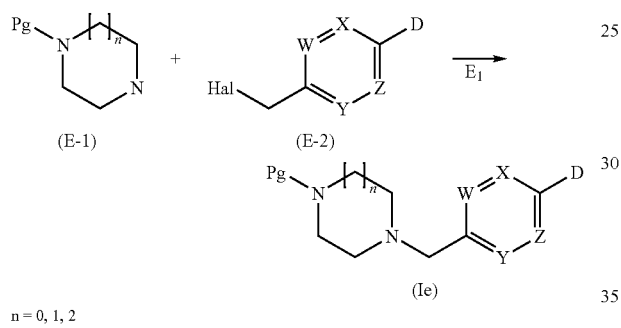

n = 0, 1, 2

A protected amine of formula E-1, as defined herein, may be reacted with an compound of formula E-2, wherein Y and/or W is —N═, D, X, and each is as defined for formula I, and Hal represents chlorine, bromine or trifluorosulfonate, to form a compound of formula Ie in a solvent like methanol, dimethylsulfoxide, tetrahydrofurane, dimethylacetamide, dimethylformaide or 1,2-dichloroethane, at a temperature of up to reflux, with bases like t-BuONa, NaOH, TEA, K$_2$CO$_3$ or Na$_2$CO$_3$.

Compounds of formula E2 may be prepared according to other general procedure(s) described in *J. Med. Chem.* 1992, 35, 3, 438-450; *J. Heterocycl. Chem.* 1986, 23, 149-152; and *J. Med. Chem. SIR* 2005, 48, 5, 1367-1383.

General Procedure F

Compounds of the formula I, wherein A, B, X, Y, W, Z and D each is as defined for formula I, which compounds here are designated formula Ii, can be prepared as outlined below:

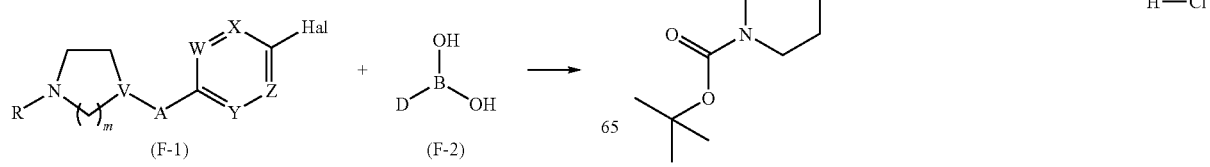

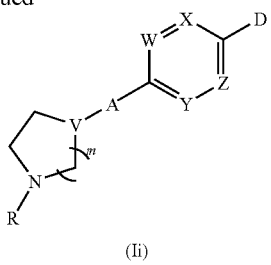

A compound of formula F-1, wherein A, R, V, X, Y, W and Z each is as defined herein, and Hal represents chlorine, bromine or iodine, may be reacted with a boronic acid derivative of the formula F-2, or a corresponding boronic acid ester derivative, wherein D is as defined herein, to give a compound of formula Ii. This reaction may be carried out in a suitable solvent like, for example, acetonitrile/water, at a temperature of up to 150° C. in the presence of a suitable catalyst like, for example, bistriphenylphosphinpalladium(II)dichloride and sodium carbonate. This reaction may also be performed starting from reactants wherein the halogen and boronic acid moieties have been interchanged. This reaction may be carried out under similar conditions as described above.

EXAMPLE 1

General Procedure A

5-[1,3-Benzodioxol-5-yl]-1'-isopropyl-1',2',3',4',5',6'-hexahydro-2,4'-bipyridinyl, dihydrochloride

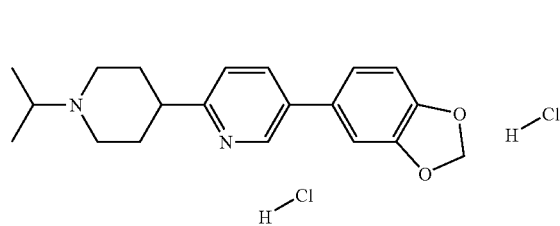

Step 1

5-1,3-[Benzodioxol-5-yl]-3',4',5',6'-tetrahydro-2'H-2,4'-bipyridinyl-1'-carboxylic acid tert-butyl ester, dihydrochloride

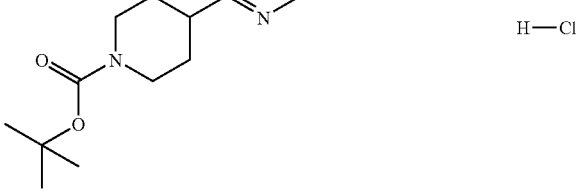

H—Cl

5-Bromo-3',4',5',6'-tetrahydro-2'H-[2,4']bipyridinyl-1'-carboxylic acid tert-butyl ester (0.33 g, 0.97 mmol), boronic acid (0.18 g, 1.06 mmol), bis(triphenylphosphin)palladium (II)chlorid (0.032 g, 0.046 mmol), 1 M Na2CO3 (4 ml) and acetonitrile (4 ml) were mixed in a 5 ml microwave vial. The reaction mixture was heated 1000 sec at 80° C. LC-MS showed more starting material, heating was continued for further 2000 sec at 80° C. The two phases were separated, the acetonitrile phase was evaporated and the crude product was purified on a silica gel column with EtOAc/heptane (1:4) as eluent. Yield: 250 mg white crystals (68%)

LC-MS (electrospray): m/z: 383 (M+1), Rt=1.47 min.

Step 2

5-1,3-Benzodioxol-5-yl-1',2',3',4',5',6'-hexahydro-2,4'-bipyridinyl

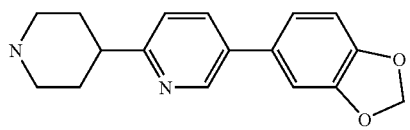 [SMILES: c1cc(C2CCNCC2)ncc1-c1ccc2c(c1)OCO2]

5-1,3-Benzodioxol-5-yl-3',4',5',6'-tetrahydro-2'H-2,4'-bipyridinyl-1'-carboxylic acid tert-butyl ester (0.250 g, 0.65 mmol) was dissolved in DCM (12 ml), TFA (3 ml) was added and the reaction mixture was stirred at room temperature for two hours. Water and 1 N NaOH was added, the DCM phase was washed and dried with $Na_2SO_4$. Evaporation afforded 150 mg white crystalline compound (81%).

$^1$H NMR (300 MHz, $CDCl_3$) δ: 8.8(1H, s), 8.5(2H, d), 8.3(1H, br s), 7.1(d,d, 2H), 6.95(d,d, 1H), 6.1(s, H), 3.6-3.7 (m, 3H), 3.2-3.4(2H), 2.4(m, 2H), 2.2-2.3 (2H, m), 1.55(1H, s)

Step 3

5-1,3-Benzodioxol-5-yl-1',2',3',4',5',6'-hexahydro-2,4'-bipyridinyl (0.15 g, 0.53 mmol) was dissolved in THF (4 ml), water (10 μL), propanone (70 μL, 0.8 mmol), acetic acid (100 μL) and 1 M sodium cyanoborohydride in THF (80 μL, 0.8 mmol) were added. The mixture was stirred at 60° C. overnight.

LC-MS still showed more starting material, more propanone (70 μL, 0.8 mmol) and 1 M sodium cyanoborohydride in THF (80 μL, 0.8 mmol) was added. Further stirring at RT still more starting material. Propanone (70 μL, 0.8 mmol) and 1 M sodium cyanoborohydride in THF (80 μL, 0.8 mmol) was added. Stirring overnight at RT. 1N HCl (1 ml) was added and the reaction mixture was purified on a prep. Gilson (HPLC Method B). Fractions with product was evaporated and 1 M HCl (3 ml) was added and evaporated. Made basic with 1 M NaOH (3 ml) and extracted with DCM. Organic layer evaporated and 1M HCl (1 mL) was added. The dihydrochloride of the title compound was isolated as light yellow crystals.

$^1$H NMR (300 MHz, MeOH-D4) δ: 9.00 (d, J=2.02 Hz, 1 H) 8.82 (dd, J=8.59, 2.53 Hz, 1 H) 8.09 (d, J=8.59 Hz, 1 H) 7.35-7.36 (m, 1 H) 7.32-7.34 (m, 1 H) 7.03 (d, J=8.59 Hz, 1 H) 6.08 (s, 2 H) 3.49-3.71 (m, 4 H) 3.32-3.37 (m, 2 H) 2.32-2.42 (m, 4 H) 1.45 (d, J=6.57 Hz, 6H).

LC-MS (electrospray): m/z: 325 (M+1) Rt=0.8 min (Method D)

EXAMPLE 2

General Procedure A

1'-Isopropyl-5-(4-morpholin-4-ylphenyl)-1',2',3',4',5',6'-hexahydro-[2,4']bipyridinyl, dihydrochloride

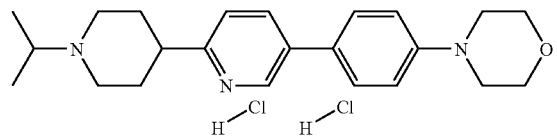

Step 1

5-(4-Morpholin-4-ylphenyl)-3',4',5',6'-tetrahydro-2'H-[2,4']bipyridinyl-1'-carboxylic acid tert-butyl ester

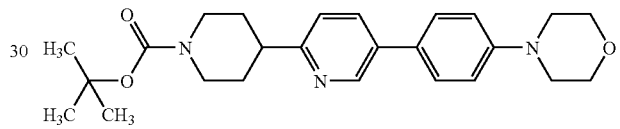

5-Bromo-3',4',5',6'-tetrahydro-2'H-[2,4']bipyridinyl-1'-carboxylic acid tert-butyl ester (0.6 g, 1.8 mmol), 4-morpholinylphenylboronic acid (400 mg, 1.9 mmol), bis(triphenylphosphine)-palladium(II)chloride (0.06 g, 0.09 mmol), 1 M $Na_2CO_3$ (4 ml) and acetonitrile (4 ml) were mixed in a 5 mL microwave vial. The reaction mixture was heated 1500 sec at 85° C. The water layer was removed. The acetonitrile phase was filtered and evaporated. The remainder was purified on a silicagel column with heptane: EtOAc (1:1) as eluent. 730 mg (98%) was isolated as the free base.

LC-MS (electrospray): m/z: 424 product and also 324 product without BOC

Step 2

5-(4-Morpholin-4-ylphenyl)-1',2',3',4',5',6'-hexahydro-[2,4']bipyridinyl

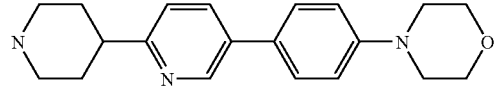 [SMILES: c1cc(N2CCOCC2)ccc1-c1ccc(C2CCNCC2)nc1]

5-(4-Morpholin-4-ylphenyl)-3',4',5',6'-tetrahydro-2'H-[2,4']bipyridinyl-1'-carboxylic acid tert-butyl ester (0.37 g, 0.874 mmol) was dissolved in DCM (12 mL), TFA (4 mL) was added and the reaction mixture was stirred at RT for 1 hour, until all starting material had disappeared. Water and 1 N NaOH was added until pH=12. After extraction with DCM (4×40 mL) the DCM phase was dried with $Na_2CO_3$, filtered and evaporated to give 280 mg (100%) white crystals.

¹H NMR (300 MHz, CDCl₃) δ: 8.75(d, 1H); 7.75(d,d, 1H), 7.5(d,d,2H), 7.2(d, 1H), 6.9(d, 2H), 3.9(m, 4H), 3.2(m, 6H), 2.7-2.9(m, 3H), 1.95(br, d, 2H), 1.6-2.05(m, 2H), 1.55(br s, 2H).

Step 3

5-(4-Morpholin-4-ylphenyl)-1',2',3',4',5',6'-hexahydro-[2, 4']bipyridinyl (0.28 g, 0.87 mmol) was dissolved in MeOH containing 2% acetic acid (10 mL). Propanone (255 uL, 3.46 mmol) and Na(CN)BH₃ (109 mg, 1.7 mmol) were added under stirring at RT. The reaction mixture was stirred overnight. Addition of propanone (60 uL, 0.87 mmol) and Na(CN)BH₃ (50 mg, 0.87 mmol) and further stirring for 3 hours was needed to complete the reaction. The reaction mixture was evaporated. Addition of 1M HCl (2 mL) methanol (2 mL) and a few drops of DMF dissolved the crude product. Further purification on the prep. HPLC (method B) afforded the title compound as the TFA salt. The TFA salt was redissolved in MeOH and HCl in diethyl ether was added. Evaporation in vacuo gave the title compound as yellow crystals.

LC-MS (electrospray): m/z: 366 (M+1); Rt=0.85 min.
¹H NMR (300 MHz, MeOH-D4) δ: 9.1(s, 1H), 8.85(d,d, 1H), 8.1(d, 1H), 7.95(d, 2H); 7.55(d, 2H), 4.05(m, 4H), 3.5-3.7(m, 10H), 2.35(m, 4H), 1.45(d, 6H).

EXAMPLE 3

General Procedure A

1-Isopropyl-2"-methyl-1,2,3,4,5,6-hexahydro-[4,2'; 5',4"]terpyridine, dihydrochloride

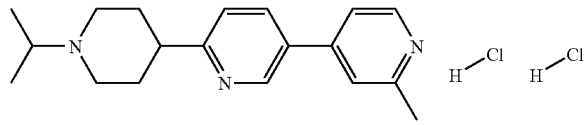

Step 1

2"-Methyl-3,4,5,6-tetrahydro-2H-[4,2';5',4"]terpyridine-1-carboxylic acid tert-butyl ester

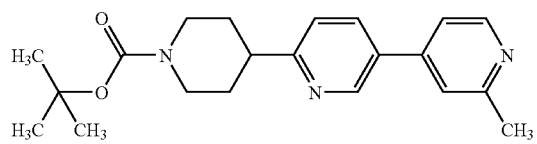 [SMILES: Cc1cc(-c2ccc(C3CCN(C(=O)OC(C)(C)C)CC3)nc2)ccn1]

5-Bromo-3',4',5',6'-tetrahydro-2'H-[2,4']bipyridinyl-1'-carboxylic acid tert-butyl ester (0.6 g, 1.76 mmol), 2-methylpyridine-4-boronic acid (264 mg, 1.9 mmol), bis(triphenylphosphine)-palladium(II)chloride (0.06 g, 0.09 mmol), 1 M Na₂CO₃ (4 ml) and acetonitrile (4 ml) were mixed in a 5 ml microwave vial. Another (2 ml) and acetonitrile (2 ml) were added. The reaction mixture was heated for 1500 sec. at 85° C. Water layer was removed. The acetonitrile phase was added DCM (20 mL). The organic phase was filtered and evaporated in vacuo. The crude mixture was purified on a silicagel column with EtOAc/heptane (4:1) and then EtOAc/heptane (9:1). The product was collected as a clear oil (540 mg, 87%).

LC-MS (electrospray): m/z: 354 (M+1); Rt=1.12 min.
¹H NMR (300 MHz, CDCl₃) δ: 8.85(d, 1H), 8.6(d, 1H), 7.48(s, 1H), 7.35(d, 1H), 7.28(d, 2H), 4.2(m, 2H), 2.8(m, 3H), 2.65(s, 3H), 1.95(m, 2H), 1.65-1.8(m, 2H), 1.5(d, 9H).

Step 2

2"-Methyl-1,2,3,4,5,6-hexahydro-[4,2';5',4"]terpyridine

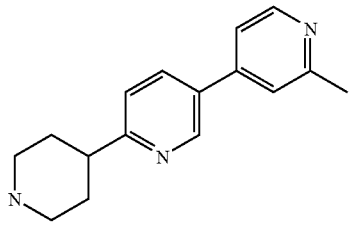 [SMILES: Cc1cc(-c2ccc(C3CCNCC3)nc2)ccn1]

2"-Methyl-3,4,5,6-tetrahydro-2H-[4,2';5',4"]terpyridine-1-carboxylic acid tert-butyl ester (0.54 g, 1.528 mmol) was dissolved in DCM (12 mL), TFA (4mL) was added the reaction mixture was stirred at RT for 2 hours. The reaction mixture was added water and 1N NaOH until pH=12. The organic phase was washed dried with Na₂CO₃ filtered and evaporation gave 310 mg (80%) yellow crystals.

¹H NMR (300 MHz, CDCl₃) δ: 8.8(d,d, 1H), 8.55(d, 1H), 7.8(d,d, 1H), 7.4(s, 1H), 7.3(m, 2H), 3.25(br. d, 2H), 2.9(t,t, 1H), 2.8(d,t, 2H), 2.6(s, 3H), 1.9(br.d, 2H), 1.7(m, 2H).

Step 3

2"-'Methyl-1,2,3,4,5,6-hexahydro-[4,2';5',4"]terpyridine (0.31 g; 1.22 mmol) was dissolved in 2% eddikesyre in methanol (10 ml). Propanone (360 uL, 4.9 mmol) and Na(C-N)BH3 (153 mg, 2.5 mmol) were added. The reaction mixture was stirred at RT over night. LC-MS showed some starting material let another propanone (90 uL, 1.2 mmol) and Na(CN)BH3 (75 mg, 1.2 mmol) were added further stirring at RT for 3 hours. The reaction mixture was evaporated in vacuo redissolved in 1N HCl (1 mL), MeOH (2 mL) and a few drops of DMF. The mixture was purified on prep. HPLC (Method D). The TFA salt was isolated. The TFA salt was dissolved in MeOH addition of HCl in diethylether evaporation afforded the dihydrochloride of the title compound as yellow crystals 210 mg (50%).

LC-MS (electrospray): m/z: (M+1); Rt=0.56 min.

¹H NMR (300 MHz, MeOH-D4) δ: 9.35(s, 1H), 8.9(m, 2H), 8.45(s, 1H), 8.35(d, 1H), 8.1(1H), 3.45-3.7(m, 5H), 2.9(s, 3H), 2.3-2.45(m, 4H), 1.45(d, 6H).

EXAMPLE 4

General Procedure A 5-(4-Ethanesulfonylphenyl)-1'-isopropyl-1',2',3',4',5',6'-hexahydro-[2,4']bipyridinyl, dihydrochloride

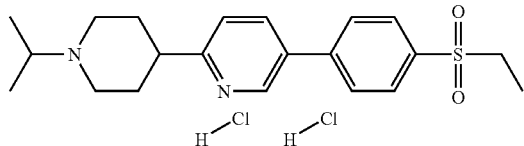

Step 1

5-(4-Ethanesulfonylphenyl)-3',4',5',6'-tetrahydro-2'H-[2,4']bipyridinyl-1'-carboxylic acid tert-butyl ester

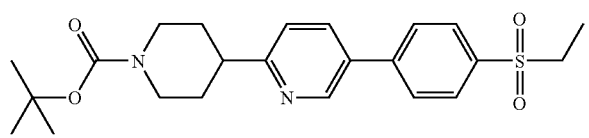 [SMILES: CCS(=O)(=O)c1ccc(-c2ccc(C3CCN(C(=O)OC(C)(C)C)CC3)nc2)cc1]

5-Bromo-3',4',5',6'-tetrahydro-2'H-[2,4']bipyridinyl-1'-carboxylic acid tert-butyl ester (0.6 g, 1.8 mmol), boronic acid (414 mg, 1.9 mmol), Bis(triphenylphosphine)palladium(II)chloride (0.06 g, 0.09 mmol), 1 M Na₂CO₃ (4 ml) and acetonitrile (4 ml) were mixed in a 5 mL microwave vial. The reaction mixture was heated for 1500 sec at 85° C. The water phase was removed and the acetonitrile phase was added DCM (20 mL), filtered and evaporated in vacuo. The crude reaction mixture was purified on a silica gel column with EtOAc:Heptane (1:1) as eluent. The product was isolated as an oil (760 mg, 100%)

LC-MS (electrospray): m/z: 431 (M+1); Rt=1.48 min.
¹H NMR (300 MHz, CDCl₃) δ: 8.8(d, 1H), 7.9(d, 2H), 7.85(d,d, 1H), 7.7(d, 2H), 7.25(d, 1H9, 4.25(m, 2H), 3.2(q, 2H), 2.8-2.9(m, 3H), 1.95(d, 2H), 1.75(m, 2H), 1.45(s, 9H), 1.35(t, 3H).

Step 2

5-(4-Ethanesulfonylphenyl)-1',2',3',4',5',6'-hexahydro-[2,4']bipyridinyl

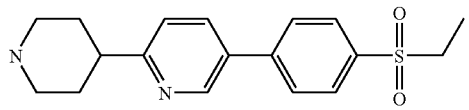

5-(4-Ethanesulfonylphenyl)-3',4',5',6'-tetrahydro-2'H-[2,4']bipyridinyl-1'-carboxylic acid tert-butyl ester (0.76 g, 1.675 mmol) was dissolved in DCM (12 mL) and TFA (4 mL) was added. The reaction mixture was stirred for 4 hours. 1N NaOH (20 mL) was added and the DCM phase was washed and dried with Na₂CO₃, filtered and evaporation gave 462 mg (79%) white crystalline compound.

¹H NMR (300 MHz, CDCl₃) δ: 8.85(s, 1H), 7.95(d, 2H), 7.8(d,d, 1H), 7.7(d, 2H), 7.25(d, 1H), 3.2(m, 2H), 3.15(q, 2H), 2.9(t,t, 1H), 2.7(t,d, 2H), 1.95(m, 2H), 1.7(d,t, 2H), 1.3(t, 3H).

Step 3

5-(4-Ethanesulfonylphenyl)-1',2',3',4',5',6'-hexahydro-[2,4']bipyridinyl (0.462, 1.4 mmol) was dissolved in 2% acetic acid in MeOH (10 mL). Propanone (410 uL, 5.6 mmol) and Na(CN)BH₃ (175 mg, 2.8 mmol) were added. The reaction mixture was stirred at RT over night. LC-MS showed some starting material left. More propanone (100 uL, 1.4 mmol) and Na(CN)BH₃ (88 mg, 1.4 mmol) were added and stirring continued for another 3 hours. The reaction mixture was evaporated in vacuo, redissolved in 1M HCl (2 mL), MeOH (2 mL) and a few drops of DMF. This mixture was filtered and purified on a prep. HPLC (Method B).

The TFA salt was isolated, redissolved in MeOH and 1N HCl (10 mL) was added. Evaporation gave the dihydrochloride of the title compound as white crystals, 300 mg (50%).

LC-MS (electrospray): m/z: 373 (M+1); Rt=0.92 min.
¹H NMR (300 MHz, MeOH-D4) δ: 9.15(s, 1H9, 9.0(d, 1H), 8.15(d, 2H), 8.05(s, 5H), 3.6-3.8(m, 4H), 3.2-3.4(6H), 2.35(m, 4H) 1.45(d, 6H), 1.25(t, 3H).

EXAMPLE 5

General Procedure A 4-(1'-Isopropyl-1',2',3',4',5',6'-hexahydro-[2,4']bipyridinyl-5-yl)-N,N-dimethylbenzamide, dihydrochloride

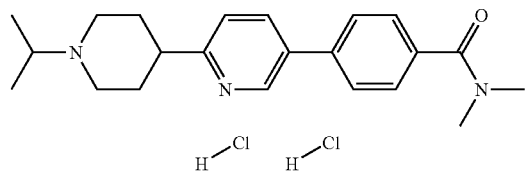

5-Bromo-3',4',5',6'-tetrahydro-2'H-[2,4']bipyridinyl-1'-carboxylic acid tert-butyl ester

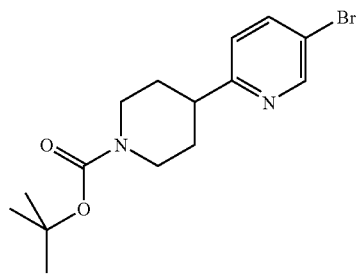 [SMILES: CC(C)(C)OC(=O)N1CCC(c2ccc(Br)cn2)CC1]

Pd-cat=[1,1'-bis(diphenylphosphino)ferrocene]dichloropalladium(II)-dichloromethane complex

Step 1

The 4-zinc-iodopiperidine-1-carboxylic acid compound was synthesized first. Celpure P65 is mixed with the zink dust in DME under nitrogen, and TMS-CI dissolved in 1,2-dibromo-methane was added in small portions. The reaction mixture was stirred at RT for additional 30 min. 4-Iodopiperidine-1-carboxylic acid dissolved in dry DME was added at a speed to keep the temperature between 58 and 60° C. To secure a total conversion, the reaction mixture was heated for additional 30 min. This reaction mixture was used in the next step after a filtration through a column with Celpure P65. The column was washed with an extra volume of dry DME to secure all material from the column.

Step 2

2,5-Dibromopyridine (10.26 g, 43.29 mmol) was mixed with Cu(1)1 (dry) (0.495 g, 2.597 mmol) and the Pd-catalyst (1.06 g, 0.03 mmol) in dry DME (30 mL) forming a slurry. The freshly filtered product from step 1 was added directly in the reaction mixture under $N_2$ and with good stirring. The reaction mixture was heated at 80° C. for 18 hours. The reaction mixture was added 1M $NH_4Cl$/water (100 mL) and was extracted with ethyl acetate 4×100 ml. The combined ethyl acetate phase was washed with brine and dried with $MgSO_4$. Filtration and evaporation in vacuo gave an oil. 6.9 g (48%).

Step 3

5-Bromo-1',2',3',4',5',6'-hexahydro-[2,4']bipyridinyl

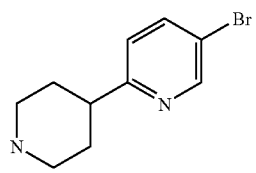

5-Bromo-3',4',5',6'-tetrahydro-2'H-[2,4']bipyridinyl-1'-carboxylic acid tert-butyl ester (6.9 g, 20.22 mmol) was dissolved in DCM. TFA (25 mL) was added slowly due to some $CO_2$ liberation and a slight heating of the reaction mixture. The reaction mixture was stirred for 35 min, then solvents were evaporated in vacuo. Addition of diethyl ether afforded the TFA salt as white crystals. Yield: 6.55 g (91%).

LC-MS (electrospray): m/z: 242 (M+1), Rt: 0.771 min.

$^1$H NMR (300 MHz, DMSO-D6) δ: 8.6(d, 1H), 8.0(d,d, 1H), 7.25(d, 1H), 3.5(m, 2H), 3.05(m, 3H), 1.75-2.05(m, 4H).

Step 4

5-Bromo-1'-isopropyl-1',2',3',4',5',6'-hexahydro-[2,4']bipyridinyl

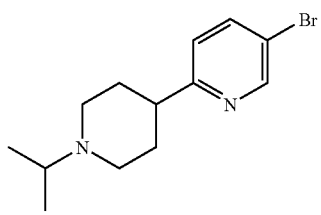 [SMILES: CC(C)N1CCC(c2ccc(Br)cn2)CC1]

5-Bromo-1',2',3',4',5',6'-hexahydro-[2,4']bipyridinyl (6.7 g, 18.9 mmol) was dissolved in 2% acetic acid in MeOH (40 ml). Propanone (8 mL, 113 mmol) and Na(CN)BH3 (3.6 g, 57 mmol) were added. The reaction mixture was stirred at RT over night. LC-MS showed only product. The reaction mixture was added 1N HCl filtered and evaporated in vacuo. The compound was dissolved in water pH was adjusted to PH=12 extracted with DCM (3×200 mL). The DCM phase was dried with $Na_2CO_3$ filtered and evaporation gave 4.4 g (82%) white crystals.

LC-MS (electrospray): m/z: 284 (M+1), Rt=0.89 min.

$^1$H NMR (300 MHz, DMSO-D6) δ: 8.6(d, 1H), 8.45(d,d, 1H), 7.26(d, 1H), 2.85(br. D, 2H), 2.65(p, 1H), 2.6(t, t, 1H), 2.15(d,t, 2H), 1.78(br. D, 2H), 1.65(m, 2H), 0.98(d, 6H).

Step 5

5-Bromo-1'-isopropyl-1',2',3',4',5',6'-hexahydro-[2,4']bipyridinyl (0.400 g, 1.412 mmol), N,N-dimethylbenzamide-4-boronic acid (0.327 g, 1.2 mmol) and bis(triphenylphosphine)palladium-(II)_chloride (50 mg, 0.07 mmol) were dissolved in acetonitrile (4 mL) and 1 M $Na_2CO_3$ (4 mL) under $N_2$ in a microwave vial (20 mL). The reaction mixture was heated 1200 sec at 85° C. The reaction mixture was separated and the acetonitrile phase was purified on a prep. HPLC (Method D). Evaporation in vacuo gave the TFA salt which was dissolved in MeOH and added HCl in diethyl ether. Evaporation in vacuo gave the dihydrochloride salt as white crystals. 350 mg (58%).

LC-MS (electrospray): m/z: 352 (M+1), Rt=1.403 min.

$^1$H NMR (300 MHz, MeOH-D4) δ: 9.15 (d, J=2.02 Hz, 1 H) 8.94 (dd, J=8.34, 1.77 Hz, 1 H) 8.17 (d, J=8.59 Hz, 1 H) 7.94 (d, J=8.08 Hz, 2 H) 7.65 (d, J=8.08 Hz, 2 H) 3.48-3.77

(m, 4 H) 3.32-3.41 (m, 2 H) 3.14 (s, 3 H) 3.04 (s, 3 H) 2.27-2.47 (m, 4 H) 1.45 (d, J=6.57 Hz, 6H).

EXAMPLE 6

General Procedure A

[2-Fluoro-4-(1'-isopropyl-1',2',3',4',5',6'-hexahydro-[2,4']bipyridinyl-5-yl)phenyl]pyrrolidin-1-ylmethanone, dihydrochloride

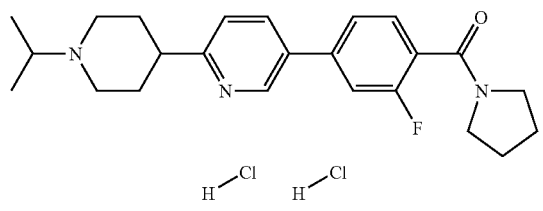

5-Bromo-1'-isopropyl-1',2',3',4',5',6'-hexahydro-[2,4']bipyridinyl (400 mg; 1.4 mmol), 2-fluorophenylpyrrolidine-1-ylmethanone-4 boronic acid (401 mg; 1.7 mmol) and bis(triphenylphosphin)palladium(II)chlorid (50 mg, 0.07 mmol) were dissolved in 4 mL acetonitrile and 4 mL 1M Na$_2$CO$_3$. in a 20 mL microwave vial. The reaction mixture was heated 1500 sec at 85° C. The water phase was removed and the acetonitrile phase was added 1N HCl (3 mL) filtered and evaporated in vacuo. The crude product was dissolved in acetonitrile and MeOH and purified on a prep. HPLC (Method D). The product was isolated as the TFA salt. Redissolving in 1 HCl (5 mL) and evaporation in vacuo twice afforded the title compound as the dihydrochloride. 382 mg (58%) crystals.

LC-MS (electrospray): m/z: 396 (M+1), Rt=0.75 min.
$^1$H NMR (300 MHz, MeOH-D4) δ: 9.04 (d, J=2.02 Hz, 1H) 8.59 (d, J=8.08 Hz, 1 H) 7.87 (d, J=8.08 Hz, 1 H) 7.70 (d, J=9.10 Hz, 2 H) 7.61 (t, J=7.33 Hz, 1 H) 3.55-3.72 (m, 5H) 3.38 (t, J=6.57 Hz, 3 H) 3.25-3.33 (m, 2 H) 2.17-2.43 (m, 4 H) 1.87-2.13 (m, 4 H) 1.44 (d, J=6.57 Hz, 6 H)

EXAMPLE 7

General Procedure A 3-(1'-Isopropyl-1',2',3',4',5',6'-hexahydro-[2,4']bipyridinyl-5-yl)-N,N-dimethylbenzamide, dihydrochloride

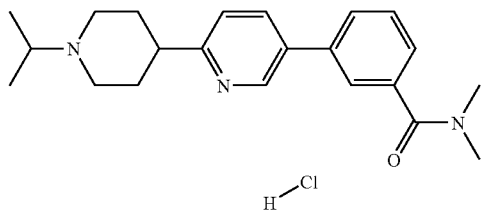

5-Bromo-1'-isopropyl-1',2',3',4',5',6'-hexahydro-[2,4']bipyridinyl (400 mg; 1.4 mmol) and N,N-dimethylbenzamide-3-boronic acid (0.327 g; 1.7 mmol) were reacted and purified in the same manner as in example 6. The title compound was isolated as the dihydrochloride 368 mg (61%) white crystals.

LC-MS (electrospray): m/z: 352 (M+1), Rt=0.78 min.
$^1$H NMR (300 MHz, MeOH-D4) δ: 9.06 (d, J=2.02 Hz, 1 H) 8.74 (dd, J=8.34, 1.77 Hz, 1 H) 8.00 (d, J=8.59 Hz, 1 H) 7.90 (d, J=7.58 Hz, 1 H) 7.85 (s, 1 H) 7.67 (t, J=7.58 Hz, 1 H) 7.59 (d, 1 H) 3.54-3.75 (m, 3 H) 3.40-3.53 (m, 1 H) 3.23-3.37 (m, 2 H) 3.14 (s, 3 H) 3.05 (s, 3 H) 2.20-2.44 (m, 4 H) 1.44 (d, J=7.07 Hz, 6 H)

EXAMPLE 8

General Procedure A

N,N-Diethyl-4-(1'-isopropyl-1',2',3',4',5',6'-hexahydro-[2,4']bipyridinyl-5-yl)benzamide, dihydrochloride

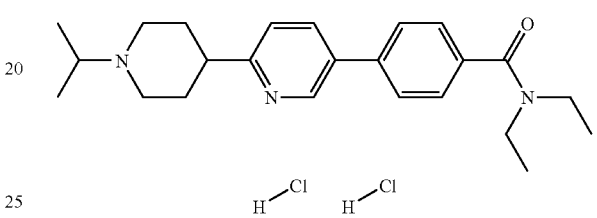

5-Bromo-1'-isopropyl-1',2',3',4',5',6'-hexahydro-[2,4']bipyridinyl (400 mg; 1.4 mmol) and N,N-diethylbenzamide-3-boronic acid (0.327 g; 1.7 mmol) were reacted and purified in the same manner as in example 6. The title compound was isolated as the dihydrochloride 200 mg (33%) white crystals.

LC-MS (electrospray): m/z: 380 (M+1), Rt=0.99 min.
$^1$H NMR (300 MHz, MeOH-D4) δ: 10.73 (s, 1 H) 9.05 (s, 1 H) 8.57 (d, J=7.07 Hz, 1 H) 7.88 (d, J=8.59 Hz, 2 H) 7.74 (d, J=8.08 Hz, 1 H) 7.51 (d, J=8.08 Hz, 2 H) 3.41-3.57 (m, 4 H) 3.31-3.40 (m, 2 H) 3.19-3.28 (m, 2 H) 3.04-3.18 (m, 2 H) 2.27-2.43 (m, 2 H) 2.15-2.27 (m, 2 H) 1.33 (d, J=6.57 Hz, 6 H) 1.02-1.22 (m, 6 H).

EXAMPLE 9

General Procedure A

[4-(1'-Isopropyl-1',2',3',4',5',6'-hexahydro-[2,4']bipyridinyl-5-yl)phenyl]-(4-methylpiperazin-1-yl)methanone, dihydrochloride

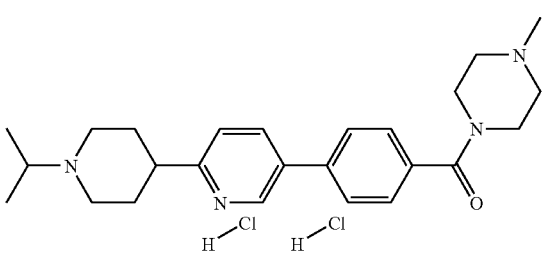

5-Bromo-1'-isopropyl-1',2',3',4',5',6'-hexahydro-[2,4']bipyridinyl (400 mg; 1.4 mmol) and 4-(4-methylpiperazine-1-carbonyl)phenylboronic acid, pinacol ester (0.56 g; 1.7 mmol) were reacted and purified in the same manner as in example 6. The title compound was isolated as the dihydrochloride 250 mg (37%) white crystals.

LC-MS (electrospray): m/z: 407 (M+1), Rt=0.50 min.

¹H NMR (300 MHz, MeOH-D4) δ: 9.16 (s, 1 H) 8.96 (d, J=8.29 Hz, 1 H) 8.20 (d, J=8.29 Hz, 1 H) 7.98 (d, J=7.91 Hz, 2 H) 7.73 (d, J=7.54 Hz, 2 H) 3.47-3.78 (m, 8 H) 3.16-3.44 (m, 6 H) 2.97 (s, 3 H) 2.35-2.47 (m, 4 H) 1.46 (d, J=6.41 Hz, 6 H).

EXAMPLE 10

General Procedure A

1"-Isopropyl-1-methyl-1",2",3",4",5",6"-hexahydro-1H-[3,3';6',4"]terpyridin-6-one, dihydrochloride

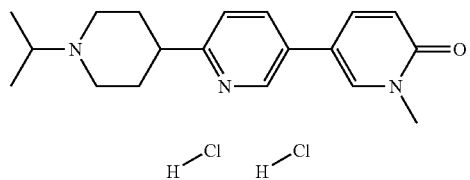

5-Bromo-1'-isopropyl-1',2',3',4',5',6'-hexahydro-[2,4']bipyridinyl (400 mg; 1.4 mmol) and N-methylpyridin-2-one-5-boronic acid pinacol ester (0.398 g; 1.7 mmol) was reacted and purified in the same manner as in example 6. The title compound was isolated as the dihydrochloride 100 mg (18%) white crystals.

LC-MS (electrospray): m/z: 312 (M+1), Rt=0.57 min.

¹H NMR (300 MHz, MeOH-D4) δ: 9.05(d, 1H), 8.8(d,d, 1H), 8.4(d, 1H), 8.1(d, 1H), 7.95(d,d,1H), 6.72(d, 1H), 3.7(s, 3H), 3.4-3.6(m, 4H), 3.3-3.35(m, 2H), 2.3-2.4(m, 4H), 1.4(d, 6H).

EXAMPLE 11

General Procedure A

[4-(1'-Isopropyl-1',2',3',4',5',6'-hexahydro-[2,4']bipyridinyl-5-yl)phenyl]pyrrolidin-1-ylmethanone, dihydrochloride

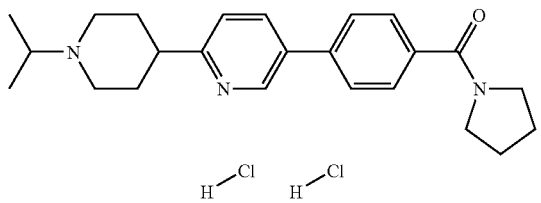

5-Bromo-1'-isopropyl-1',2',3',4',5',6'-hexahydro-[2,4']bipyridinyl (400 mg; 1.4 mmol) and N-pyrrolodinyl-1-carbonylphenyl-4-boronic acid (0.327 g; 1.7 mmol) were reacted and purified in the same manner as in example 6. The title compound was isolated as the dihydrochloride, 300 mg (47%) white crystals.

LC-MS (electrospray): m/z: 378 (M+1), Rt=0.93 min.

¹H NMR (300 MHz, MeOH-D4) δ: 9.1(s, 1H), 8.9(d,d, 1H), 8.15(d, 1H), 7.9(d, 2H), 7.7(d, 2H), 3.45-3.8(m, 8H9, 3.3-3.45(m, 2H), 2.5-2.45(m, 4H), 1.85-2.05(m, 4H), 1.5(d, 6H).

EXAMPLE 12

General Procedure A

1'-Isopropyl-5-[4-(piperidine-1-sulfonyl)phenyl]-1',2',3',4',5',6'-hexahydro-[2,4']bipyridinyl, dihydrochloride

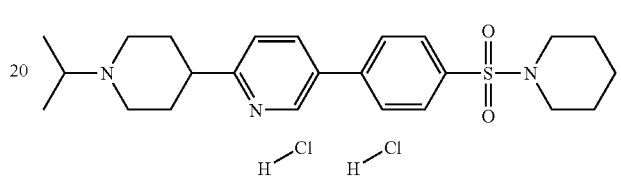

5-Bromo-1'-isopropyl-1',2',3',4',5',6'-hexahydro-[2,4']bipyridinyl (400 mg; 1.4 mmol) and 4-(1-piperidinylsulfonyl)phenylboronic acid (0.327 g; 1.7 mmol) were reacted and purified in the same manner as in example 6. The title compound was isolated as the dihydrochloride 300 mg (47%) white crystals.

LC-MS (electrospray): m/z: 428 (M+1), Rt=1.19 min.

¹H NMR (300 MHz, MeOH-D4) δ: 9.16 (d, J=2.02 Hz, 1 H), 8.88 (dd, J=8.59, 2.02 Hz, 1 H),) 8.12 (d, J=8.08 Hz, 1H), 8.05 (d, 2 H), 7.94 (d, J=8.08 Hz, 2 H), 3.46-3.73 (m, 6 H), 3.28-3.38 (m, 2 H), 2.99-3.06 (m, 4 H), 2.28-2.47 (m, 4 H), 1.59-1.68 (m, 4 H), 1.41-1.50 (m, 8 H).

EXAMPLE 13

General Procedure A 3-(4-Ethanesulfonylphenyl)-6-(1-isopropylpiperidin-4-yl)pyridazine, dihydrochloride

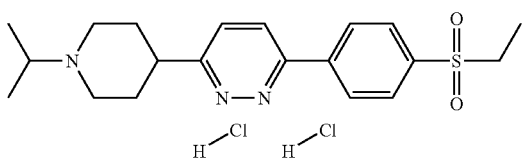

5-Bromo-1'-isopropyl-1',2',3',4',5',6'-hexahydro-[2,4']bipyridinyl (0.500 g; 2 mmol) and 4-ethansulfonylphenylboronic acid (0.377 g; 2 mmol) were reacted and purified in the same manner as in example 6. The title compound was isolated as the dihydrochloride 413 mg (46%) white crystals.

LC-MS (electrospray): m/z: 377 (M+1), Rt=0.947 min.

¹H NMR (300 MHz, MeOH-D4) δ: 8.9(d, 1H), 8.55(d, 1H), 8.48(d, 2H), 8.15(d, 2H), 3.6-3.75(m, 4H), 3.25-3.4(m, 4H), 2.45(m, 4H), 1.46(d, 6H), 1.25(t, 3H).

EXAMPLE 14

General Procedure A

[4-(1'-Cyclobutyl-1',2',3',4',5',6'-hexahydro-[2,4']bipyridinyl-5-yl)phenyl]-(4-methylpiperazin-1-yl)methanone, trihydrochloride

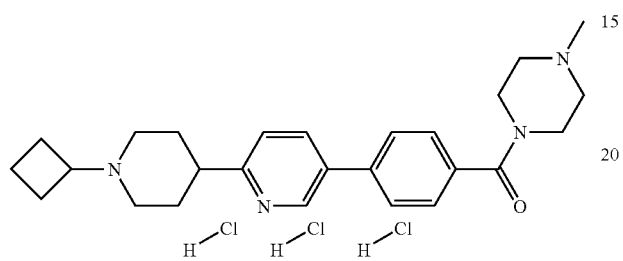

Step 1

5-Bromo-1'-cyclobutyl-1',2',3',4',5',6'-hexahydro-[2,4']bipyridinyl

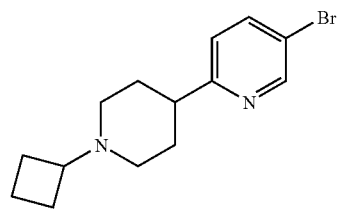 [SMILES: Brc1ccc(C2CCN(C3CCC3)CC2)nc1]

5-Bromo-1',2',3',4',5',6'-hexahydro-[2,4']bipyridinyl (6.4 g, 18.02 mmol) was dissolved in 2% acetic acid in MeOH (40 ml). Propanone (8 mL, 113 mmol) and Na(CN)BH₃ (3.6 g, 57 mmol) were added. The reaction mixture was stirred at RT overnight. The reaction mixture was added 1N HCl, filtered and concentrated in vacuo. The compound was dissolved in water and the pH was adjusted to 12, then extracted with DCM (3×200 mL). The crude product was treated with 1N HCl for 1 hour and extracted with diethyl ether to remove impurities. The aqueous phase was pH adjusted to pH=5.8-9. Extraction with ethyl acetate (3×100 mL) The organic phase was dried with Na₂CO₃, filtered and evaporation gave 4.6 g (86%) white crystals.

LC-MS (electrospray): m/z: 295 (M+1), Rt=0.95 min.
Mp=122.3-124.3° C.
¹H NMR (300 MHz, CDCl₃) δ: 8.6(d, 1H), 7.9(d,d, 1H), 7.5(s, 1H), 7.1(d, 1H), 3.2(m, 2H), 2.62-2.79(m, 2H), 2.0-2.1 (m, 2H), 1.6-1.97(m, 10H).

Step 2

5-Bromo-1'-cyclobutyl-1',2',3',4',5',6'-hexahydro-[2,4']bipyridinyl (0.8 g; 2.7 mmol), 4-((4-methylpiperazin-1-yl)-4-(4,4,5,5-tetramethyl-[1,3,2]dioxoborolan-2-yl)phenyl)methanone (1.07 g; 3.3 mmol) and bis(triphenylphosphine)palladium(II)chloride (100 mg, 0.14 mmol) were mixed in a 20 mL microwave vial in acetonitrile (7 ml) and 1 M Na₂CO₃ (7 ml) under N₂. The reaction mixture was heated for 1500 sec at 85° C. The water phase was removed, the acetonitrile phase was added 1N HCl (3 mL) and the solution was purified on the prep. HPLC (Method B). The product was isolated as the TFA salt. Redissolving in MeOH and addition of 1N HCl (5 mL) afforded the title compound as the trihydrochloride salt after evaporation in vacuo. Yield: 1 g (67%).

LC-MS (electrospray): m/z: 419.8 (M+1), Rt=1.05 min.
¹H NMR (300 MHz, MeOH-D4) δ: 9.16 (d, J=2.02 Hz, 1 H) 8.94 (dd, J=8.59, 2.02 Hz, 1 H) 8.18 (d, J=8.59 Hz, 1 H) 7.98 (d, J=8.08 Hz, 2 H) 7.73 (d, J=8.08 Hz, 2 H) 3.51-3.82 (m, 8 H) 3.30-3.35 (m, 2H) 3.20-3.29 (m, 2H) 3.04-3.15 (m, 2 H) 2.97 (s, 3H) 2.24-2.53 (m, 8 H) 1.81-1.99 (m, 2 H).

EXAMPLE 15

General Procedure A 4-(1'-Cyclobutyl-1',2',3',4',5',6'-hexahydro-[2,4']bipyridinyl-5-yl)-N,N-dimethylbenzamide, dihydrochloride 5-Bromo-1'-cyclobutyl-1',2',3',4',5',6'-hexahydro-[2,4']bipyridinyl (0.8 g; 2.7 mmol), N,N-dimethylbenzamide-4-boronic acid (0.627 g; 3.3 mmol) and bis(triphenylphosphine)palladium-(II)chloride (100 mg, 0.14 mmol) were mixed in a 20 mL microwave vial in acetonitrile (8 ml) and 1 M Na₂CO₃ (8 ml) under N₂. The reaction mixture was heated for 1500 sec at 85° C. The water phase was removed, the acetonitrile phase was added 1N HCl (3 mL) and the solution was purified on the prep. HPLC (Method B). The product was isolated as the TFA salt. Redissolving in MeOH and addition of 1N HCl (5 mL) afforded the title compound as the dihydrochloride salt after evaporation in vacuo. Yield: 500 g (42%) white crystals.

LC-MS (electrospray): m/z: 364.6 (M+1), Rt=0.767 min.
¹H NMR (300 MHz, MeOH-D4) δ: 9.14 (d, J=2.02 Hz, 1 H) 8.92 (dd, J=8.59, 2.02 Hz, 1 H) 8.15 (d, J=8.59 Hz, 1 H) 7.93 (d, J=8.59 Hz, 2 H) 7.65 (d, J=8.08 Hz, 2 H) 3.64-3.82

(m, 3 H) 3.48-3.60 (m, 1 H) 3.14 (s, 3 H) 3.06-3.12 (m, 2 H) 3.04 (s, 3 H) 2.23-2.51 (m, 8 H) 1.80-1.99 (m, 2 H).

EXAMPLE 16

General Procedure A 4-(1'-Cyclobutyl-1',2',3',4',5',6'-hexahydro-[2,4']bipyridinyl-5-yl)-N,N-diethylbenzamide, dihydrochloride

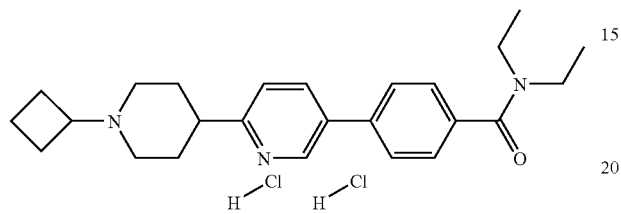

5-Bromo-1'-cyclobutyl-1',2',3',4',5',6'-hexahydro-[2,4']bipyridinyl (0.7 g; 2.37 mmol), N,N-diethylbenzamide-4-boronic acid (0.577 g; 2.61 mmol) were mixed and reacted and purified in exactly the same manner as in example 15.

Yield: 900 mg (81%) white crystals of the dihydrochloride of the title compound.

LC-MS (electrospray): m/z: 392.6 (M+1), Rt=0.881 min.

$^1$H NMR (300 MHz, MeOH-D4) δ: 9.15 (d, J=2.02 Hz, 1 H) 8.94 (dd, J=8.59, 2.02 Hz, 1H) 8.17 (d, J=8.08 Hz, 1 H) 7.94 (d, J=8.59 Hz, 2 H) 7.60 (d, J=8.08 Hz, 2 H) 3.64-3.88 (m, 3 H) 3.46-3.63 (m, 3 H) 3.27-3.39 (m, 2 H) 2.98-3.16 (m, 2 H) 2.18-2.54 (m, 8 H) 1.72-2.03 (m, 2 H) 1.28 (t, J=7.07 Hz, 3 H) 1.15 (t, J=6.82 Hz, 3 H)

EXAMPLE 17

General Procedure A

[4-(1'-Cyclobutyl-1',2',3',4',5',6'-hexahydro-[2,4']bipyridinyl-5-yl)phenyl]pyrrolidin-1-ylmethanone, dihydrochloride

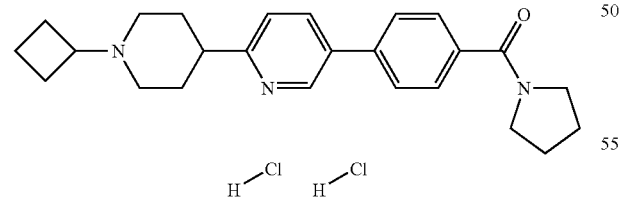

5-Bromo-1'-cyclobutyl-1',2',3',4',5',6'-hexahydro-[2,4']bipyridinyl (0.73 g; 2.5 mmol), N-pyrrolodinyl-1-carbonylphenyl-4-boronic acid (0.65 g; 3.0 mmol) were mixed and reacted and purified in exactly the same manner as in example 15.

Yield: 710 mg (62%) white crystals of the dihydrochloride of the title compound.

LC-MS (electrospray): m/z: 390.6 (M+1), Rt=0.937 min.

$^1$H NMR (300 MHz, MeOH-D4) δ: 9.15(s, 1H), 9.89(d,d, 1H), 8.18(d, 2H), 7.95(d, 2H), 7.75(d, 2H), 3.5-3.8(m, 6H), 3.1(d, t, 2H), 2.2-2.5(m, 8H), 1.8-2.1(m, 8H).

EXAMPLE 18

General Procedure A

4-[6-(1-Isopropylpiperidin-4-yl)pyridazin-3-yl]-N,N-dimethylbenzenesulfonamide, dihydrochloride

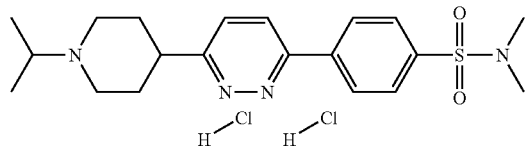

Step 1

6-(1-Isopropylpiperidin-4-yl)pyridazin-3-on

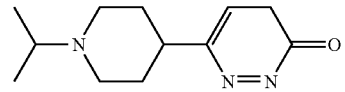

In analogy to Wermuth et al. in *J. Med. Chem.* 1987, 30 (2), 246, hydrazine hydrate (10 mL) was added to a solution of 4-(1-isopropylpiperidin-4-yl)-2-morpholin-4-yl-4-oxo-butyric acid (99.9 g, 0.25 mol) in 2-butanol (500 mL). The reaction mixture was stirred at room temperature for 1 h followed by reflux overnight. After cooling to room temperature the solvent was evaporated under reduced pressure. The residue was purified by flash column chromatography (SiO$_2$, dichloromethane with 3% methanol followed by 5% and 7%.). Evaporation of the fractions containing the desired product yielded a yellow solid, which was used as such.

Yield; 16.0 g=29% over 3 reaction steps.

LC-MS (electrospray): m/z: 222 (M+1); Rt=0.26 min.

$^1$H NMR (300 MHz, CDCl$_3$) δ: 12.6 (v.br.s, 1H, 7.23 (d, J=9.6 Hz, 1H), 6.92 (d, J=9.60 Hz, 1H), 3.02 (m, 2H), 2.84 (septet, J=6.57 Hz, 1H), 2.53 (m, 1H), 2.26 (dt, J=11.12, 3.54 Hz, 2H), 1.85 (m, 4H), 1.10 (d, J=6.57 Hz, 6H).

Step 2

3-Chloro-6-(1-isopropylpiperidin-4-yl)pyridazine, hydrochloride

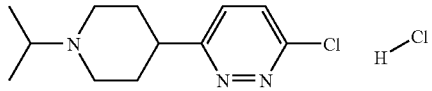

6-(1-Isopropylpiperidin-4-yl)pyridazin-3-on (5.76 g, 26 mmol) was added to POCl$_3$ (50 mL) and the reaction mixture was heated for 2 hours at 60° C. The excess of POCl$_3$ was evaporated in vacuo and ethanol (96%) was added under an exothermic reaction. The reaction mixture was cooled and a precipitate was obtained. The product was filtered off after drying in vacuo and 6.34 g (88%) white crystals were isolated.

LC-MS (electrospray): m/z: 240 (M+1); Rt=0.53 min.

$^1$H NMR (300 MHz, CDCl$_3$) δ: 10.50 (br.s, 1H), 7.95 (d, 1H) 7.80 (d, 1H), 3.51 (m, 3H), 3.31 (m, 1H), 3.18 (m, 2H), 2.30 (m, 2H), 2.18 (m, 2H), 1.35 (d, 6H).

Step 3

3-Chloro-6-(1-isopropylpiperidin-4-yl)pyridazine, hydrochloride (0.5 g, 1.6 mmol), N,N-dimethyl-4-boronobenzenesulfonamide (0.4 g, 1.76 mmol) and PdCl2(PPh3)2 (0.056 g, (0.08 mmol) were mixed in a 5 mL MW vial in 1N Na2CO3 (3 mL) and acetonitrile (2 mL). The reaction mixture was heated 500 sec at 130° C. I the microwave oven. The reaction mixture was added water (5 mL) and extracted with DCM (3×10 mL). The DCM phase was evaporated in vacuo, redissolved in acetonitrile and a few drops of TFA and evaporated again. The TFA salt was purified on the prep. HPLC (Method B). The title compound was isolated as the TFA salt. This salt was dissolved in MeOH (3 mL) and HCl in diethyl ether was added. Evaporation afforded the title compound as the dihydrochloride salt 438 mg (59%), slight beige crystals.

LC-MS (electrospray): m/z: 390 (M+1); Rt=1.04 min.

$^1$H NMR (400 MHz, MeOH-D4) δ: 8.8(d, 1H), 8.45(d, 1H), 8.45(d, 2H), 8.02(d, 2H), 3.55-3.75(m, 4H), 3.35(m, 2H), 2.25(s, 6H), 2.3-2.5(m, 4H), 1.45(d, 6H).

EXAMPLE 19

General Procedure A 3-(1-Isopropylpiperidin-4-yl)-6-(2-methylpyridin-4-yl)pyridazine, trihydrochloride

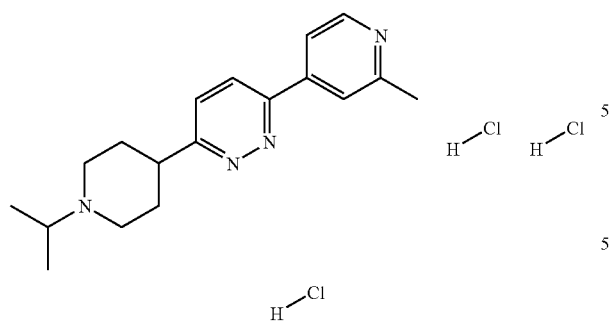

3-Chloro-6-(1-isopropylpiperidin-4-yl)pyridazine, hydrochloride (0.5 g, 1.6 mmol) and 2-methylpyridin boronic acid (0.241 g, 1.76 mmol) were mixed with catalyst and reacted in the same manner as in example 18. The title compound was isolated as white crystals of the trihydrochloride. Yield: 164 mg (25%).

LC-MS (electrospray): m/z: 298 (M+1); Rt=0.544 min.

$^1$H NMR (400 MHz, MeOH-D4) δ: 8.88(d,d, 1H), 8.75(s, 1H), 8.68(d, 2H), 8.12(d, 1H), 3.45-3.7(m, 4H), 3.3(m, 2H), 2.9(s, 3H), 2.35(m, 3H), 1.45(d, 6H).

EXAMPLE 20

General Procedure A

5-[6-(1-Isopropylpiperidin-4-yl)pyridazin-3-yl]-1-methyl-1H-pyridin-2-one, dihydrochloride

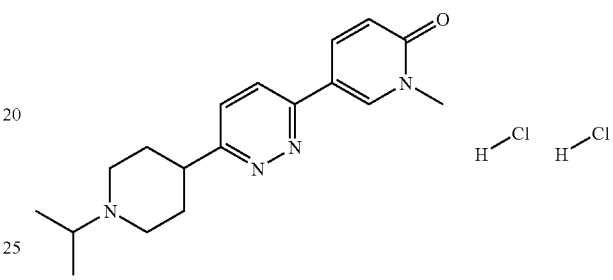

3-Chloro-6-(1-isopropylpiperidin-4-yl)pyridazine, hydrochloride (0.422 g, 1.35 mmol) and N-methylpyridin-2-on-5-boronic acid (0.349 g, 1.485 mmol) were mixed with catalyst and reacted in the same manner as in example 18. The title compound was isolated as white crystals of the dihydrochloride. Yield: 300 mg (58%).

LC-MS (electrospray): m/z: 314 (M+1); Rt=0.708 min.

$^1$H NMR (400 MHz, MeOH-D4) δ: 8.75(d, 1H), 8.7(d, 1H), 8.4(d, 1H), 8.2(d,d, 1H), 3.7(s, 3H), 3.45-3.65(m, 5H), 3.3(m, 1H), 2.35(m, 4H), 1.45(d, 6H).

EXAMPLE 21

General Procedure A

1'-Cyclobutyl-5-(4-ethanesulfonylphenyl)-1',2',3',4', 5',6'-hexahydro-[2,4']bipyridinyl, dihydrochloride

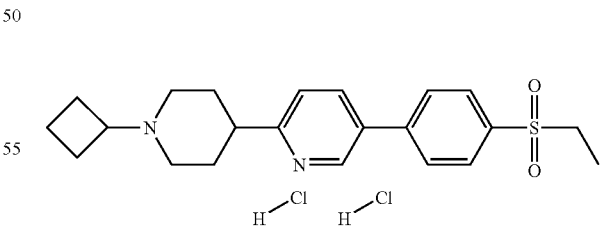

5-Bromo-1'-cyclobutyl-1',2',3',4',5',6'-hexahydro-[2,4']bipyridinyl (0.387 g; 1.312 mmol) and 4-ethansulfonylphenyl-boronic acid (0.337 g; 1.57 mmol) were mixed with catalyst and reacted in the same manner as in example 18. The title compound was isolated as white crystals of the dihydrochloride. Yield: 218 mg (36%)

LC-MS (electrospray): m/z: 385 (M+1); Rt=0.98 min.

$^1$H NMR (400 MHz, MeOH-D4) δ: 9.2(s, 1H), 8.89(d,d, 1H), 8.1(m, 5H), 3.65-3.75(m, 3H), 3.5(m, 1H), 3.3(m, 2H), 3.05(d,t, 2H), 2.1-2.45(m, 8H), 1.9(m, 2H), 1.25(t, 3H).

EXAMPLE 22

General Procedure A 4-(1'-Cyclobutyl-1',2',3',4',5',6'-hexahydro-[2,4']bipyridinyl-5-yl)-N,N-dimethylbenzenesulfonamide, dihydrochloride

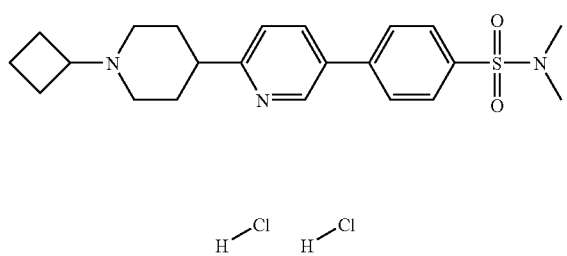

5-Bromo-1'-cyclobutyl-1',2',3',4',5',6'-hexahydro-[2,4']bipyridinyl (0.387 g; 1.312 mmol) and N,N-dimethyl-4-boronobenzenesulfonamide (0.361 g; 1.57 mmol) were mixed with catalyst and reacted in the same manner as in example 18. The title compound was isolated as white crystals of the dihydrochloride. Yield: 313 mg (50%)

LC-MS (electrospray): m/z: 400 (M+1); Rt=1.07 min.

$^1$H NMR (400 MHz, MeOH-D4) δ: 9.15(s, 1H), 8.9(d, 1H), 7.9-8.12(m, 5H), 3.65-3.78(m, 3H), 3.05(m, 2H), 2.7(s, 6H), 2.2-2.45(m, 8H), 1.3-2.0(m, 2H).

EXAMPLE 23

General Procedure A

1-Cyclobutyl-2''-methyl-1,2,3,4,5,6-hexahydro-[4,2'; 5',4'']terpyridine, trihydrochloride

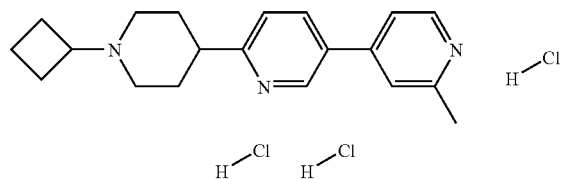

5-Bromo-1'-cyclobutyl-1',2',3',4',5',6'-hexahydro-[2,4']bipyridinyl (0.387 g; 1.312 mmol) and 2-methyl-4-pyridine boronic acid (0.215 g; 1.57 mmol) were mixed with catalyst and reacted in the same manner as in example 18. The title compound was isolated as white crystals of the trihydrochloride. Yield: 313 mg (50%)

LC-MS (electrospray): m/z: 308.6 (M+1); Rt=0.67 min.

$^1$H NMR (400 MHz, MeOH-D4) δ: 9.3(s, 1H), 8.8(d, 1H), 8.78(d,d, 1H), 8.45(s, 1H), 8.3(d, 1H), 8.8(d, 1H), 3.4-3.8(m, 3H), 3.4(m, 1H), 3.05(d,t, 2H), 2.9(s, 3H), 2.2-2.(m, 8H), 1.8-1.95(m, 2H).

EXAMPLE 24

General Procedure A

[4-(1'-Cyclobutyl-1',2',3',4',5',6'-hexahydro-[2,4'] bipyridinyl-5-yl)benzyl]pipethylamine, trihydrochloride

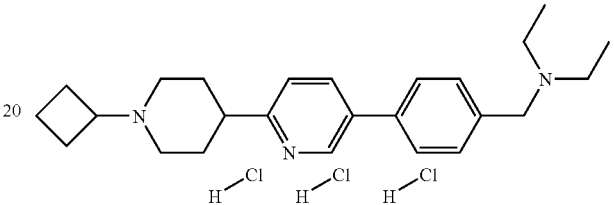

1-Cyclobutyl-2''-methyl-1,2,3,4,5,6-hexahydro-[4,2';5', 4'']terpyridine (0.40 g, 0.86 mmol) was dissolved in dry THF (15 mL) 5eq. 2N LiAlH$_4$ in THF was added very slowly through a syringe under N2 due to vigorous gas development. The reaction mixture turned orange. The reaction mixture was stirred 3 hours at RT. Water and 10% K$_2$CO$_3$ in water (1:3) were added carefully. The reaction mixture was filtered and the filter cake was washed with THF (3×10 mL). The THF phase was evaporated in vacuo and redissolved in MeOH then added 1N HCl (1 mL) and purified on a prep. HPLC (Method B). The TFA salt was obtained by evaporation dissolving in MeOH and addition of HCl in diethyl ether afforded the title compound as the trihydrochloride by evaporation in vacuo. Yield: 35 mg, (10%) white crystals.

LC-MS (electrospray): m/z: 378 (M+1); Rt=0.44 min.

$^1$H NMR (400 MHz, MeOH-D4) δ: 9.10 (s, 1 H), 8.79 (d, J=7.58 Hz, 1 H), 8.05 (d, J=8.08 Hz, 1 H), 7.95 (d, J=7.58 Hz, 2 H), 7.77 (d, J=7.58 Hz, 2 H), 4.46 (s, 2 H), 3.65-3.79 (m, 3 H), 3.40-3.52 (m, 1 H), 3.21-3.29 (m, 4 H), 3.06 (t, J=12.13 Hz, 2 H), 2.24-2.45 (m, 8 H), 1.83-1.99 (m, 2H), 1.38 (t, J=7.07 Hz, 6 H).

EXAMPLE 25

General Procedure A

1'-Cyclobutyl-5-(4-pyrrolidin-1-ylmethylphenyl)-1', 2',3',4',5',6'-hexahydro-[2,4']bipyridinyl, trihydrochloride

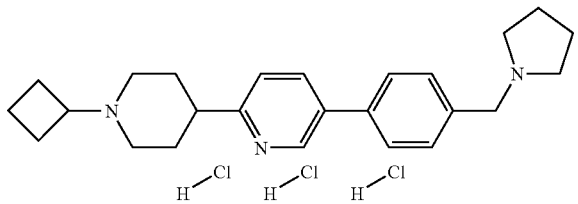

[4-(1'-Cyclobutyl-1',2',3',4',5',6'-hexahydro-[2,4']bipyridinyl-5-yl)phenyl]pyrrolidin-1-ylmethanone, dihydrochloride (0.35 g, 0.757 mmol) was reacted and purified in the same manner as in example 24.

Yield: 50 mg (16%) white crystals of the trihydrochloride.

LC-MS (electrospray): m/z: 376 (M+1); Rt=0.99 min.

$^1$H NMR (400 MHz, MeOH-D4) δ: 9.11(s, 1H), 8.83(d, 1H), 8.08(d, 1H), 7.95(d, 2H), 7.78(d, 2H), 4.49(s, 2H), 3.49-3.82(m, 6h), 3.17-3.28(m, 2H), 3.06(t, 2H), 2.17-2.48(m, 10H), 2.01-2.09(m, 2H), 1.83-1.98(m, 2H).

EXAMPLE 26

General Procedure A

[4-(1'-Cyclobutyl-1',2',3',4',5',6'-hexahydro-[2,4']bipyridinyl-5-yl)benzyl]dimethylamine, trihydrochloride

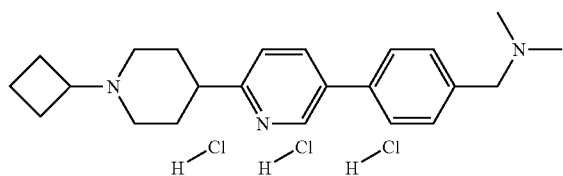

4-(1'-Cyclobutyl-1',2',3',4',5',6'-hexahydro-[2,4']bipyridinyl-5-yl)-N,N-dimethylbenzamide, dihydrochloride (0.33 g, 0.687 mmol) was reacted and purified in the same manner as in example 24.

Yield: 14 mg (4%) white crystals of the trihydrochloride.

LC-MS (electrospray): m/z: 359 (M+1); Rt=0.65 min.

$^1$H NMR (400 MHz, MeOH-D4) δ: 9.15(s, 1H), 8.92(d, 1H), 8.16(d, 1H), 7.98(d, 2H), 7.79(d, 2H), 4.45(s, 2H), 3.46-3.85(m, 4H), 3.09(t, 2H), 2.91(s, 6H), 2.22-2.54(m, 8H), 1.73-2.06(m, 2H).

EXAMPLE 27

General Procedure B

{4-[6-(1-Cyclobutylpiperidin-4-ylmethyl)pyridin-3-yl]phenyl}-(4-methylpiperazin-1-yl)-methanone, trihydrochloride

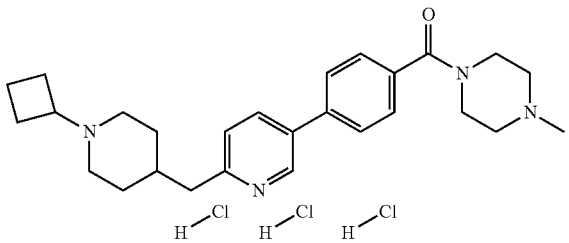

Step 1

4-(5-Bromopyridin-2-ylmethyl)piperidine-1-carboxylic acid tert-butyl ester

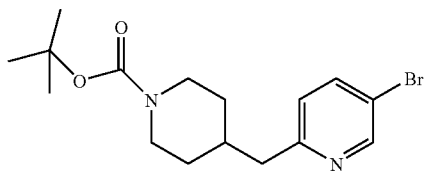 [SMILES: CC(C)(C)OC(=O)N1CCC(Cc2ccc(Br)cn2)CC1]

A solution of 9-BBN (0.5 N in THF, 100 mL) was added 4-methylenepiperidine-1-carboxylic acid tert-butyl ester (1.23 g, 1.5 mmol) the reaction mixture was stirred at reflux for 1 h. The reaction mixture was cooled to RT and added via a syringe to a solution of 2,5-dibromopyridine (11.3 g, 47.5 mmol) and Pd(dppf)Cl2 dichloromethane (1.23 g, 1.5 mmol) dissolved in DMF (100 mL) and water (9.9 mL) and K2CO3 (8.29 g). This mixture was heated at 60° C. for 3 hours. The DMF was the removed in vacuo. Addition of Ethylactetate/heptane afforded only some crystallisation. Therefore was the crude mixture evaporated once more to an oil. Further purification on a CombiFlash with Ethyl actetate/heptane (9:1) as eluent afforded 4-(5-bromopyridin-2-ylmethyl)piperidine-1-carboxylic acid tert-butyl ester as a brown oil. Yield: 8 g, (45%).

$^1$H NMR (400 MHz, CDCl3) δ: 8.6(d, 1H), 7.7(d,d, 1H), 6.99(d, 1H), 4.1(br. M, 2H), 2.6-2.7(m, 4H), 1.8-2.0(m, 2H), 1.5-1.6(m, 4H), 1.45(s, 9H).

Step 2

4-(5-bromopyridin-2-ylmethyl)piperidine, ditrifluoroacetate

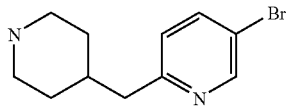 [SMILES: Brc1ccc(CC2CCNCC2)nc1]

4-(5-bromopyridin-2-ylmethyl)piperidine-1-carboxylic acid tert-butyl ester (8 g, 22.5 mmol) was dissolved in DMF TFA (25 mL) was added. The reaction is exothermic and some butane was developed. The reaction mixture was stirred at RT for 1 h. The reaction mixture was evaporated in vacuo and was stripped 4 times with acetone. The amine was isolated as the ditrifluoroacetate salt a brown oil. Yield: 10.9 g (100%).

LC-MS (electrospray): m/z: 255 and 257 (M+1) and (M+2); Rt=0.69 min.

Step 3

5-bromo-2-(1-cyclobutylpiperin-4-ylmethyl)pyridine

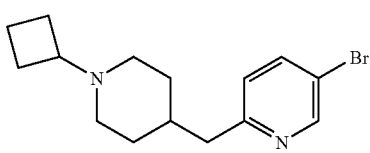 [SMILES: Brc1ccc(CC2CCN(C3CCC3)CC2)nc1]

4-(5-bromopyridin-2-ylmethyl)piperidine, ditrifluoroacetate (10.9 g, 22.5 mmol) and cyclobutanone (2.4 g, 34 mmol) were dissolved in acetic acid (4.2 g, 68 mmol) and MeOH (100 mL). NaCNBH$_3$ (2.1 g, 34 mmol) dissolved in water (20 mL) was added to the reaction mixture. The reaction mixture was stirred at RT over night. More cyclobutanone (1 mL) and NaCNBH$_3$ (830 mg) were and the reaction mixture was heated for 4 hours at 40° C. The reaction mixture was evaporated in vacuo to a thick oil. DCM (100 mL) and 1N NaOH (100 mL) were added. The organic phase was washed with water (50 mL) and brine (50 mL). Dried with Na$_2$SO$_4$, filtered and evaporated in vacuo to an oil. The oil was purified on a CombiFlash with ethyl acetate and finally with a gradient with up to 20% MeOH. The 5-bromo-2-(1-cyclobutylpiperin-4-ylmethyl)pyridine was isolated as white crystals 2.6 g (37%).

LC-MS (electrospray): m/z: 309 (M+1); Rt=0.88 min.

$^1$H NMR (400 MHz, MeOH-D4) δ: 8.6(d, 1H), 7.7(d,d, 1H), 7.25(s, 1H), 7.0(d, 1H), 2.75(d, 2H), 2.65(m, 3H), 1.6-2.1(m, 10H), 1.2-1.4(m, 3H).

Step 4

5-bromo-2-(1-cyclobutylpiperin-4-ylmethyl)pyridine (0.277 g, 0.89 mmol) and 4-((4-methylpiperazin-1-yl)-4-(4,4,5,5-tetramethyl-[1,3,2]dioxoborolan-2-yl)phenyl)methanone (0.354 g, 1.075 mmol) were mixed with catalyst and reacted in the same manner as in example 18. The title compound was isolated as white crystals of the trihydrochloride. Yield: 230 mg (47%).

LC-MS (electrospray): m/z: 433 (M+1); Rt=0.58 min.

$^1$H NMR (400 MHz, CDCl3) δ: 8.75(d,d, 1H), 7.78(d,d, 1H), 7.6(d, 2H), 7.5(d, 2H), 7.2(d, 1H), 3.8(br. S, 2H), 3.5(br. S, 2H), 2.85(d, 2H), 2.75(d, 2H), 2.65(m, 1H), 2.3-2.6(m, 2H), 2.3(s, 3H), 2.0(m, 2H), 1.8(m, 4H), 1.65(m, 4H), 1.45(m, 2H).

EXAMPLE 28

General Procedure B

4-[6-(1-Cyclobutylpiperidin-4-ylmethyl)pyridin-3-yl]-N,N-dimethylbenzenesulfonamide, dihydrochloride

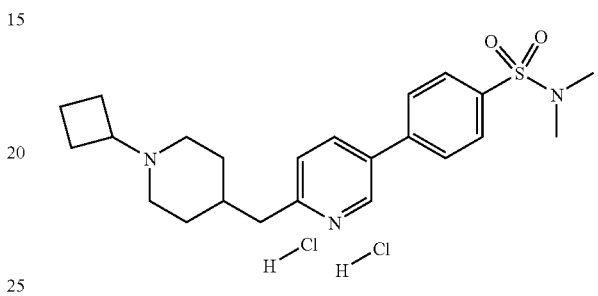

5-Bromo-2-(1-cyclobutylpiperin-4-ylmethyl)pyridine (0.277, 0.89 mmol) and N,N-dimethyl-4-boronobenzenesulfonamide (0.246 g; 1.075 mmol) were mixed with catalyst and reacted in the same manner as in example 18. The title compound was isolated as white crystals of the dihydrochloride. Yield: 190 mg (44%)

LC-MS (electrospray): m/z: 414 (M+1); Rt=0.95 min.

$^1$H NMR (400 MHz, CDCl3) δ: 8.78(d, 1H), 7.88(d, 2H), 7.8(d,d, 1H), 7.74(d, 2H), 7.2(d, 1H), 2.85(br. d, 2H), 2.78(d, 2H), 2.7(s, 6H), 2.65(m, 1H), 2.0(m, 2H), 1.7-1.9(m, 4H), 1.6-1.7(m, 5H), 1.3-1.47(m, 2H).

EXAMPLE 29

General Procedure B 6-(1-Cyclobutylpiperidin-4-ylmethyl)-2'-methyl-[3,4']bipyridinyl, dihydrochloride

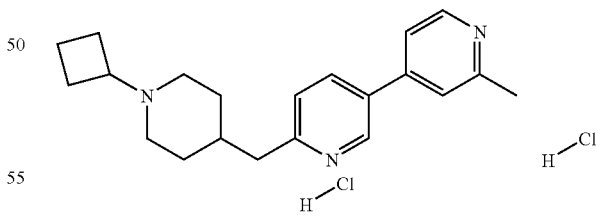

5-Bromo-2-(1-cyclobutylpiperin-4-ylmethyl)pyridine (0.277 g, 0.89 mmol) and 2-methyl-4-pyridine boronic acid (0.147 g; 1.075 mmol) were mixed with catalyst and reacted in the same manner as in example 18. The title compound was isolated as white crystals of the dihydrochloride. Yield: 190 mg (44%)

LC-MS (electrospray): m/z: 322 (M+1); Rt=0.68 min.

$^1$H NMR (400 MHz, CDCl3) δ: 8.78(d,d, 1H), 8.55(d, 1H), 7.8(d,d, 1H), 7.45(s, 1H), 7.25(d, 1H), 7.22(d,d, 1H), 2.85(m,

2H), 2.75(d, 2H), 2.65(m, 1H), 2.62(s, 3H), 1.75-2.1(m, 6H), 1.6-1.75(m, 5H), 1.45(m, 2H).

EXAMPLE 30

General Procedure B

4-[6-(1-Cyclobutylpiperidin-4-ylmethyl)pyridin-3-yl]-N,N-dimethylbenzamide, dihydrochloride

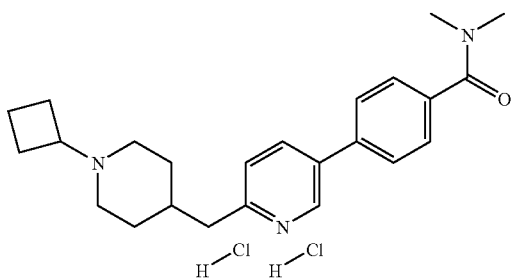

5-Bromo-2-(1-cyclobutylpiperin-4-ylmethyl)pyridine (0.500, 1.617 mmol) and N,N-dimethylbenzamide-4-boronic acid (0.347 g; 1.94 mmol) were mixed with catalyst and reacted in the same manner as in example 18. The title compound was isolated as white crystals of the dihydrochloride. Yield: 160 mg (26%)

LC-MS (electrospray): m/z: 322 (M+1); Rt=0.68 min.

$^1$H NMR (400 MHz, CDCl3) δ: 8.77(d, 1H), 7.78(d,d, 1H), 7.60(d, 2H), 7.35(d, 2H), 7.20(d, 1H), 3.14(s, 3H), 3.04(s, 3H), 2.86(d, 2H), 2.76(d, 2H), 2.60-2.69(m, 1H), 1.96-2.07 (m, 1H), 1.79-1.93(m, 3H), 1.62-1.71(m, 6H), 1.31-1.43(m, 2H).

EXAMPLE 31

General Procedure B

{4-[6-(1-Cyclobutylpiperidin-4-ylmethyl)pyridin-3-yl]phenyl}morpholin-4-ylmethanone, dihydrochloride

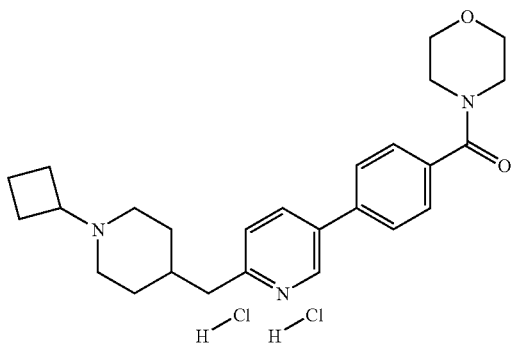

5-Bromo-2-(1-cyclobutylpiperin-4-ylmethyl)pyridine (0.320, 1.035 mmol) and N-morpholinyl-1-carbonylphenyl-4-boronic acid (0.292 g; 1.24 mmol) were mixed with catalyst and reacted in the same manner as in example 18. The title compound was isolated as white crystals of the dihydrochloride. Yield: 200 mg (46%)

LC-MS (electrospray): m/z: 420 (M+1); Rt=0.68 min.

$^1$H NMR (400 MHz, CDCl3) δ: 8.76(d, 1H), 8.08(d,d, 1H), 7.62(d, 2H), 7.52(d, 2H), 7.2(d, 1H), 3.44-3.83(m, 8H), 2.86 (d, 2H), 2.77(d, 2H), 2.58-2.71(m, 1H), 1.94-2.1(m, 2H), 1.8-1.92(m, 3H), 1.63-1.75(m, 6H), 130-1.48(m, 2H).

EXAMPLE 32

General Procedure B

{4-[6-(1-Cyclobutylpiperidin-4-ylmethyl)pyridin-3-yl]benzyl}dimethylamine, trihydrochloride

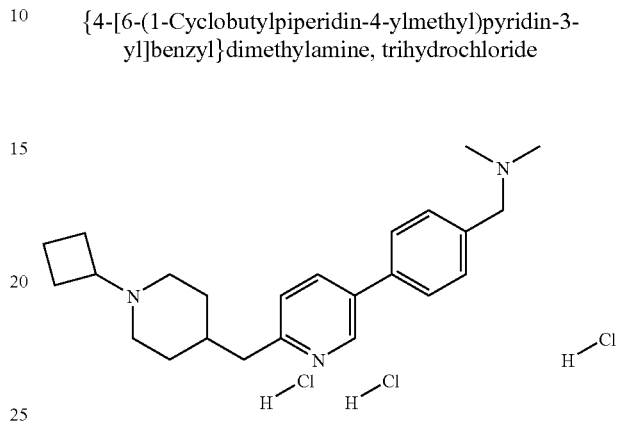

4-[6-(1-Cyclobutylpiperidin-4-ylmethyl)pyridin-3-yl]-N,N-dimethylbenzamide (0.160 g, 0.424 mmol) was dissolved in dry THF (10 mL) was reacted and purified in the same manner as in example 24.

Yield: 25 mg (16%) white crystals of the trihydrochloride.

LC-MS (electrospray): m/z: 374 (M+1); Rt=0.99 min.

$^1$H NMR (400 MHz, MeOH-D4) δ: 9.15(d, 1H), 8.9(d, 1H), 8.15(s, 1H), 7.95(d, 2H), 7.75(d, 2H), 4.45(m, 2H), 3.65(m, 1H), 3.45(m, 2H), 3.15(m, 2H), 2.9(s, 6H), 2.75-2.9 (m, 2H), 2.2-2.45(m, 6H), 1.7-2.1(m, 4H).

EXAMPLE 33

General Procedure B 2-(1-Cyclobutylpiperidin-4-ylmethyl)-5-(4-ethanesulfonylphenyl)pyridine, dihydrochloride

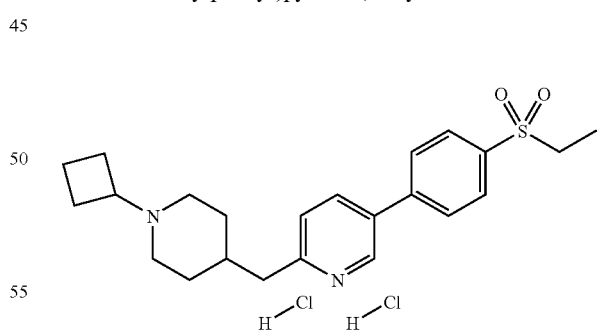

5-Bromo-2-(1-cyclobutylpiperin-4-ylmethyl)pyridine (0.360, 0.8415 mmol) and 4-ethansulfonylphenylboronic acid (0.197 g; 0.925 mmol) were mixed with catalyst and reacted in the same manner as in example 18. The title compound was isolated as white crystals of the dihydrochloride. Yield: 62 mg (16%)

LC-MS (electrospray): m/z: 399 (M+1); Rt=0.84 min.

$^1$H NMR (400 MHz, CDCl3) δ: 8.8(d, 1H), 8.0(d,d, 2H), 7.8(d,d, 1H), 7.75(d, 2H), 7.25(d, 1H), 3.15(q, 2H), 2.85(br.d,

2H), 2.78(d, 2H), 2.65(m, 1H), 2.05(m, 2H), 1.75-1.95(m, 2H), 1.55-1.75(7H), 1.35-1.45(m, 2H), 1.3(t, 3H).

EXAMPLE 34

General Procedure F

N-{4-[5-(4-Isopropylpiperazin-1-ylmethyl)pyridin-2-yl]phenyl}acetamide, trihydrochloride

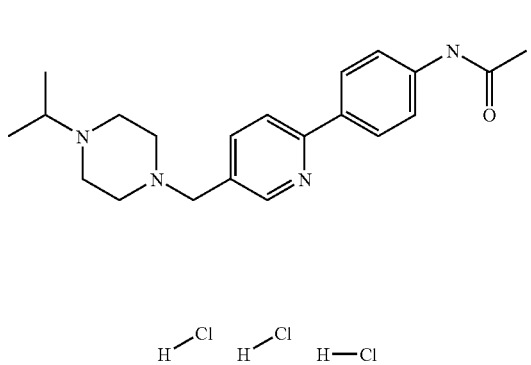

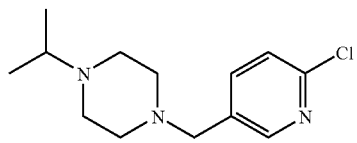 [SMILES: CC(C)N1CCN(Cc2ccc(Cl)nc2)CC1]

Correction: In this formula, a hydrogen atom is to be added to the nitrogen atom in the acetamido group.

Step 1

1-(6-Chloropyridine-3-ylmethyl)-4-isopropylpiperazine

Isopropylpiperazine (2.3 g, 17.94 mmol), 2-chloro-5-chloromethylpyridine (3.2 g, 19.73 mmol) and $K_2CO_3$ (26.91 g, 3.713 mmol) were mixed in EtOH (50 mL) a strongly exothermic reaction. The reaction was heated further for 12 hours at 65° C. The reaction mixture was filtered and evaporated. The crude product was used without any further purification.

HPLC (Method C) Rt=0.49 min, purity >92%.

Step 2

1-(6-Chloropyridin-3-ylmethyl)-4-isopropylpiperazine (0.2 g, 0.788 mmol) and 4-acetamido-phenylboronic acid (0.155 g, 0.867 mmol) were mixed with catalyst and was reacted in the same manner as in example 18. The title compound was isolated as yellow crystals of the trihydrochloride. Yield: 231 mg (64%).

LC-MS (electrospray): m/z: 353 (M+1); Rt=0.667 min.

$^1$H NMR (400 MHz, CDCl3) δ: 8.7(s, 1H), 8.5(d,d, 1H), 8.2(d, 1H), 7.77(d, 2H), 7.6(d, 2H), 4.2(s, 2H), 2.9-3.6(m, 9H), 2.1(s, 3H), 1.2(d, 6H).

EXAMPLE 35

General Procedure F

4-[5-(4-Isopropylpiperazin-1-ylmethyl)pyridin-2-yl]phenylamine, trihydrochloride

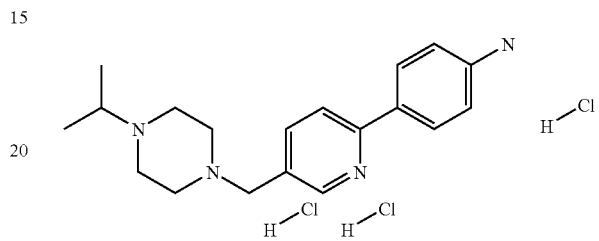

Correction: In this formula, two hydrogen atoms are to be added to the nitrogen atom attached to the benzene ring.

N-{4-[5-(4-Isopropylpiperazin-1-ylmethyl)pyridin-2-yl]phenyl}acetamide, trifluroacetic acid ((0.427 g, 0.92 mmol) was dissolved in 1 N HCl (5 mL) in a microwave vial (5 mL) the reaction mixture was heated 900 sec at 130° C. The reaction mixture was evaporated in vacuo affording the title compound as the trihydrochloride yellow crystals 397 mg (95%).

LC-MS (electrospray): m/z: 311 (M+1); Rt=0.532 min.

HPLC (Method C) Rt=0.48 min, purity=100%.

EXAMPLE 36

General Procedure F

1-[6-(4-Ethanesulfonylphenyl)pyridin-3-ylmethyl]-4-isopropylpiperazine, dihydrochloride

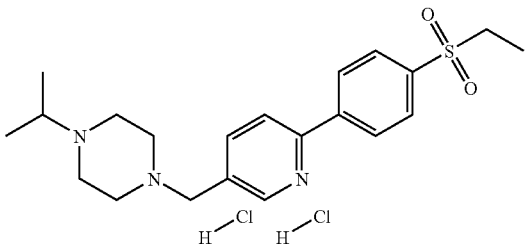

1-(6-Chloropyridin-3-ylmethyl)-4-isopropylpiperazine (0.2 g, 0.788 mmol) and 4-ethylsulfonylphenylboronic acid (0.186 g, 0.867 mmol) were mixed with catalyst and was reacted in the same manner as in example 18. The title compound was isolated as white crystals of the dihydrochloride. Yield: 260 mg (72%)

LC-MS (electrospray): m/z: 388 (M+1); Rt=0.867 min.

¹H NMR (400 MHz, DMSO-D6) δ: 8.83(s, 1H), 8.28(d, 2H), 8.2(m, 2H), 8.0(d, 2H), 4.5(s, 2H), 3.4-3.65(m, 8H), 3.3(q, 2H), 1.25(d, 6H), 1.1(t, 3H).

EXAMPLE 37

General Procedure F

1-Isopropyl-4-{6-[4-(piperidine-1-sulfonyl)phenyl]pyridin-3-ylmethyl}piperazine, dihydrochloride

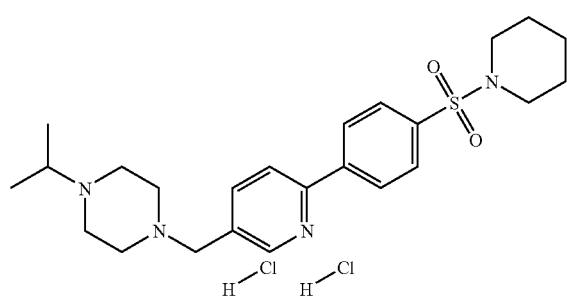

1-(6-Chloropyridin-3-ylmethyl)-4-isopropylpiperazine (0.2 g, 0.788 mmol) and 4-(1-piperidinylsulfonyl)phenylboronic acid (0.233 g, 0.867 mmol) were mixed with catalyst and reacted in the same manner as in example 18. The title compound was isolated as white crystals of the dihydrochloride. Yield: 295 mg (73%)

LC-MS (electrospray): m/z: 443 (M+1); Rt=1.134 min.

¹H NMR (400 MHz, DMSO-D6) δ: 8.82(d, 1H), 8.32(d,d, 1H), 8.2-8.25(m, 3H), 7.96(d, 2H), 4.15(s, 2H), 3.3-3.7(m, 7H), 3.05-3.25(m, 2H), 3.05(m, 4H), 1.65(m, 4H), 1.45(m, 2h9, 1.4(d, 6H).

EXAMPLE 38

General Procedure F 5-(4-Isopropylpiperazin-1-ylmethyl)-2'-methyl-[2,4']bipyridinyl, trihydrochloride

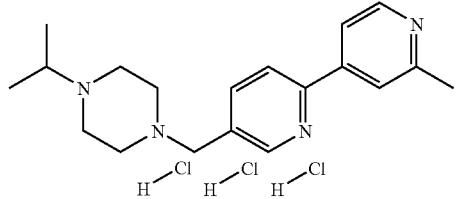

1-(6-Chloropyridin-3-ylmethyl)-4-isopropylpiperazine (0.2 g, 0.788 mmol) and 2-methylpyridin-4-boronic acid (0.119 g, 0.867 mmol) were mixed with catalyst and reacted in the same manner as in example 18. The title compound was isolated as yellow crystals of the trihydrochloride. Yield: 295 mg (73%).

LC-MS (electrospray): m/z: 311 (M+1); Rt=0.337 min.

¹H NMR (400 MHz, MeOH-D4) δ: 9.15(s, 1H), 8.8(d, 1H), 8.7(s, 1H), 8.65(d, 1H), 8.45(br.s, 2H), 4.75(s, 2H), 3.6-3.9 (m, 9H), 2.9(s, 3H), 1.45(d, 6H).

EXAMPLE 39

General Procedure F 1-(6-1,3-Benzodioxol-5-ylpyridin-3-ylmethyl)-4-isopropylpiperazine, dihydrochloride

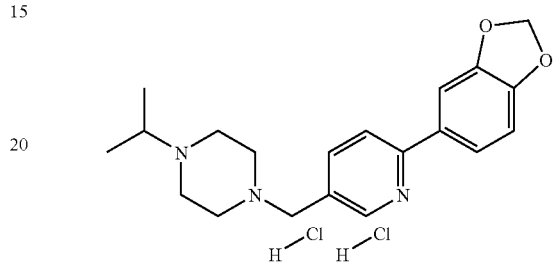

1-(6-Chloropyridin-3-ylmethyl)-4-isopropylpiperazine (0.2 g, 0.788 mmol) and 3,4-methylendi-oxyphenylboronic acid (0.144 g, 0.867 mmol) were mixed with catalyst and reacted in the same manner as in example 18. The title compound was isolated as yellow crystals of the dihydrochloride. Yield: 225 mg (69%)

LC-MS (electrospray): m/z: 340 (M+1); Rt=0.788 min.

¹H NMR (400 MHz, MeOH-D4) δ: 9.15(s, 1H), 8.85(d, 1H), 8.4(d, 1H), 7.6(d, 1H), 7.55(s, 1H), 7.15(d, 1H), 6.15(s, 2H), 4.2(s, 2H), 3.6-3.8(m, 9H), 1.45(d, 6H).

EXAMPLE 40

General Procedure F

4-{4-[5-(4-Isopropylpiperazin-1-ylmethyl)pyridin-2-yl]phenyl}morpholine, dihydrochloride

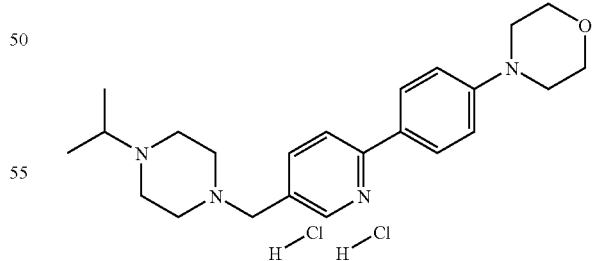

1-(6-Chloropyridin-3-ylmethyl)-4-isopropylpiperazine (0.2 g, 0.788 mmol) and 4-morpholino-phenylboronic acid (0.179 g, 0.867 mmol) were mixed with catalyst and was reacted in the same manner as in example 18. The title compound was isolated as yellow crystals of the dihydrochloride. Yield: 216 mg (52%)

LC-MS (electrospray): m/z: 381 (M+1); Rt=0.79 min.

$^1$H NMR (400 MHz, MeOH-D4) δ: 8.48(s, 1H), 7.75-7.85 (m, 4H), 7.05(d, 2H), 3.83(m, 4H), 3.68(s, 2H), 3.22(, 4H), 2.4-2.7(m, 9H), 1.05(d, 6H).

EXAMPLE 41

General Procedure F

4-[6-(4-Cyclobutylpiperazin-1-ylmethyl)pyridin-3-yl]-N,N-dimethylbenzamide, dihydrochloride

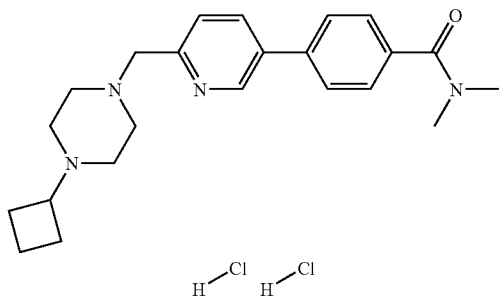

Step 1

1-(5-Bromopyridin-2-ylmethyl)-4-cyclobutylpiperazine

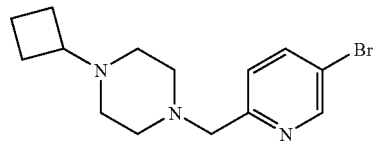 [SMILES: Brc1ccc(CN2CCN(C3CCC3)CC2)nc1]

1-(5-Bromopyridin-2-ylmethyl)piperazine (10 g, 39.04 mmol) was dissolved in THF (65 ml), water (0.6 mL), cyclobutanone (4.1 g, 58.6 mmol) and acetic acid (7.5 g, 125 mmol) was mixed. Then 1M NaCNBH$_3$ in THF (3.68 g, 58 mmol) (58 mL) was added. The reaction mixture was then heated and 21eq. water was added in order to solve the rest of material in the mixture. The reaction mixture was heated at 62° C. for 1.5 hours (LC-MS showed full conversion). The reaction mixture was however left overnight at 62° C. The reaction mixture was added DCM (150 mL) and water (100 mL). pH was adjusted to pH=10 with 4N NaOH. The water phase was extracted with DCM (2×25 mL). The combined DCM phase was washed with water (2×25 mL), brine (2×25 mL) finally dried MgSO$_4$, filtered and evaporated in vacuo gave 7.65 g (63%) of a thick oil.

LC-MS (electrospray): m/z: 312 (M+2); Rt=0.74 min.

$^1$H NMR (400 MHz, CDCl$_3$) δ: 8.6(d, 1H), 7.78(d,d, 1H), 7.3(d, 1H), 3.6(s, 2H), 2.85-2.95(m, 1H), 2.75(m, 1H), 2.3-2.65(m, 7H), 2.05(m, 2H), 1.9(m, 2H), 1.7(m, 2H).

Step 2

1-(5-Bromopyridin-2-ylmethyl)-4-cyclobutylpiperazine (0.596 g, 2 mmol) and N,N-dimethylbenzamide-4-boronic acid (0.463 g; 2.4 mmol) were mixed with catalyst and reacted in the same manner as in example 18. The title compound was isolated as yellow crystals of the dihydrochloride. Yield: 455 mg (50%)

LC-MS (electrospray): m/z: 379 (M+1); Rt=0.78 min.

$^1$H NMR (400 MHz, MeOH-D4) δ: DMSO; 9.05 (m, 1H), 8.37 (m, 1H), 7.87 (m, 3H), 7.57 (m, 2H), 4.60 (s, 2H), 3.78 (m, 1H), 3.68 (m, 2H), 3.55 (m, 4H), 3.33 (m, 2H), 3.01 (s, 3H), 2.95 (s, 3H), 2.39 (m, 2H), 2.16 (m, 2H), 1.73 (m, 2H).

EXAMPLE 42

General Procedure F

4-[6-(4-Isopropylpiperazin-1-ylmethyl)pyridin-3-yl]-N,N-dimethylbenzamide, dihydrochloride

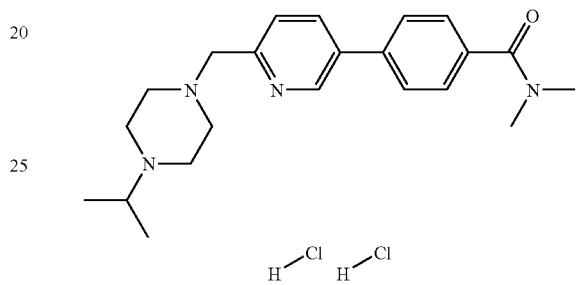

Step 1

1-(5-Bromopyridin-2-ylmethyl)-4-isopropylpiperazine

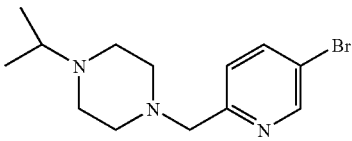 [SMILES: CC(C)N1CCN(Cc2ccc(Br)cn2)CC1]

1-(5-Bromopyridin-2-ylmethyl)piperazine (10 g, 39.04 mmol) was dissolved in THF (65 ml), water (0.6 mL), propanone (4.5 g, 78.08 mmol) and acetic acid (7.5 g, 125 mmol) was mixed. Then 1M NaCNBH$_3$ in THF (3.68 g, 58 mmol) (58 mL) was added. The reaction mixture was then heated and 21eq. water was added in order to solve the rest of material in the mixture. The reaction mixture was stirred overnight at 45° C. The reaction mixture was added DCM (150 mL) and water (100 mL). pH was adjusted to pH=10 with 4N NaOH. The water phase was extracted with DCM (2×25 mL). The combined DCM phase was washed with water (2×25 mL), brine (2×25 mL) finally dried MgSO$_4$, filtered and evaporated in vacuo giving 7.56 g (65%) of a thick oil.

LC-MS (electrospray): m/z: 298 (M+1); Rt=0.67 min.

$^1$H NMR (400 MHz, CDCl$_3$) δ: 8.62(d, 1H), 7.78(d,d, 1H), 7.3(d, 1H), 3.65(s, 2H), 2.75(m, 1H), 2.55-2.7(m, 8H), 1.1(d, 6H).

Step 2

1-(5-Bromopyridin-2-ylmethyl)-4-isopropylpiperazine (0.596, 2.0 mmol) and N,N-dimethylbenzamide-4-boronic acid (0.463 g; 2.4 mmol) were mixed with catalyst and reacted in the same manner as in example 18. The title compound was isolated as yellow crystals of the dihydrochloride. Yield: 136 mg (19%)

LC-MS (electrospray): m/z: 367 (M+1); Rt=0.74 min.

$^1$H NMR (400 MHz, D$_2$O) δ: 8.96 (d, 1H), 8.67 (dd, 1H), 7.98 (d, 1H), 7.80 (d, 2H), 7.56 (d, 2H), 4.17 (s, 2H), 3.62 (m, 3H), 3.26 (m,broad, 4H), 3.06 (s, 3H), 2.97 (s, 3H), 2.86 (m, broad, 2H), 1.32 (m, 6H).

EXAMPLE 43

General Procedure F

1-Cyclobutyl-4-[5-(4-ethanesulfonylphenyl)pyridin-2-ylmethyl]piperazine, dihydrochloride

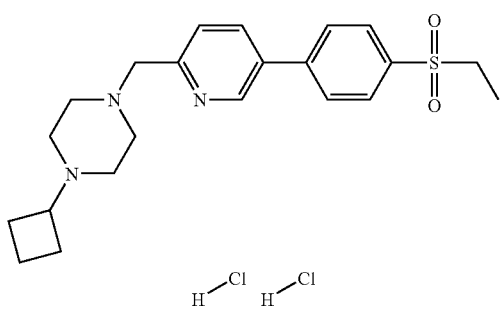

1-(5-Bromopyridin-2-ylmethyl)-4-cyclobutylpiperazine (0.62, 2.0 mmol) and 4-ethylsulfonylphenylboronic acid (0.514 g, 2.4 mmol) were mixed with catalyst and reacted in the same manner as in example 18. The title compound was isolated as white crystals of the dihydrochloride. Yield: 260 mg (28%)

LC-MS (electrospray): m/z: 400 (M+1); Rt=0.86 min.

$^1$H NMR (400 MHz, D$_2$O) δ: 9.13 (d, 1H), 8.79 (dd, 1H), 8.15 (m, 3H), 8.08 (d, 2H), 4.41 (s, 2H), 3.87 (m, 1H), 3.68 (m, broad, 2H), 3.48 (m, 2H), 3.42 (m, broad, 2H), 3.25 (m, broad, 2H), 3.06 (m, broad, 2H), 2.45 (m, 2H), 2.30 (m, 2H), 1.95 (m, 2H), 1.33 (t, 3H).

EXAMPLE 44

General Procedure F

1-[5-(4-Ethanesulfonylphenyl)pyridin-2-ylmethyl]-4-isopropylpiperazine, dihydrochloride

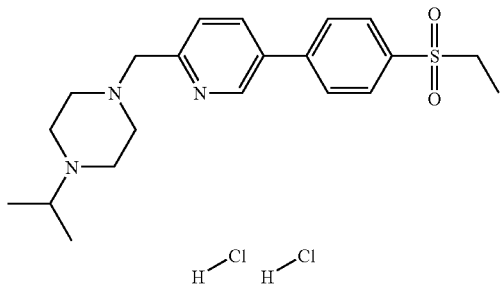

1-(5-Bromopyridin-2-ylmethyl)-4-isopropylpiperazine (0.596, 2.0 mmol) and 4-ethylsulfonylphenylboronic acid (0.514 g, 2.4 mmol) were mixed with catalyst and reacted in the same manner as in example 18. The title compound was isolated as white crystals of the dihydrochloride. Yield: 140 mg (18%)

LC-MS (electrospray): m/z: 388 (M+1); Rt=0.83 min.

$^1$H NMR (400 MHz, D$_2$O) δ: 8.92 (d, 1H), 8.56 (dd, 1H), 7.93 (m, 3H), 7.87 (m, 2H), 4.21 (s, 2H), 3.49 (q, 3H), 3.29 (Q, 6H), 2.91 (m,broad, 2H), 1.26 (d, 6H), 1.11 (t, 3H).

EXAMPLE 45

General Procedure F

{4-[6-(4-Cyclobutylpiperazin-1-ylmethyl)pyridin-3-yl]phenyl}-(4-methylpiperazin-1-yl)-methanone, trihydrochloride

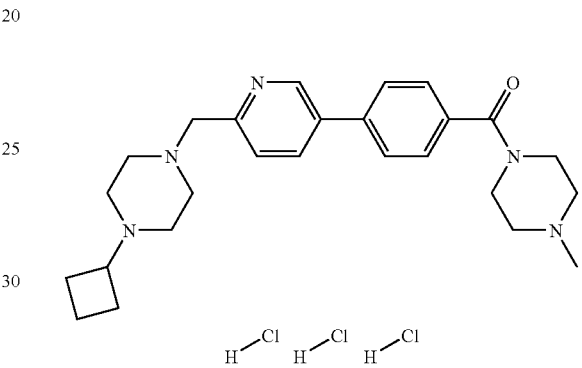

1-(5-Bromopyridin-2-ylmethyl)-4-cyclobutylpiperazine (0.62, 2.0 mmol) and 4-((4-methylpiperazin-1-yl)-4-(4,4,5,5-tetramethyl-[1,3,2]dioxoborolan-2-yl)phenyl)methanone (0.73 g, 2.4 mmol) were mixed with catalyst and reacted in the same manner as in example 18. The title compound was isolated as white crystals of the trihydrochloride. Yield: 260 mg (28%)

LC-MS (electrospray): m/z: 434 (M+1); Rt=0.57 min.

$^1$H NMR (400 MHz, D$_2$O) δ: 9.05 (d, 1H), 8.63 (d,d, 1H), 7.98 (d, 1H), 7.92 (d, 2H), 7.70 (d, 2H), 4.19 (s, 2H), 3.78 (m, 1H), 3.54 (m, broad, 8H), 3.24 (m, broad, 6H), 2.96 (s, 3H), 2.92 (m, broad, 2H), 2.35 (m, 4H), 1.91 (m, 2H).

EXAMPLE 46

General Procedure F

{4-[6-(4-Isopropylpiperazin-1-ylmethyl)pyridin-3-yl]phenyl}-(4-methylpiperazin-1-yl)-methanone, trihydrochloride

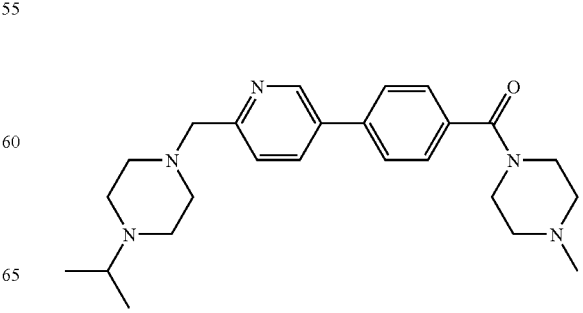

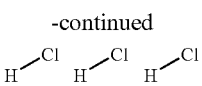

1-(5-Bromopyridin-2-ylmethyl)-4-isopropylpiperazine (0.596, 2.0 mmol) and 4-((4-methylpiperazin-1-yl)-4-(4,4,5,5-tetramethyl-[1,3,2]dioxoborolan-2-yl)phenyl)methanone (0.73 g, 2.4 mmol) were mixed with catalyst and reacted in the same manner as in example 18. The title compound was isolated as white crystals of the trihydrochloride. Yield: 226 mg (23%)

LC-MS (electrospray): m/z: 422 (M+1); Rt=0.55 min.

$^1$H NMR (400 MHz, CDCl$_3$) δ: 8.80 (d, 1H), 7.85 (dd, 1H), 7.61 (d. 2H), 7.50 (m, 3H), 3.83 (m,broad, 2H), 3.62 (s, 2H), 3.50 (m,broad, 2H), 2.69 (m, 1H), 2.62 (m,broad, 8H), 2.50 (m,broad, 2H), 2.38 (m,broad, 2H), 2.34 (s, 3H), 1.07 (d, 6H).

EXAMPLE 47

General Procedure F

{4-[5-(4-Isopropylpiperazin-1-ylmethyl)pyridin-2-yl]phenyl}-(4-methylpiperazin-1-yl)-methanone, trihydrochloride

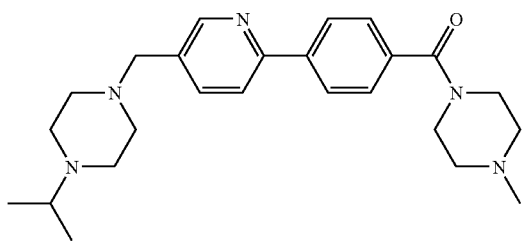

1-(6-Chloropyridin-3-ylmethyl)-4-isopropylpiperazine (0.5 g, 1.97 mmol) and 4-((4-methylpiperazin-1-yl)-4-(4,4,5,5-tetramethyl-[1,3,2]dioxoborolan-2-yl)phenyl)methanone (0.716 g, 2.2 mmol)) were mixed with catalyst and reacted in the same manner as in example 18. The title compound was isolated as white crystals of the trihydrochloride. Yield: 1.0 g (96%)

LC-MS (electrospray): m/z: 422 (M+1); Rt=0.548 min.

$^1$H NMR (400 MHz, MeOH-D4) δ: 8.88(s, 1H), 8.55(d,d, 1H), 8.3(d, 2H), 7.75(d, 2H), 4.2(s, 2H), 3.1-3.7(m, 17H), 3.0(s, 3H), 1.4(d, 6H).

EXAMPLE 48

General Procedure F

4-[5-(4-Isopropylpiperazin-1-ylmethyl)pyridin-2-yl]-N,N-dimethylbenzenesulfonamide, trihydrochloride

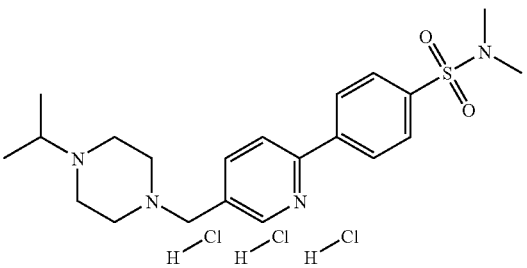

1-(6-Chloropyridin-3-ylmethyl)-4-isopropylpiperazine (0.5 g, 1.97 mmol) and 4-(N,N-dimethylaminosulfonyl)phenylboronic acid (0.496 g, 2.2 mmol)) were mixed with catalyst and reacted in the same manner as in example 18. The title compound was isolated as white crystals of the trihydrochloride. Yield: 660 g (71%)

LC-MS (electrospray): m/z: 403 (M+1); Rt=0.947 min.

$^1$H NMR (400 MHz, DMSO-D6) δ: 8.85(s, 1H), 8.3(d, 2H), 8.15(m, 2H), 7.85(d, 2H) 4.45(s, 2H), 3.3-3.65(m, 9H), 2.66(s, 6H), 1.25(d, 6H).

EXAMPLE 49

General Procedure F

4-{4-[5-(4-Isopropylpiperazin-1-ylmethyl)pyridin-2-yl]benzenesulfonyl}morpholine, dihydrochloride

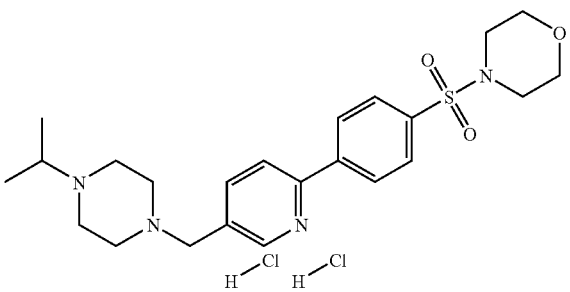

1-(6-Chloropyridin-3-ylmethyl)-4-isopropylpiperazine (0.5 g, 1.97 mmol) and 4-(N-morpholinyl-sulfonyl)phenylboronic acid (0.588 g, 2.2 mmol)) were mixed with catalyst and reacted in the same manner as in example 18. The title compound was isolated as white crystals of the dihydrochloride. Yield: 554 g (54%)

LC-MS (electrospray): m/z: 445 (M+1); Rt=0.955 min.

¹H NMR (400 MHz, DMSO-D6) δ: 8.9(s, 1H), 8.48(d, 2H), 8.2(d, 2H), 7.88(d, 2H), 4.5(s, 2H), 3.3-3.55(m, 13H), 2.9(m, 4H), 1.28(d, 6H).

EXAMPLE 50

General Procedure F

1-Cyclobutyl-4-{5-[4-(2-pyrrolidin-1-ylethyl)phenyl]pyridin-2-ylmethyl}piperazine, trihydrochloride

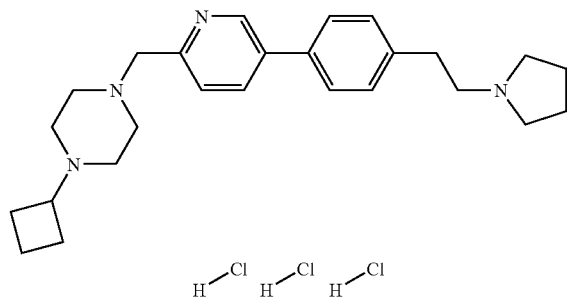

1-(5-Bromopyridin-2-ylmethyl)-4-cyclobutylpiperazine (0.62, 2.0 mmol) and 1-{2-[4-(4,4,5,5-tetramethyl-1,3,2-dioxaborolan-2-yl)phenyl]ethyl}pyrrolidine (0.723 g, 2.4 mmol) were mixed with catalyst and reacted in the same manner as in example 18. The title compound was isolated as white crystals of the trihydrochloride. Yield: 380 mg (47%).

LC-MS (electrospray): m/z: 405 (M+1); Rt=0.66 min.

¹H NMR (400 MHz, D₂O) δ: 8.77 (d, 1H), 7.82 (dd, 1H), 7.50 (d, 2H), 7.44 (d, 1H), 7.32 (d, 2H), 3.72 (s, 2H), 2.90 (m, 2H), 2.75 (m, 3H), 2.61 (m, 8H), 2.42 (m broad, 4H), 2.02 (m, 2H), 1.87 (m, 6H), 1.69 (m, 2H).

EXAMPLE 51

General Procedure F

1-Isopropyl-4-{5-[4-(2-pyrrolidin-1-ylethyl)phenyl]pyridin-2-ylmethyl}piperazine, trihydrochloride

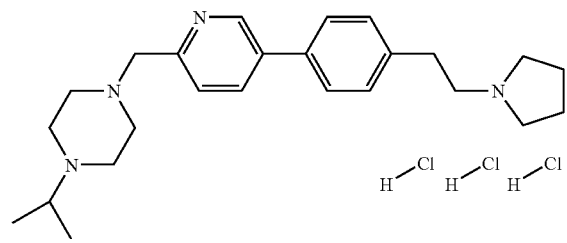

1-(5-Bromopyridin-2-ylmethyl)-4-isopropylpiperazine (0.62, 2.0 mmol) and 1-{2-[4-(4,4,5,5-tetramethyl-1,3,2-dioxaborolan-2-yl)phenyl]ethyl}pyrrolidine (0.723 g, 2.4 mmol) were mixed with catalyst and reacted in the same manner as in example 18. The title compound was isolated as white crystals of the trihydrochloride. Yield: 352 mg (45%)

LC-MS (electrospray): m/z: 393 (M+1); Rt=0.63 min.

¹H NMR (400 MHz, D₂O) δ: 8.87 (d, 1H), 8.61 (dd, 1H), 7.92 (d, 1H), 7.65 (d, 2H), 7.42 (d, 2H), 4.09 (s, 2H), 3.56 (m, 2H), 3.46 (m, 4H), 3.19 (m, 5H), 3.05 (m, 4H), 2.76 (m, 2H), 2.03 (m, 2H), 1.87 (m, 2H), 1.25 (d, 6H).

EXAMPLE 52

General Procedure F

1-Cyclobutyl-4-[5-(4-pyrrolidin-1-ylmethylphenyl)pyridin-2-ylmethyl]piperazine, trihydrochloride

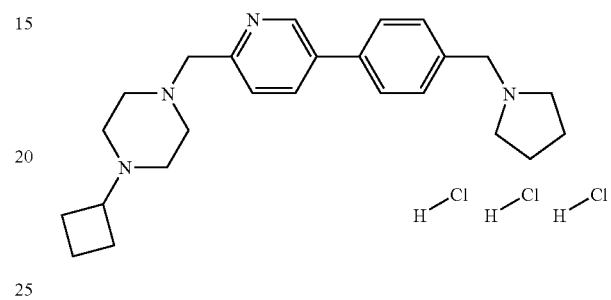

1-(5-Bromopyridin-2-ylmethyl)-4-cyclobutylpiperazine (0.62, 2.0 mmol) and 1-{2-[4-(4,4,5,5-tetramethyl-1,3,2-dioxaborolan-2-yl)phenyl]methyl}pyrrolidine (0.723 g, 2.4 mmol) were mixed with catalyst and reacted in the same manner as in example 18. The title compound was isolated as white crystals of the trihydrochloride. Yield: 391 mg (48%)

LC-MS (electrospray): m/z: 391 (M+1); Rt=0.65 min.

¹H NMR (400 MHz, D₂O) δ: 8.69 (d, 1H), 8.61 (dd, 1H), 7.93 (d, 1H), 7.72 (d, 2H), 7.56 (d, 2H), 4.10 (s, 2H), 3.63 (m, 1H), 3.42 (m,broad, 2H), 3.10 (m,broad, 2H), 2.97 (m,broad, 2H), 2.73 (m,broad,2H), 2.22 (m, 2H), 2.08 (m, 2H), 1.74 (m, 2H).

EXAMPLE 53

General Procedure F

4-[6-(4-Cyclobutylpiperazin-1-ylmethyl)pyridin-3-yl]benzonitrile

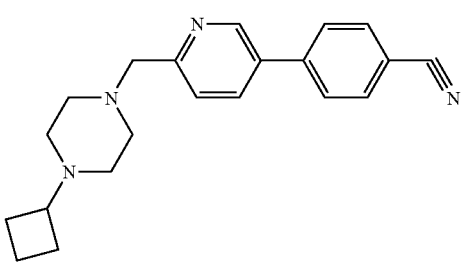 [SMILES: N#Cc1ccc(-c2ccc(CN3CCN(C4CCC4)CC3)nc2)cc1]

1-(5-Bromopyridin-2-ylmethyl)-4-cyclobutylpiperazine (1.163, 3.75 mmol) and 4-cyanophenyl-boronic acid (0.82 g, 5.6 mmol) were mixed with catalyst and reacted in the same manner as in example 18. The title compound was isolated as white crystals of the free amine. Yield: 467 mg (44%)

LC-MS (electrospray): m/z: 333 (M+1); Rt=0.91 min.

$^1$H NMR (400 MHz, CDCl$_3$) δ: 8.81 (d, 1H), 7.86 (dd, 1H), 7.77 (d, 2H), 7.68 (d, 2H), 7.50 (d, 1H), 3.77 s, 2H), 2.86 (m, 1H), 2.68 (m, broad, 4H), 2.55 (m, broad, 4H), 2.05 (m, 4H), 1.73 (m, 2H).

EXAMPLE 54

General Procedure F

4-[6-(4-Isopropylpiperazin-1-ylmethyl)pyridin-3-yl]benzonitrile

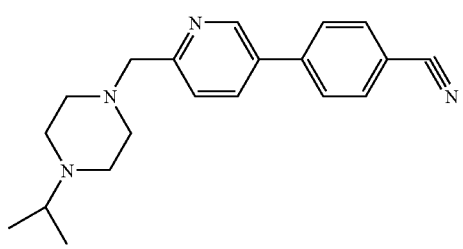 [SMILES: CC(C)N1CCN(Cc2ccc(-c3ccc(C#N)cc3)cn2)CC1]

1-(5-Bromopyridin-2-ylmethyl)-4-isopropylpiperazine (1.163, 3.75 mmol) and 4-cyanophenyl-boronic acid (0.82 g, 5.6 mmol) were mixed with catalyst and reacted in the same manner as in example 18. The title compound was isolated as white crystals of the free amine. Yield: 241 mg (20%)

LC-MS (electrospray): m/z: 321 (M+1); Rt=0.86 min.
$^1$H NMR (400 MHz, CDCl$_3$) δ: 8.80 (d, 1H), 7.85 (dd, 1H), 7.77 (d, 2H), 7.69 (d, 2H), 7.53 (d, 1H), 3.74 (s, 2H), 2.68 (m, 1H), 2.61 (s, 8H), 1.06 (d, 6H).

EXAMPLE 55

General Procedure F

4-[6-(4-Cyclobutylpiperazin-1-ylmethyl)pyridin-3-yl]benzaldehyde

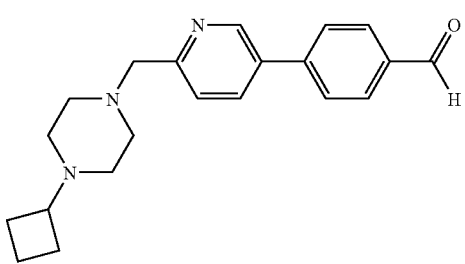 [SMILES: O=Cc1ccc(-c2ccc(CN3CCN(C4CCC4)CC3)nc2)cc1]

4-[6-(4-Cyclobutylpiperazin-1-ylmethyl)pyridin-3-yl]benzonitrile (0.066 g, 0.2 mmol) was dissolved in DCM (1 mL) DIBAL 1M in THF (0.2 mL) was added. The reaction mixture was stirred at RT for 1 hour. LC-MS showed no product. Another 1.5 eq. of DIBAL (0.2 mL) was added and stirring continued 1 hour. LC-MS showed full conversion. The reaction mixture was stored at −20° C. for 3 days. The reaction mixture was added DCM (5 mL) and cold NH$_4$Cl$_{aq}$ (5 mL). The DCM phase was washed with water (5 mL) and brine (5 mL), dried with MgSO$_4$, filtered and evaporation afforded the title compound as the free base. 34.5 mg (51%).

LC-MS (electrospray): m/z: 336.7 (M+1); Rt=0.84 min.

EXAMPLE 56

General Procedure F

4-[5-(4-Isopropylpiperazin-1-ylmethyl)pyridin-2-yl]-N,N-dimethylbenzamide, dihydrochloride

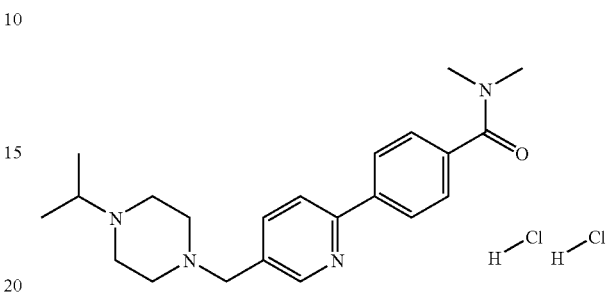

1-(6-Chloropyridin-3-ylmethyl)-4-isopropylpiperazine (0.5 g, 1.97 mmol) and N,N-dimethylbenzamide-4-boronic acid (0.418 g, 2.2 mmol)) were mixed with catalyst and reacted in the same manner as in example 18. The title compound was isolated as white crystals of the dihydrochloride. Yield: 637 g (74%)

LC-MS (electrospray): m/z: 367 (M+1); Rt=0.723 min.
$^1$H NMR (400 MHz, MeOH-D4) δ: 9.2(s, 1H), 8.9(d,d, 1H), 8.5(d, 1H), 8.1(d, 2H), 7.7(d, 2H), 4.65(s, 2H), 3.5-3.8 (m, 9H), 3.15(s, 3H), 3.05(s, 3H), 1.45(d, 6H).

EXAMPLE 57

General Procedure F

4-[6-(4-Isopropylpiperazin-1-ylmethyl)pyridazin-3-yl]-N,N-dimethylbenzenesulfonamide, dihydrochloride

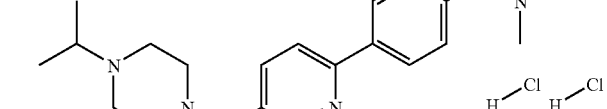

Step 1

3-Chloro-6-(4-isopropylpiperazin-1-ylmethyl)pyridazine, hydrochloride

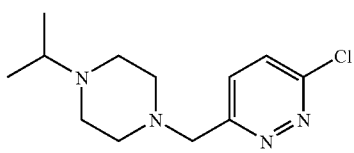

5-Chloro-3-chloromethylpyridazine (3.46 g, 21.2 mmol) and isopropylpiperazine (2.99 g, 23.3 mmol) were mixed in EtOH (10 mL). The stirred reaction mixture was heated for 1.5 hours. The mixture was cooled and the product was filtered off. 4.29 g (69%) white crystalline compound was isolated as the hydrochloride.

$^1$H NMR (400 MHz, CDCl$_3$) δ: 7.68 (d, J=9.10 Hz, 1H), 7.49 (d, J=9.10 Hz, 1H), 3.86 (s, 2H), 2.65 (septet, J=6.57 Hz, 1H), 2.56 (s, 8H), 1.05 (d, J=6.57 Hz, 6H).

Step 2

3-Chloro-6-(4-isopropylpiperazin-1-ylmethyl)pyridazine, hydrochloride (0.291g, 1 mmol) and (N,N-dimethylaminosulfonyl)phenylboronic acid (0.274 g, 1.2 mmol) were mixed with catalyst and reacted in the same manner as in example 18. The title compound was isolated as white crystals of the dihydrochloride. Yield: 226 g (62%)

LC-MS (electrospray): m/z: 368 (M+1); Rt=0.82 min.

$^1$H NMR (400 MHz, CDCl$_3$) δ: 8.26 (d, J=8.59 Hz, 2H), 7.93 (d, J=8.59 Hz, 2H), 7.89 (d, J=8.59 Hz, 1H), 7.78 (d, J=8.59 Hz, 1H), 3.97 (s, 2H), 2.76 (s, 6H), 2.73-2.52 (m, 9H), 1.07 (d, J=6.57 Hz, 6H).

EXAMPLE 58

General Procedure F

4-[6-(4-Isopropylpiperazin-1-ylmethyl)pyridazin-3-yl]-N,N-dimethylbenzamide, dihydrochloride 3-Chloro-6-(4-isopropylpiperazin-1-ylmethyl)pyridazine, hydrochloride (0.291 g, 1 mmol) and N,N-dimethylbenzamide-4-boronic acid (0.274 g, 1.2 mmol) were mixed with catalyst and reacted in the same manner as in example 18. The title compound was isolated as white crystals of the dihydrochloride. Yield: 226 g (62%)

LC-MS (electrospray): m/z: 368 (M+1); Rt=0.82 min.

$^1$H NMR (400 MHz, CDCl$_3$) δ: 8.13 (d, J=8.3 Hz, 2H), 7.85 (d, J=8.9 Hz, 1H), 7.73 (d, J=8.9 Hz, 1H), 7.58 (d, J=8.3 Hz, 2H), 3.94 (s, 2H), 3.15 (s, 3H), 3.03 (s, 3H), 2.67 (septet, J=6.4 Hz, 1H), 2.60 (br.s, 8H), 1.06 (d, J=6.4 Hz, 6H).

EXAMPLE 59

General Procedure F

{4-[6-(4-Isopropylpiperazin-1-ylmethyl)pyridazin-3-yl]phenyl}morpholin-4-ylmethanone, trihydrochloride

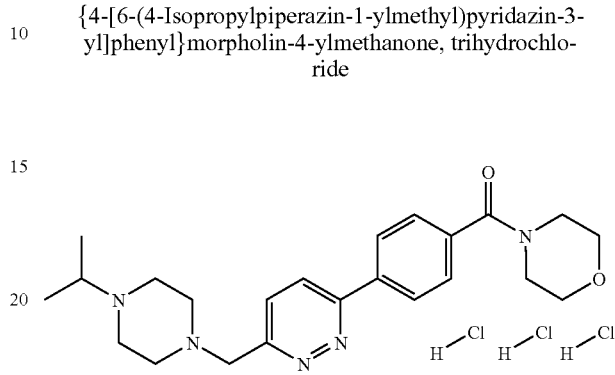

3-Chloro-6-(4-isopropylpiperazin-1-ylmethyl)pyridazine, hydrochloride (0.291 g, 1 mmol) and N-morpholinyl-1-carbonylphenyl-4-boronic acid (0.291 g, 1.2 mmol) were mixed with catalyst and reacted in the same manner as in example 18. The title compound was isolated as white crystals of the trihydrochloride. Yield: 230 g (44%)

LC-MS (electrospray): m/z: 410 (M+1); Rt=0.81 min.

$^1$H NMR (400 MHz, CDCl$_3$) δ: 8.14 (d, J=8.6 Hz, 2H), 7.85 (d, J=8.6 Hz, 1H), 7.74 (d, J=8.6 Hz, 1H), 7.57 (d, J=8.6 Hz, 2H), 3.95 (s, 2H), 3.82 (br.s, 4H), 3.68 (br.s, 2H), 3.51 (br.s, 2H), 2.67 (septet, J=6.6 Hz, 1H), 2.62 (br.s, 8H), 1.06 (d, J=6.6 Hz, 6H).

EXAMPLE 60

General Procedure F 3-(4-Ethanesulfonylphenyl)-6-(4-isopropylpiperazin-1-ylmethyl)pyridazine, dihydrochloride

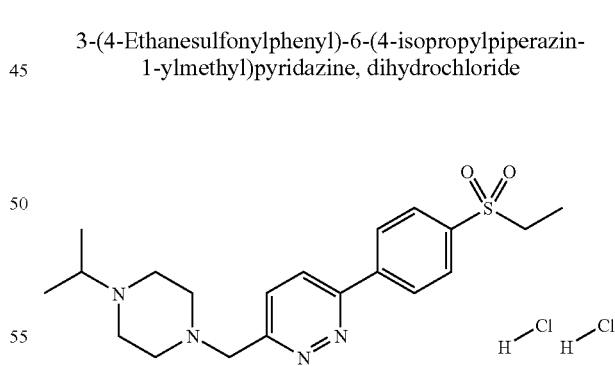

3-Chloro-6-(4-isopropylpiperazin-1-ylmethyl)pyridazine, hydrochloride (0.291 g, 1 mmol) and 4-ethylsulfonylphenyl-4-boronic acid (0.257 g, 1.2 mmol) were mixed with catalyst and reacted in the same manner as in example 18. The title compound was isolated as white crystals of the dihydrochloride. Yield: 236 g (61%)

LC-MS (electrospray): m/z: 389 (M+1); Rt=0.87 min.

$^1$H NMR (400 MHz, CDCl$_3$) δ: 8.29 (d, J=8.6 Hz, 2H), 8.06 (d, J=8.6 Hz, 2H), 7.90 (d, J=8.6 Hz, 1H), 7.80 (d, J=8.6

Hz, 1H), 3.97 (s, 2H), 3.18 (q, J=7.6 Hz, 2H), 2.68 (septet, J=6.4 Hz, 1H), 2.61 (br.s, 8H), 1.32 (t, J=7.6 Hz, 3H), 1.06 (d, J=6.6 Hz, 6H).

EXAMPLE 61

General Procedure F

{4-[6-(4-Isopropylpiperazin-1-ylmethyl)pyridazin-3-yl]phenyl}piperidin-1-ylmethanone, dihydrochloride

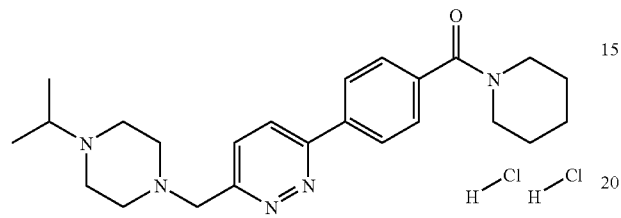

3-Chloro-6-(4-isopropylpiperazin-1-ylmethyl)pyridazine, hydrochloride (0.291 g, 1 mmol) and N-morpholinyl-1-carbonylphenyl-4-boronic acid (0.279 g, 1.2 mmol) were mixed with catalyst and reacted in the same manner as in example 18. The title compound was isolated as white crystals of the dihydrochloride. Yield: 236 g (61%)

LC-MS (electrospray): m/z: 408 (M+1); Rt=1.01 min.

$^1$H NMR (400 MHz, MeOH-D4) δ: 8.69 (d, J=8.6 Hz, 1H), 8.39 (d, J=8.6 Hz, 1H), 8.26 (d, J=8.6 Hz, 2H), 7.67 (d, J=8.6 Hz, 2H), 4.81 (s, 2H), 3.92-3.55 (m, 11H), 3.42 (br.s, 2H), 1.73 (br.s, 4H), 1.58 (br.s, 2H), 1.45 (d, J=6.6 Hz, 6H).

EXAMPLE 62

General Procedure F

{4-[6-(4-Isopropylpiperazin-1-ylmethyl)pyridazin-3-yl]phenyl}-(4-methylpiperazin-1-yl)-methanone, dihydrochloride

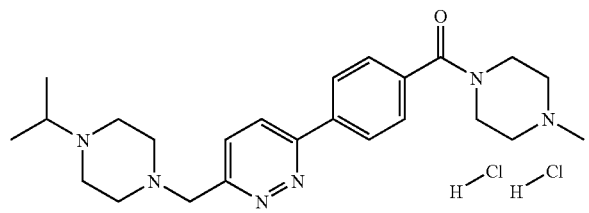

3-Chloro-6-(4-isopropylpiperazin-1-ylmethyl)pyridazine, hydrochloride (0.291 g, 1 mmol) and 4-((4-methylpiperazin-1-yl)-4-(4,4,5,5-tetramethyl-[1,3,2]dioxoborolan-2-yl)phenyl)methanone (0.396 g, 1.2 mmol) were mixed with catalyst and reacted in the same manner as in example 18. The title compound was isolated as white crystals of the dihydrochloride. Yield: 217 g (51%)

LC-MS (electrospray): m/z: 423 (M+1); Rt=0.59 min.

$^1$H NMR (400 MHz, MeOH-D4) δ: 8.47 (d, J=9.1 Hz, 1H), 8.27 (d, J=8.6 Hz, 2H), 8.16 (d, J=9.1 Hz, 1H), 7.74 (d, J=8.6 Hz, 2H), 4.51 (s, 2H), 3.72-3.18 (m, 17H), 2.98 (s, 3H), 1.43 (d, J=6.6 Hz, 6H).

EXAMPLE 63

General Procedure F

1-Isopropyl-4-[5-(4-pyrrolidin-1-ylmethylphenyl)pyridin-2-ylmethyl]piperazine, trihydrochloride

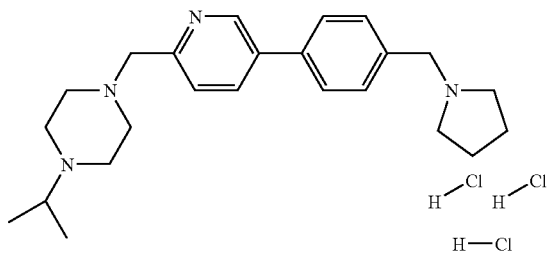

1-(5-Bromopyridin-2-ylmethyl)-4-isopropylpiperazine (0.62, 2.0 mmol) and 1-{2-[4-(4,4,5,5-tetramethyl-1,3,2-dioxaborolan-2-yl)phenyl]methyl}pyrrolidine (0.723 g, 2.4 mmol) were mixed with catalyst and reacted in the same manner as in example 18. The title compound was isolated as white crystals of the trihydrochloride. Yield: 453 mg (46%).

LC-MS (electrospray): m/z: 379.8 (M+1); Rt=0.62 min.

$^1$H NMR (400 MHz, CDCl$_3$) δ: 8.79 (d, 1H), 7.83 (d,d, 1H), 7.53 (d, 2H), 7.45 (m, 3H), 3.72 (s, 2H), 3.67 (s, 2H), 2.66 (m, 1H), 2.60 (m, 6H), 2.54 (m, 6H), 1.80 (m, 4H), 1.06 (d, 6H).

TEST RESULTS

| Example no. | Functional assay II Human H3 GTPγS Ki [nM] | Open cage schedule-fed rat model, dose 15 mg/kg p.o., food intake at 3 h [% of vehicle] |
|---|---|---|
| 11 | 26 | 85.9 |
| 29 | 8.4 | 74.4 |
| 42 | 17 | 87.8 |

| Example no. | hH3-GTPgS) [Ki] (nM) | Herg-binding. (3H-Astemizol) [Inhibition 10 μM] (%) | CYP1 Ainh [IC50] (μM) | CYP2 C19inh [IC50] (μM) | CYP2 C9inh [IC50] (μM) | CYP2 D6inh [IC50] (μM) | CYP3 A4inh [IC50] (μM) | Feed. Inhib. rat [Response 3 h] (%) |
|---|---|---|---|---|---|---|---|---|
| 11 | 26 | 19 | >25 | >25 | >25 | >25 | >25 | 85.9 |
| 29 | 8.4 | 7 | >25 | >25 | >25 | >25 | >25 | 74.4 |
| 42 | 17 | 7 | >25 | >25 | >25 | >25 | >25 | 87.8 |
| 2396 | 3.4 | 15 | >25 | >25 | >25 | >25 | >25 | 78.8 |

What is claimed is:

1. A compound of formula (I), or a pharmaceutically acceptable salt thereof,

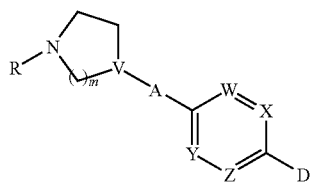

wherein:
W is —CH=;
X is =CH—;
Y is =N—;
Z is —CH=;
R is isopropyl, cyclobutyl, cyclopentyl, or 3-pentyl;
V is >CH—;
m is 2;
A is a bond or —CH$_2$—; and
D is:
 (i) phenyl substituted by one or two substituents selected from the group consisting of formyl, acetyl, anilino, amino, cyano, diisopropylcarbonyl, ethylsulfonyl, flouro, methyl -carbonylamino, 4-methylpiperazinyl-carbonyl, morpholin-4-yl, morpholin-4-ylcarbonyl, morpholin-4-ylsulfonyl, N,N-diethylaminocarbonyl, N,N-diethylaminomethyl, N,N-di -methylaminocarbonyl, N,N-dimethylaminomethyl, N,N-dimethylaminosulfonyl, piperidinylsulfonyl, pyrrolidinylcarbonyl, pyrrolidinylethyl, and pyrrolidinylmethyl, or, if substituted on two different carbon atoms in the phenyl ring, methylenedioxy; or
 (ii) pyridyl substituted by a methyl or an oxo group.

2. The compound of claim 1, where D is phenyl substituted by one or two substituents selected from the group consisting of formyl, acetyl, anilino, amino, cyano, diisopropylcarbonyl, ethylsulfonyl, flouro, methylcarbonylamino, 4-methylpiperazinylcarbonyl, morpholin-4-yl, morpholin-4-ylcarbonyl, morpholin-4-ylsulfonyl, N,N-diethylaminocarbonyl, N,N -diethylaminomethyl, N,N-dimethylaminocarbonyl, N,N-dimethylaminomethyl, N,N-dimethylaminosulfonyl, piperidinylsulfonyl, pyrrolidinylcarbonyl, pyrrolidinylethyl, and pyrrolidinylmethyl, or, if substituted on two different carbon atoms in the phenyl ring, methylenedioxy.

3. The compound of claim 1, where D is pyridyl substituted by a methyl or an oxo group.

4. The compound of claim 1, where the compound is a compound selected from the group consisting of:
5-[1,3-Benzodioxol-5-yl]-1'-isopropyl-1',2',3',4',5',6'-hexahydro-2,4'-bipyridine;
1'-Isopropyl-5-(4-morpholin-4-ylphenyl)-1',2',3',4',5',6'-hexahydro-[2,4']bipyridine;
1-Isopropyl-2"-methyl-1,2,3,4,5,6-hexahydro-[4,2';5',4"]terpyridine;
5-(4-Ethanesulfonylphenyl)-1'-isopropyl-1',2',3',4',5',6'-hexahydro-[2,4']bipyridine;
4-(1'-Isopropyl-1',2',3',4',5',6'-hexahydro-[2,4']bipyridinyl-5-yl)-N,N-dimethylbenzamide;
[2-Fluoro-4-(1'-isopropyl-1',2',3',4',5',6'-hexahydro-[2,4']bipyridinyl-5-yl)phenyl]pyrrolidin-1-yl -methanone;
3-(1'-Isopropyl-1',2',3',4',5',6'-hexahydro-[2,4']bipyridinyl-5-yl)-N,N-dimethylbenzamide;
N,N-Diethyl-4-(1'-isopropyl-1',2',3',4',5',6'-hexahydro-[2,4']bipyridinyl-5-yl)benzamide;
[4-(1'-Isopropyl-1',2',3',4',5',6'-hexahydro-[2,4']bipyridinyl-5-yl)phenyl]-(4-methylpiperazin-1-yl)methanone;
[4-(1'-Isopropyl-1',2',3',4',5',6'-hexahydro-[2,4']bipyridinyl-5-yl)phenyl]pyrrolidin-1-yl-methanone;
1'-Isopropyl-5[4-(piperidine-1-sulfonyl)phenyl]-1',2',3',4',5',6'-hexahydro-[2,4']bipyridine;
[4-(1'-Cyclobutyl-1',2',3',4',5',6'-hexahydro-[2,4']bipyridinyl-5-yl)phenyl]-(4-methylpiperazin-1-yl)methanone;
4-(1'-Cyclobutyl-1',2',3',4',5',6'-hexahydro-[2,4']bipyridinyl-5-yl)-N,N-dimethylbenzamide;
4-(1'-Cyclobutyl-1',2',3',4',5',6'-hexahydro-[2,4']bipyridinyl-5-yl)-N,N-diethylbenzamide;
[4-(1'-Cyclobutyl-1',2',3',4',5',6'-hexahydro-[2,4']bipyridinyl-5-yl)phenyl]pyrrolidin-1-yl-methanone;
1'-Cyclobutyl-5-(4-ethanesulfonylphenyl)-1',2',3',4',5',6'-hexahydro-[2,4']bipyridine;
4-(1'-Cyclobutyl-1',2',3',4',5',6'-hexahydro-[2,4']bipyridinyl-5-yl)-N,N-dimethylbenzene-sulfonamide;
1-Cyclobutyl-2"-methyl-1,2,3,4,5,6-hexahydro-[4,2';5',4"]terpyridine;
[4-(1'-Cyclobutyl-1',2',3',4',5',6'-hexahydro-[2,4']bipyridinyl-5-yl)benzyl]pipethylamine;
1'-Cyclobutyl-5-(4-pyrrolidin-1-ylmethylphenyl)-1',2',3',4',5',6'-hexahydro-[2,4']bipyridine;
[4-(1'-Cyclobutyl-1',2',3',4',5',6'-hexahydro-[2,4']bipyridinyl-5-yl)benzyl]dimethylamine;
{4-[6-(1-Cyclobutylpiperidin-4-ylmethyl)pyridin-3-yl]phenyl}-(4-methylpiperazin-1-yl)-methanone;
4-[6-(1-Cyclobutylpiperidin-4-ylmethyl)pyridin-3-yl]-N,N -dimethylbenzenesulfonamide;

6-(1-Cyclobutylpiperidin-4-ylmethyl)-2'-methyl-[3,4']bipyridine;

4-[6-(1-Cyclobutylpiperidin-4-ylmethyl)pyridin-3-yl]-N,N-dimethylbenzamide;

{4-[6-(1-Cyclobutylpiperidin-4-ylmethyl)pyridin-3-yl]phenyl}morpholin-4-ylmethanone;

{4-[6-(1-Cyclobutylpiperidin-4-ylmethyl)pyridin-3-yl]benzyl}dimethylamine; and 2-(1-Cyclobutylpiperidin-4-ylmethyl)-5-(4-ethanesulfonylphenyl)pyridine;

or a pharmaceutically acceptable salt thereof.

5. A compound where the compound is [4-(1'-isopropyl-1',2',3',4',5',6'-hexahydro-[2,4']bipyridinyl-5-yl)phenyl]-(4-methylpiperazin-1-yl)methanone or a pharmaceutically acceptable salt thereof.

6. A compound where the compound is [4-(1'-isopropyl-1',2',3',4',5',6'-hexahydro-[2,4']bipyridinyl-5-yl)phenyl]pyrrolidin-1-ylmethanone or a pharmaceutically acceptable salt thereof.

7. A compound where the compound is 6-(1-cyclobutylpiperidin-4-ylmethyl)-2'-methyl[3,4']bipyridine or a pharmaceutically acceptable salt thereof.

8. A compound where the compound is {4-[6-(1-cyclobutylpiperidin-4-ylmethyl)pyridin-3-yl]phenyl}morpholin-4-ylmethanone or a pharmaceutically acceptable salt thereof.

9. A compound where the compound is {4-[6-(1-cyclobutylpiperidin-4-ylmethyl)pyridin-3-yl]benzyl}dimethylamine or a pharmaceutically acceptable salt thereof.

10. A pharmaceutical composition comprising a compound of claim 1 and a pharmaceutically acceptable carrier or diluent.

11. A pharmaceutical composition comprising a compound of claim 5 and a pharmaceutically acceptable carrier or diluent.

12. A pharmaceutical composition comprising a compound of claim 6 and a pharmaceutically acceptable carrier or diluent.

13. A pharmaceutical composition comprising a compound of claim 7 and a pharmaceutically acceptable carrier or diluent.

14. A pharmaceutical composition comprising a compound of claim 8 and a pharmaceutically acceptable carrier or diluent.

15. A pharmaceutical composition comprising a compound of claim 9 and a pharmaceutically acceptable carrier or diluent.

16. A method of treating obesity in a human comprising: administering to a human in need thereof a compound of claim 1.

17. A method of inducing weight loss in a human comprising: administering to a human in need thereof a compound of claim 1.

18. A method of suppressing appetite in a human comprising: administering to a human in need thereof a compound of claim 1.

19. A method of inducing satiety in a human comprising: administering to a human in need thereof a compound of claim 1.

20. A compound of formula (I), or a pharmaceutically acceptable salt thereof,

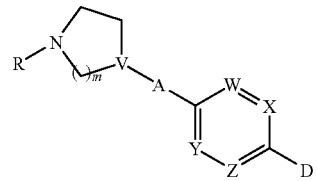

wherein:
W is —CH═;
X is ═CH—;
Y is ═N—;
Z is —CH═;
R is isopropyl, cyclobutyl, cyclopentyl, or 3-pentyl;
V is >N—;
m is 2;
A is —CH$_2$—; and
D is:
(i) phenyl substituted by one or two substituents selected from the group consisting of formyl, acetyl, anilino, amino, cyano, diisopropylcarbonyl, ethylsulfonyl, flouro, methyl-carbonylamino, 4-methylpiperazinylcarbonyl, morpholin-4-yl, morpholin-4-ylcarbonyl, morpholin-4-ylsulfonyl, N,N-diethylaminocarbonyl, N,N-diethylaminomethyl, N,N-di-methylaminocarbonyl, N,N-dimethylaminomethyl, N,N-dimethylaminosulfonyl, piperidinylsulfonyl, pyrrolidinylcarbonyl, pyrrolidinylethyl, and pyrrolidinylmethyl, or, if substituted on two different carbon atoms in the phenyl ring, methylenedioxy; or
(ii) pyridyl substituted by a methyl or an oxo group.

21. The compound of claim 20, where D is phenyl substituted by one or two substituents selected from the group consisting of formyl, acetyl, anilino, amino, cyano, diisopropylcarbonyl, ethylsulfonyl, flouro, methylcarbonylamino, 4-methylpiperazinylcarbonyl, morpholin-4-yl, morpholin-4-ylcarbonyl, morpholin-4-ylsulfonyl, N,N-diethylaminocarbonyl, N,N-diethylaminomethyl, N,N-dimethylaminocarbonyl, N,N-dimethylaminomethyl, N,N-dimethylaminosulfonyl, piperidinylsulfonyl, pyrrolidinylcarbonyl, pyrrolidinylethyl, and pyrrolidinylmethyl, or, if substituted on two different carbon atoms in the phenyl ring, methylenedioxy.

22. The compound of claim 20, where D is pyridyl substituted by a methyl or an oxo group.

23. The compound of claim 20, where the compound is a compound selected from the group consisting of:

4-[6-(4-Cyclobutylpiperazin-1-ylmethyl)pyridin-3-yl]-N,N-dimethylbenzamide;

4-[6-(4-Isopropylpiperazin1-ylmethyl)pyridin-3-yl]-N,N-dimethylbenzamide;

1-Cyclobutyl-4-[5-(4-ethanesulfonylphenyl)pyridin-2-ylmethyl]piperazine;

1-[5-(4-Ethanesulfonylphenyl)pyridin-2-ylmethyl]-4-isopropylpiperazine;

{4-[6-(4-Cyclobutylpiperazin-1-ylmethyl)pyridin-3-yl]phenyl}-(4-methylpiperazin 1yl)-methanone;

{4-[6-(4-Isopropylpiperazin-1-ylmethyl)pyridin-3-yl]phenyl}-(4-methylpiperazin-1yl)-methanone;

1-Cyclobutyl-4-{5-[4-(2-pyrrolidin-1-ylethyl)phenyl]pyridin-2-ylmethyl}piperazine;

1-Isopropyl-4-{5-[4-(2-pyrrolidin-1-ylethyl)phenyl]pyridin-2-ylmethyl}piperazine;

1-Cyclobutyl-4-[5-(4-pyrrolidin-1-ylmethylphenyl)pyridin-2-ylmethyl]piperazine;

4-[6-(4-Cyclobutylpiperazin-1-ylmethyl)pyridin-3-yl]benzonitrile;

4-[6-(4-Isopropylpiperazin-1-ylmethyl)pyridin-3-yl]benzonitrile;

4-[6-(4-Cyclobutylpiperazin-1-ylmethyl)pyridin-3-yl]benzaldehyde; and

1-Isopropyl-4[5-(4-pyrrolidin-1-ylmethylphenyl)pyridin-2-ylmethyl]piperazine;

or a pharmaceutically acceptable salt thereof.

24. A compound where the compound is 4-[6-(4-isopropylpiperazin-l-ylmethy) ppyridin-3-yl]-N,N-dimethylbenzamide or a pharmaceutically acceptable salt thereof.

25. A compound where the compound is 1-isopropyl-4-{5-[4-(2-pyrrolidin-l-ylethyl) phenyl]pyridin-2-ylmethyl}piperazine or a pharmaceutically acceptable salt thereof.

26. A compound where the compound is 4-[6-(4-isopropylpiperazin-1 -ylmethyl) pyridin-3-yl]benzonitrile or a pharmaceutically acceptable salt thereof.

27. A compound where the compound is 1-isopropyl-4-[5-(4-pyrrolidin-l-ylmethylphenyl) pyridin-2-ylmethyl]piperazine or a pharmaceutically acceptable salt thereof.

28. A pharmaceutical composition comprising a compound of claim 1 and a pharmaceutically acceptable carrier or diluent.

29. A pharmaceutical composition comprising a compound of claim 24 and a pharmaceutically acceptable carrier or diluent.

30. A pharmaceutical composition comprising a compound of claim 25 and a pharmaceutically acceptable carrier or diluent.

31. A pharmaceutical composition comprising a compound of claim 26 and a pharmaceutically acceptable carrier or diluent.

32. A pharmaceutical composition comprising a compound of claim 27 and a pharmaceutically acceptable carrier or diluent.

33. A method of treating obesity in a human comprising: administering to a human in need thereof a compound of claim 20.

34. A method of inducing weight loss in a human comprising: administering to a human in need thereof a compound of claim 20.

35. A method of suppressing appetite in a human comprising: administering to a human in need thereof a compound of claim 20.

36. A method of inducing satiety in a human comprising: administering to a human in need thereof a compound of claim 20.

* * * * *

UNITED STATES PATENT AND TRADEMARK OFFICE
CERTIFICATE OF CORRECTION

PATENT NO. : 8,344,001 B2
APPLICATION NO. : 12/663103
DATED : January 1, 2013
INVENTOR(S) : Rolf Hohlweg et al.

Page 1 of 1

It is certified that error appears in the above-identified patent and that said Letters Patent is hereby corrected as shown below:

In column 75, line 44, In Claim 1, delete "flouro," and insert -- fluoro, --, therefor.

In column 75, lines 47-48, In Claim 1, delete "N,N-di -methylaminocarbonyl," and insert -- N,N-dimethylaminocarbonyl, --, therefor.

In column 75, line 57, In Claim 2, delete "flouro," and insert -- fluoro, --, therefor.

In column 76, line 21, In Claim 4, delete "[4,2';5',4"]" and insert -- [4,2',5',4"] --, therefor.

In column 76, lines 55-56, In Claim 4, delete "[4,2';5',4"]" and insert -- [4,2',5',4"] --, therefor.

In column 77, line 24, In Claim 7, delete "methyl[3,4']bipyridine" and insert -- methyl-[3,4']bipyridine --, therefor.

In column 78, line 27, In Claim 20, delete "flouro," and insert -- fluoro, --, therefor.

In column 78, lines 30-31, In Claim 20, delete "N,N-di -methylaminocarbonyl," and insert -- N,N-dimethylaminocarbonyl, --, therefor.

In column 78, line 41, In Claim 21, delete "flouro," and insert -- fluoro, --, therefor.

In column 78, line 55, In Claim 23, delete "Isopropylpiperazin1" and insert -- Isopropylpiperazin-1 --, therefor.

In column 78, line 63, In Claim 23, delete "methylpiperazin 1yl)" and insert -- methylpiperazin-1-yl) --, therefor.

In column 79, line 27, In Claim 28, delete "claim 1" and insert -- claim 20 --, therefor.

Signed and Sealed this
Nineteenth Day of February, 2013

Teresa Stanek Rea
*Acting Director of the United States Patent and Trademark Office*